United States Patent [19]

Cargill et al.

[11] Patent Number: 5,118,183
[45] Date of Patent: Jun. 2, 1992

[54] AUTOMATED STRIP READER DENSITOMETER

[75] Inventors: Mark A. Cargill, Belding; Bernard J. Berg, Kentwood; Steven H. Peterson, Wyoming; Timothy R. Friend, Jenison; Thomas J. Boes, Grandville, all of Mich.

[73] Assignee: X-Rite, Incorporated, Grandville, Mich.

[21] Appl. No.: 480,331

[22] Filed: Feb. 13, 1990

Related U.S. Application Data

[63] Continuation of Ser. No. 309,342, Feb. 10, 1989, abandoned.

[51] Int. Cl.⁵ .................. G01N 21/00; G01N 21/25; G01J 3/51
[52] U.S. Cl. .................. 356/73; 356/406; 356/407; 356/419; 356/425
[58] Field of Search .................. 356/73, 404, 406, 407, 356/418, 419, 425, 443, 444, 446, 402, 405, 416; 364/526

[56] References Cited

U.S. PATENT DOCUMENTS

| | | | |
|---|---|---|---|
| 2,714,834 | 8/1955 | Patterson et al. | 356/444 |
| 3,244,062 | 4/1966 | Sweet | 356/444 |
| 3,376,426 | 4/1968 | Frommer et al. | |
| 4,061,428 | 12/1977 | Amano et al. | 356/175 |
| 4,239,393 | 12/1980 | Tobias | 356/407 |
| 4,289,405 | 9/1981 | Tobias | 356/407 |
| 4,402,611 | 9/1983 | Yuasa | 356/405 |
| 4,444,505 | 4/1984 | Imamoto et al. | 356/380 |
| 4,505,589 | 3/1985 | Ott et al. | 356/402 |
| 4,573,798 | 3/1986 | Fujie et al. | 356/432 |
| 4,624,571 | 11/1986 | Salda et al. | 356/406 |
| 4,653,926 | 3/1987 | Fukui | 356/444 |
| 4,671,661 | 6/1987 | Ott | 356/402 |
| 4,681,455 | 7/1987 | Jeschke et al. | 356/445 |
| 4,690,564 | 9/1987 | Morgenstern et al. | 356/445 |
| 4,773,761 | 9/1988 | Sugiyama et al. | 356/405 |
| 4,780,744 | 10/1988 | Porter et al. | 355/246 |
| 4,788,650 | 11/1988 | Willis et al. | 364/526 |
| 4,814,597 | 3/1989 | Kruger et al. | 250/205 |

FOREIGN PATENT DOCUMENTS

| | | | |
|---|---|---|---|
| 0011377 | 5/1980 | European Pat. Off. | |
| 601N2186 | 6/1981 | United Kingdom | 356/73 |
| 2064111 | 6/1981 | United Kingdom | |
| 2064111A | 6/1981 | United Kingdom | 356/73 |
| 601N2135 | 9/1983 | United Kingdom | 356/419 |
| 2147413A | 5/1985 | United Kingdom | 356/419 |
| 2147413 | 5/1985 | United Kingdom | |
| 2202939 | 10/1988 | United Kingdom | |

*Primary Examiner*—F. L. Evans
*Assistant Examiner*—K. P. Hantis
*Attorney, Agent, or Firm*—Varnum, Riddering, Schmidt & Howlett

[57] ABSTRACT

A densitometer apparatus (410) is disclosed and is adapted to provide color density measurements of object samples. The densitometer apparatus (410) comprises a source light (580) for projecting light toward an object sample comprising a control strip (588, 620). A reflection optics assembly (576) is adapted to measure light density reflected from the object sample when the object sample is in the form of a paper control strip. A transmission optics assembly (618) is adapted to measure transmission density of light rays projected through the object sample when the object sample is in the form of a film control strip. A motor assembly (426) operating with a drive wheel assembly (434) and idler wheel assembly (440) automatically moves the object sample (588, 620) through the apparatus (410) adjacent the source light (580). A pair of guides (468, 470) are selectively adjustable by the operator to control movement of the object sample (588, 620) through the apparatus (410). In response to input from a key switch assembly (492) activatable by the operator, the apparatus (410) is adapted to perform various color density measurement and calibration functions, and display appropriate information to the operator through the use of a visual display (490).

45 Claims, 31 Drawing Sheets

AUTOMATED STRIP READER DENSITOMETER

This is a continuation of application Ser. No. 309.342 filed Feb. 10. 1989. now abandoned.

TECHNICAL FIELD

The invention relates to densitometer apparatus and. more particularly. to apparatus having means for automated color density measurements of film. paper and print balance photographic reference and control strips.

BACKGROUND OF THE INVENTION

It is well known that the term "color" as applied to electromagnetic radiation represents in part the relative energy distribution of the radiation within the visible spectrum. That is. light providing a stimulus to the human eye. and having a particular energy distribution. may be perceived as a substantially different color then light of another energy distribution. Concepts relating to the characteristics of color and light waves are the subject of numerous well known texts. such as *Principles of Color Technology*. Meyer. Jr and Saltzman (Wiley 1966). and The Measurement of Appearance, Hunter and Harold (Wiley 2nd Ed 1987).

In recent years. the capability of maintaining the "quality" of color has been of significant importance in various industries. such as. for example. the fields of graphic arts. photography and color film processing. With respect to the graphic arts fields. it is necessary. for example. to maintain appropriate color quality throughout a production run of a color printing sheet.

For purposes of performing sample testing and other activities in furtherance of maintaining color quality. it is necessary to first determine an appropriate means for "measuring" and "describing" color. A substantial amount of research has been performed during the past 50 years with respect to appropriate methods and standards for color measurement and description.

For purposes of describing color. and from a purely physical point of view. the production of color requires three things: a source of light. an object to be illuminated. and a means for perceiving the color of the object. The means for perceiving the color can be the human eye and brain or. alternatively. a photosensitive detector and associated auxiliary equipment utilized for detecting light.

The maintenance of quality standards in photography requires precise control of exposure. source intensity. development procedures and film characteristics. in addition to the control of environmental variables. Similarly. the maintenance of quality standards in graphic arts also involves consideration of some of the same parameters and variables. In general, it is desirable to provide a means for measuring color so as to assess the manner in which an image will appear to a human observer, or the manner in which an image will perform in a photographic or other type of reproduction printing operation.

One parameter widely used in the field of color technology for obtaining a quantitative measurement is typically characterized as optical "density." Described simplistically, when light is directed onto an object or object sample to be measured for color, the object may absorb a portion of the light energy, while correspondingly passing through or reflecting (if the object is opaque) other portions of the light. The color characteristics of the object sample will depend in part on the spectral characteristics of the object. That is. the effect of an object on light can be described by its spectral transmittance or reflectance curves (for transparent or opaque materials. respectively). These spectral characteristic curves indicate the fraction of the source light at each wave length transmitted by or reflected from the materials. Such curves are a means for describing the effect of an object on light in a manner similar to the use of a spectral energy distribution curve for describing the characteristics of a source of light.

For purposes of determining these spectral characteristics. a detector can be appropriately positioned to respond to the light transmitted through or reflected by the object sample. Such a detector can. for example. be in the form of a photovoltaic device. Such a device can produce a current output proportional to input light intensity over several orders of magnitude.

In accordance with conventional optical physics. it is known that the proportion of light incident to an object sample and absorbed by such a sample is independent of the light intensity. Accordingly. a quantitative indication of the spectral characteristics of an object sample can be defined as the transmittance or reflectance of the sample. That is. the transmittance of a substantially transparent object can be defined as the ratio of power transmitted over light power incident to the sample. Correspondingly. for an opaque object sample. the reflectance can be defined as the ratio of power reflected from the object over the incident light power.

For collimated light. these ratios can be expressed in terms of intensities rather than power. Furthermore. because of the nature of transmittance/reflectance and the optical characteristics of the human eye. it is advantageous to express these ratios in logarithmic form. Accordingly. the optical density of an object sample is typically defined as the negative logarithm to base 10 of the transmittance or reflectance. In accordance with the foregoing. if an object sample absorbed 90% of the light incident upon it. and the object were opaque. the reflectance would ideally be 10%. The density of such a sample would then be characterized as unity. Correspondingly. if 99.9% of the light were absorbed. the reflectance would be 0.1% and the density would be 3. Similarly. the density of an "ideal" object reflecting 100% of the light incident upon it would be 0.

To provide a relative measurement of color. it is possible to utilize the principles of density determinations without requiring measurement or knowledge of the absolute values of total incident light intensity or reflectance. That is, for example, it is possible to obtain relative color measurements among a series of object samples by utilizing a particular geometric configuration of light, object sample and reflectance or transmittance detector for each measurement, and standardizing the measurements in some desired manner.

In brief summary, optical density is a measurement of the modulation of light or other radiant flux by an object sample, such as a given area of printed ink-on-paper. Density measurements provide a means to assess the manner in which an image will appear to a human observer, or the way an image will perform in a printing operation. Density measurements can be utilized to produce sensitometric curves to evaluate various printing and reproduction characteristics, as well as utilization to control various photographic operations, such as film processing.

For purposes of measuring optical densities. it is well known to employ a device typically characterized as a densitometer. For purposes of further description of the background of the invention, additional discussion will be limited to principles associated with "reflection" densitometers, which are employed for optical density measurements of opaque objects. However, it should be emphasized that the principles of the invention are not limited to reflection densitometers, and are equally applicable to transmittance densitometers employed for determining the spectral characteristics of various noneopaque materials.

Reflection densitometers are utilized in the graphic arts for performing a variety of functions. As an example, it is common to provide color printing sheets with color bar strips extending along an edge of the sheet. When such a printed sheet has been approved for production, the optical color density of the color bars can be determined with the densitometer. Thereafter, during production runs, the color bars on the edges of the corresponding printed sheets can be checked with the densitometer, so as to assure that appropriate color densities are being maintained.

In addition, reflection densitometers can be employed in the area of photography. For example, such a densitometer can be utilized to determine the optical density of the brightest or "highlight" areas, and the darkest or "shadow" areas of a subject to be photographed. Such values can be utilized in adjusting controls of the camera so as to assure appropriate exposure.

Still further, reflection densitometers can be conveniently employed in color film processing. It is common for color film manufacturers to provide test strips having color bars or patches. If the test strips have been appropriately processed, the bars will have known densitometer readings. Such strips can then be utilized to check operating parameters of a film processing system, before the system is utilized to process the exposed film.

Correspondingly, transmittance densitometers can also be employed with respect to film processing. For example, test strips of negatives having color bars can also be employed. Again, if the test strips have been appropriately processed, the bars will have known densitometer readings. These strips can be utilized to check operating parameters of a film processing system.

In addition to concepts associated with reflection measurements and transmittance measurements, it is also known to employ densitometers for providing printer balance functions.

To assist in describing the principles of the invention, presently known techniques of measuring optical density can be illustrated by the schematic representation of a known reflection densitometer configuration 100 as shown in FIG. 1. Referring to the numerical references therein, the prior art reflection densitometer 100 includes a light source unit 102 having a source light 104. With respect to optical density measurements in photography and other industrial fields, various standards have been developed for densitometer illuminating light sources. For example, densitometer standards have previously been described in terms of a tungsten lamp providing an influx from a lamp operating at a Planckian distribution of 3,000K. Other suggested standards have been developed by the American National Standards Institute ("ANSI") and the International Organization for Standardization ("ISO"). These light source densitometry standards are typically defined in terms of the spectral energy distribution of the illuminant.

The source light 104 is directed through a collimating lens 106 which acts to converge the electromagnetic radiation from the source light 104 into substantially parallel rays of light. The light rays transmitted through the lens 106 are further directed through an aperture 108. The dimensions of the aperture 108 will determine the size of the irradiated area of the object sample under test. Various standards have been defined for preferable sizes of the irradiated area. Ideally, the aperture 108 would be of a size such that the irradiance is uniform over the entire irradiated area. Current standards suggest that the size of the irradiated area should be such that irradiance measured at any point within the area is at least 90% of the maximum value.

The light rays transmitted through aperture 108 (illustrated as rays 110 in FIG. 1) are projected onto the irradiated area surface of the object sample 112 under test. The sample 112 may be any of numerous types of colored opaque materials. For example, in the printing industry, the sample 112 may be an ink-on-paper sample comprising a portion of a color bar at the edge of a color printing sheet. However, as will be apparent from the subsequent description herein, the principles of the current invention are not limited to measurement of printed ink-on-paper, photography or other specific fields.

As the light rays 110 are projected onto the object sample 112, electromagnetic radiation shown as light rays 114 will be reflected from the sample 112. For purposes of determining the relative proportions of light reflected from various object samples, it is necessary to obtain a quantitative measurement of this reflected light. However, it is undesirable (and substantially impossible) to measure all of the light reflected from the sample 112. Accordingly, standard detection configurations have been developed whereby reflected light is detected at a specific angle relative to the illumination light rays 110 projected normal to the plane of the object sample 112. More specifically, standards have been developed for detection of reflected light rays at an angle of 45° to the normal direction of the light rays 110.

For purposes of actual detection of the reflected light rays 114, a rotatable spectral filter apparatus 116 is provided. The filter apparatus 116 can include a series of filters 118, 120 and 122 which are employed for purposes of discriminating red, green and blue spectral responses, respectively. That is, each of the filters will tend to absorb light energy at frequencies outside of the bandwidth representative of the particular color hue of the filter. For example, the red filter 118 will tend to absorb all light rays except for those within the spectral bandwidth corresponding to a red hue and centered about a wavelength of approximately 610 nanometers (nms). By detecting reflected light rays only within a particular color hue bandwidth, and obtaining an optical density measurement with respect to the same, a "figure of merit" can be obtained with respect to the quality of the object sample coloring associated with that particular hue.

It is apparent from the foregoing that the actual quantitative measurement of color density or reflectance is dependent in substantial part on the spectral transmittance characteristics of the filters. Accordingly, various well known standards have been developed with respect to spectral characteristics of densitometer filters. For example, one standard for densitometer filters is known as the ANSI status T color response. The spectral response characteristics of filters meeting this standard are relatively wide band (in the range of 50 to 60 namometer bandwidth) for each of the red, blue and green color hues. Other spectral response characteristic standards include, for example, what is known as G-Response, which is somewhat similar to status T, but is somewhat more sensitive with respect to denser yellow hues. An E-Response represents a European response standard.

The spectral filter apparatus 116 shown in FIG. 1 includes not only the filters 118, 120 and 122, but is also shown as including a shaft 124 having one end connected to a "wheel" 126 on which the spectral filters are positioned and spaced apart. The other end of the shaft is connected to a manually rotatable knob 128. In the actual mechanical configuration of the densitometer 100, the knob 128 would be made accessible to the user for purposes of manual rotation of the wheel 126, so as to selectively position the individual filters as desired. In FIG. 1, the red filter 118 as shown as being appropriately positioned for detecting the reflected light rays 114.

The spectral filters 118, 120 and 122 can be any of several specific types of spectral response filters. For example, the filters 118, 120 and 122 can comprise a series of conventional Wratten gelatin filters and infrared glass. However, various other types of filter arrangements can also be employed.

As further shown in FIG. 1, the portion of the reflected light rays 114 which pass through the filters of the spectral filter apparatus 116 (shown as light rays 130) impinge on a receptor surface of a photovoltaic sensor cell 132. The sensor 132 is a conventional photoelectric element adapted to detect the light rays 130 emanating through the particular one of the filters 118, 120 and 122 then positioned to receive the reflected light rays 114. The sensor 132 is further adapted to generate an electrical current on line pair 134, with the magnitude of the output line current being proportional to the intensity of the light rays 130 sensed by the sensor 132. Photoelectric elements suitable for use as sensor 132 are well known in the art and various types of commercially available sensors can be employed.

The sensor current output on line pair 134 is applied as an input signal to a conventional amplifier 136. The amplifier 136 serves to convert the electrical current signal on line pair 134 to an output voltage signal on line 138. The amplifier 136 can include gain adjustment circuitry (representatively shown as an adjustable resistance in FIG. 1) 139 for purposes of varying the output voltage to input current gain. For example, a standard may be defined for the densitometer density reading for a particular spectral filter for zero density level. Accordingly, the amplifier circuit 136 can be adjusted by means of the gain adjustment circuitry 139 so that the densitometer reading is appropriate for the standard.

The output voltage signal from the amplifier 136 on line 138 can be applied as an input signal to a logarithmic voltage converter 140. The logarithmic voltage converter 140 is adapted to provide an output on line 142 which corresponds to the optical density measurement for the object sample 112 and the particular configuration of the spectral filter arrangement 116. This optical density measurement may be in the form of the negative logarithm (to the base 10) of the ratio of the voltage signal on line 138 to a standardized voltage magnitude. This standardized voltage magnitude can be set to a value which the user wishes to have correspond to a zero optical density measurement. That is, if the output voltage on line 138 is equal in magnitude to the standardized value, the logarithmic computation provided by the logarithmic converter 140 would generate a density measurement on line 142 of zero.

Preferably, the logarithmic converter 140 also has gain adjustment circuitry 144. This gain adjustment circuitry 144 can be utilized to set the density "slope" sensitivity of the converter 140. As is well known in the art of densitometer circuit design, logarithmic converters can vary in the response characteristics to input voltages. The gain adjustment provides a means for adjusting the response characteristics.

The voltage output from the logarithmic voltage converter 140 on line 142 can be applied to any of numerous types of conventional display apparatus 146. The display apparatus 146 is utilized to provide a visual display to the user of the density measurement represented by the logarithmic converter output voltage on line 142.

Although the foregoing prior art densitometer 100 has been described with the logarithmic conversion and gain adjustment functions represented by discrete components, it is apparent that such functions can clearly be performed by means of a digital computer or other computer apparatus.

As is well known in the art, densitometer apparatus must first be "calibrated" to provide a desired density response characteristic for a given set of spectral filters. In known systems, for example, and as briefly discussed in previous paragraphs, the "zero density" condition and the response "slope" for a particular densitometer and filter set can be provided as parameters manually input to the densitometer. For example, to provide what can be characterized as an "initial condition" of zero density for each individual spectral filter, an object sample comprising a "white" reference patch (representing substantial reflection) can be measured for each of the individual filters. The densitometer gain adjustments can then be manually adjusted so as to provide a standardized densitometer reading for the patch. Correspondingly, with the logarithmic density measurement assumed to be linear, the "slope" of the densitometer response can be set by means of viewing a "black" patch (representing substantial absorption), and setting the densitometer reading to a standardized "maximum" for the patch measurement for each of the filters.

Although the foregoing represents a means for calibrating zero density level measurements and density slope sensitivity, the known systems employing these calibration procedures still suffer from several substantial disadvantages. First, when standards are provided for adjusting the density level readings for a particular filter types, the standards assume an "ideal" filter. However, any physically realizable spectral filter arrangement will vary from the ideal. For example, in a conventional Wrattan filter configuration, such errors may be within the range of +−5 namometers. Such filter manufacturing errors can correspondingly result in errors as large as + or −0.08 density units in measurement of certain printed ink types. Such errors are critical, since desired industry inter-instrument agreement is within + or −0.02 density.

In addition, historical data regarding density measurements can be of primary importance, especially within the printing industry. That is, all printing being performed within a singular controlled environment should be capable of measurement by a number of densitometers in a manner so that the same results are achieved for identical measurements. However, if a series of conventional densitometers were utilized to measure the same color area, and were calibrated in accordance with the previously described procedures, the densitometers would not display identical measurement readings. Accordingly, if one densitometer had been used for an extensive period of time and had generated important historical printing data, such data would be substantially useless if the densitometer malfunctioned and a second densitometer instrument were subsequently utilized.

Problems associated with previously known calibration procedures result from several other considerations, in addition to the problems associated with manufacturing tolerances of spectral filter arrangements. For example, specification standards for various types of spectral filter arrangements call for certain types of light and color temperature, in addition to other illuminant parameters. However, manufacturing errors exist with respect to all physically realized illuminants. Furthermore, as a densitometer is used over a period of time, filament lamps will tend to drift. Still further, manufacturing errors will tend to exist with respect to photovoltaic detectors and other densitometer components. All of these factors result in problems associated with calibration based on standard spectral responses and the use of multiple densitometers for measuring color within a singular environment.

A substantial advance in the development of densitometers and calibration techniques has been provided in a densitometer arrangement disclosed in the commonly assigned U.S. patent application Ser. No. 105,424 filed Oct. 5, 1987. A densitometer arrangement as disclosed in the commonly assigned application is shown in FIG. 2. Densitometer apparatus of the type shown in FIG. 2 are characterized as reflection densitometers and utilized to provide color density measurements of opaque materials as previously described.

Several of the elements of the densitometer apparatus 200 were previously described with respect to the conventional densitometer configuration 100, and will only briefly be described herein. Referring specifically to FIG. 2, and the numerical references therein, the densitometer apparatus 200 includes a light source unit 202 having a source light 204. Various standards have been developed for densitometer light source illuminants for optical density measurements in photography, printing and other industrial fields. For example, densitometer standards have previously been described in terms of a tungsten lamp providing an influx from a lamp operating at a Planckian distribution of 3000K. Other suggested standards have been developed by the American National Standards Institute (ANSI) and the International Organization for Standardization ("ISO"). These source light densitometry standards are typically defined in terms of the spectral energy distribution of the illuminant. The source light 204 preferably conforms to an appropriate standard and can, for example, comprise a filament bulb meeting a standard conventionally known in the industry as 2856K ANSI. Power for the source light 204 and other elements of the densitometer apparatus 200 can be provided by means of conventional rechargeable batteries or, alternatively, interconnection to AC utility power.

The source light 204 projects light through a collimating lens 206 which serves to focus the electromagnetic radiation from the source light 204 into a narrow collimated beam of light rays. Various types of conventional and well-known collimating lenses can be employed. The light rays transmitted through the collimating lens 206 project through an aperture 208. The dimensions of the aperture 208 will determine the size of the irradiated area of the object sample under test. Various standards have been defined for preferable sizes of the irradiated area. Ideally, the aperture 208 is of a size such that the irradiance is uniform over the entire irradiated area. However, in any physically realizable densitometer arrangement, such uniform irradiance cannot be achieved. Current standards suggest that the size of the irradiated area should be such that irradiance measured at any point within the area is at least 90 percent of the maximum value. In addition, however, aperture size is typically limited to the size of color bar areas to be measured, and is also sized so as to reduce stray light.

The light rays emerging from the aperture 208 (illustrated as rays 210 in FIG. 2) are projected onto the irradiated area surface of an object sample 212 under test. The sample 212 may be any of numerous types of colored opaque materials. For example, in the printing industry, the sample 212 may be an ink-on-paper sample comprising a portion of a color bar at the edge of a color printing sheet. However, as will be apparent from the subsequent description herein, the principles of the invention are not limited to particular fields.

As the light rays 210 are projected onto the object sample 212, electromagnetic radiation shown as light rays 214 will be reflected from the sample 212. Standard detection configurations have been developed, whereby reflected light is detected at a specific angle relative to the illumination light rays 210 projected normal to the plane of the object sample 212. More specifically, standards have been developed for detection of reflected light rays at an angle of 45° to the normal direction of the light rays 110. This angle of 45° has become a standard for reflectance measurement and is considered desirable in that this configuration will tend to maximize the density range of the measurements. In addition, however, the 45° differential also represents somewhat of a relatively normal viewing configuration of a human observer (i.e. illumination at a 45° angle from the viewer's line of sight).

For purposes of providing light detection, a spectral filter apparatus 216 is provided. The filter apparatus 216 can include a series of filters 218, 220 and 222. The filters, 218, 220 and 222 are employed for purposes of discriminating the cyan, magenta and yellow spectral responses, respectively. That is, each of the filters will tend to absorb light energy at frequencies outside of the bandwidth representative of the particular color hue of the filter. For example, the cyan filter 218 will tend to absorb all light rays, except for those within the spectral bandwidth corresponding to a red hue. By detecting reflected light rays only within a particular color hue bandwidth, and obtaining an optical density measurement with respect to the same, a "figure of merit" can be obtained with respect to the quality of the object sample coloring associated with that particular color hue.

It is apparent from the foregoing that the actual quantitative measurement of color density of reflectance is dependent in substantial part on the spectral transmittance characteristics of the filters. Accordingly, various well-known standards have been developed with respect to spectral characteristics of densitometers filters. These standards were previously described with respect to the prior art densitometer apparatus 100 illustrated in FIG. 1.

Although the filters 218, 220 and 22 are illustrated in the embodiment shown in FIG. 2 as the cyan, magenta and yellow color shades, other color shades can clearly be employed. These particular shades are considered somewhat preferable in view of their relative permanence and because they comprise the preferred shades for use in reflection densitometer calibration. However, it is apparent that different shades of red, blue and yellow, as well as entirely different colors, can be utilized with the densitometer apparatus 200.

The spectral filters 218, 220 and 222 may not only comprise various shades of color, but can also be of any of several specific types of spectral response filters. For example, the filters can comprise a series of conventional Wratten gelatin filters and infrared glass. However, various other types of filter arrangements can also be employed.

The spectral filters 218, 220, 222 are preferably positioned at a 45° angle relative to the normal direction from the plane of the object sample 212 under test. However, unlike the densitometer configuration 100 previously described, each of the filters 218, 220 and 222 are maintained stationary and are utilized to simultaneously receive light rays reflected from the object sample 212 under test. Accordingly, it is unnecessary for the user to manually rotate or otherwise sequentially move spectral filters into receptive positions. Various types of densitometer structural configurations can be utilized to appropriately position each of the filters at the preferable 45° angular position.

As further shown in FIG. 2, the portion of the reflected light rays 214 which pass through the filters 218, 220 and 222 (shown as light rays 224, 226 and 228, respectively) impinge on receptor surfaces of photovoltaic sensor cells. The sensor cells are illustrated in FIG. 2 as sensors 232, 234 and 236 associated with the spectral filters 224, 226 and 228, respectively. The sensors 232, 234 and 236 can comprise conventional photoelectric elements adapted to detect the light rays emanating through the corresponding spectral filters. The sensors are further adapted to generate electrical currents having magnitudes proportional to the intensities of the sensed light rays. As illustrated in FIG. 2, the electrical current generated by the cyan sensor 232 in response to the detection of light rays projecting through the filter 218 is generated on line pair 238. Correspondingly, the electrical current generated by the magenta sensor 234 is applied to the line pair 240, while the electrical current generated by the yellow sensor 236 is applied as output current on line pair 242. Photoelectric elements suitable for use as sensors 236, 238 and 240 are well known in the art, and various types of commercially available sensors can be employed.

The magnitude of the electrical current on each of the respective line pairs will be proportional to the intensity of the reflected light rays which are transmitted through the corresponding spectral filter. These light rays will have a spectral distribution corresponding in part to the product of the spectral reflectance curve of the object sample 212, and the spectral response curve of the corresponding filter. Accordingly, for a particular color shade represented by the spectral response curve of the filter, the magnitude of the electrical current represents a quantitative measurement of the proportion of reflectance of the object sample 212 within the frequency spectrum of the color shade.

As further shown in FIG. 2, the sensor current output on each of the line pairs 238, 240 and 242 is applied as an input signal to one of three conventional amplifiers 244, 246 and 248. The amplifier 244 is responsive to the current output of cyan sensor 232 on line pair 238, while amplifier 246 is responsive to the sensor current output from magenta sensor 234 on line pair 240. Correspondingly, the amplifier 248 is responsive to the sensor current output from yellow sensor 236 on line pair 242. Each of the amplifiers 244, 246 and 248 provide a means for converting low level output current from the respective sensors on the corresponding line pairs to voltage level signals on conductors 250, 252 and 254, respectively. The voltage levels of the signals on the respective conductors are of a magnitude suitable for subsequent analog-to-digital (A/D) conversion functions. Such amplifiers are well known in the circuit design art and are commercially available with an appropriate volts per ampere conversion ratio, bandwidth and output voltage range. The magnitudes of the output voltages on lines 250, 252 and 254 again represent the intensity of reflected light rays transmitted through the corresponding spectral filters.

Each of the voltage signal outputs from the amplifiers is applied as an input signal to a conventional multiplexer 256. The multiplexer 256 operates so as to time multiplex the output signals from each of the amplifiers 244, 246 and 248 onto the conductive path 258. Timing for operation of the multiplexer 256 can be provided by means of clock signals from master clock 260 on conductive path 262. During an actual density measurement of an object sample, the densitometer 200 will utilize a segment of the resultant multiplexed signal which sequentially represents a voltage output signal from each of the amplifiers 244, 246 and 248.

The resultant multiplexed signal generated on the conductive path 258 is applied as an input signal to a conventional A/D converter 264. The A/D converter 264 comprises a means for converting the analog multiplexed signal on conductor 258 to a digital signal for purposes of subsequent processing by central processing unit (CPU) 266. The A/D converter 264 is preferably controlled by means of clock pulses applied on conductor 268 from the master clock 260. The clock pulses operate as "start" pulses for performance of the A/D conversion. The A/D converter 264 can be any suitable analog-to-digital circuit well known in the art and can, for example, comprise sixteen binary information bits, thereby providing a resolution of 64K levels per input signal.

The digital output signal from the A/D converter 264 is applied as a parallel set of binary information bits on conductive paths 270 to the central processing unit (CPU) 266. The CPU 266 can provide several functions associated with operation of the densitometer apparatus 200. In the embodiment described herein, the CPU 266 can be utilized to perform these functions by means of digital processing and computer programs. In addition, the CPU 266 can be under control of clock pulses generated from the master clock 260 on path 272. However, it should be emphasized that a number of the functional operations of CPU 266 could also be provided by means of discreet hardware components.

In part, the CPU 266 can be utilized to process information contained in the digital signals from the conductive paths 270. Certain of this processed information can be generated as output signals on conductive path 276 and applied as input signals to a conventional display circuit 278. The display circuit 278 provides a means for visual display of information to the user, and can be in the form of any one of several well known and commercially available display units.

In addition to the CPU 266 receiving digital information signals from the conductive paths 270, information signals can also be manually input and applied to the CPU 266 by means of a manually accessible keyboard circuit 280. The user can supply "adjustments" to color responses by means of entering information through the keyboard circuit 280. Signals representative of the manual input from the keyboard circuit 280 are applied as digital information signals to the CPU 266 by means of conductive path 282.

The previously described concepts of densitometry can be of primary significance in the color photography and processing industry. For purposes of illustration and example, the color photograph processing procedure can be described as comprising a series of three process steps. First, the exposed roll or strip of color film is subjected to a process for producing a series of "negatives" from the exposed film roll or strip. This process is well known in the photography industry and can essentially be characterized as a chemical process for producing a series of negative images, in which the "brightness" values of the photograph subject are reproduced so that the lightest areas are shown as the darkest areas.

Secondly, the color photography development process comprises a step wherein the photographic negative is utilized with photographic paper in a manner such that the photographic paper is subjected to exposure from the negative. In this process, the film base and exposure times can be varied as appropriate to achieve the proper color balance on the exposed paper. Finally, the exposed film paper is subjected to a chemical process for generating the finished photographic prints.

Each of the aforedescribed processes is relatively conventional and well known in the photographic industry. However, each of these processes requires the "setting" of various control variables on the equipment utilized to perform the processes. For example, the processes associated with producing the negatives and processing the exposed paper comprise chemical processes whereby color chemistry variables may be adjusted so as to produce negatives and finished prints of appropriate colors. Correspondingly, the process step whereby the photographic print paper is exposed from the negatives will also have various variables associated with the process. For example, this particular process will involve the use of "white" light sources and spectral filters for exposing the negative onto the photographic paper in differing manners. Further, a variable associated with this particular process comprises the exposure times for the exposure of the negative onto the photographic paper. As an example, the negative may be exposed onto the paper through an unfiltered white light source for a certain predetermined period of time. However, if such an exposure is not producing an appropriate color balance, filters may be employed whereby only a particular color (i.e. energy from a portion of the color spectrum) of the white light source is exposed onto the photographic paper for some portion of the entirety of the exposure time. This type of operation is typically referred to as a "balancing" of the color.

With respect to the final step of the photograph development process, i.e. the processing of the exposed photographic paper to produce the final photographic prints, a number of variables are also associated with this type of process. For example, the chemistry of the film bath may be varied through the use of various chemical mixtures so as to again achieve correct print processing to maintain appropriate photograph colors.

Various methods and equipment have been developed for providing the photograph developers with a means for measuring the "quality" of the individual process steps associated with the entirety of the photograph development process. In particular, it is relatively well known to utilize densitometers to measure optical transmittance density of processed negatives and optical reflectance density of processed photographic paper to determine if the equipment is producing appropriate color balances. However, when measuring color densities to determine the quality of the film processing, it is desirable to compare such density measurements against "ideal" processed materials. Accordingly, the field of film processing readily lends itself to the comparison of color densities of materials processed by the operator's own equipment against reference standards.

Further, however, the photography industry does not have any ideal standards relating to each of the process steps associated with film development. Additionally, optimum color densities of processed materials may vary dependent upon the particular type of film or paper material being utilized by the operator. Accordingly, manufacturers of film processing equipment and materials will provide their own individual reference standards for purposes of optimizing the film development process.

More specifically, it is known in the field of color photograph film processing to utilize "strips" of negative and paper materials to periodically test the quality of the operator's own processing equipment. In addition, manufacturers also provide "reference" strips of materials which can be characterized as processed strips comprising "ideal" processing of the manufacturers materials.

To further illustrate the use of the reference strips and the control strips, a strip commonly identified as the Kodak C-41 strip is illustrated in FIG. 4. The C-41 strip is manufactured by Eastman Kodak Company. The strip illustrated in FIG. 4 is identified as strip 400 and comprises a film negative having various color hues associated with the negative. When the film development equipment operator is utilizing film negatives manufactured by Eastman Kodak, the operator will obtain a reference film strip and a series of control strips having a configuration shown in FIG. 4. The reference strip can be characterized as a negative which has been fully processed by the manufacturer. The negative is considered to comprise a series of color patches having the "ideal" color hues for the negative processing. Correspondingly, the control strips provided by the manufacturer will be a series of unprocessed strip negatives. The principal use and concept associated with these strips is to allow the operator to adjust the film negative processor so that the color densities of control strips processed by the negative processor will optimally "match" color densities of the reference strip.

To perform the operation of measuring the quality of the negative processing, a densitometer can first be used to measure the transmission densities of the reference strip. Again, these transmission densities represent ideal densities to be achieved by the equipment negative processor. Although it would be possible to utilize color density values somehow identified on the reference strip, such values may not comprise the same density values which will be measured by the operator's own densitometer. That is, the "absolute values" of the color densities are not particularly important. Instead, the quality of the film negative processing by the operator's equipment will be indicated by the comparison of the measured color densities of a processed control strip relative to the measured color densities of the reference strip. Because densitometers may vary in their measurement readings from one device to another, it is of primary importance that the color densities for the reference strip and the control strips be measured by the same device.

After measurement of the color densities associated with the reference strip, a control strip having a similar configuration to the strip 400 is processed by the operator, using the operator's own equipment. Following processing of the film negative, the processed control strip is now measured to determine the color densities associated therewith. The differences in the relative color density measurement values between the reference strip and the processed control strip will indicate to the operator whether any adjustments in the film negative processing operation are required. Indeed, many of the primary manufacturers will provide written "troubleshooting" manuals indicating the types of adjustments which may be necessary in view of certain types of differences between the density measurements associated with the processed control strip and the density measurements associated with the reference strip. As an example, the operator may find that the "green" density value for the processed control strips is continuously lower than the green density value for the reference strip. The written troubleshooting manuals may then provide suggestions as to the particular activities which may be undertaken by the operator with respect to adjustment of the negative processor equipment.

With respect to adjustments to the processing equipment associated with the exposure of the negative onto the photographic paper, manufacturers provide reference and control strips commonly referred to as "print balance" strips. Such a print balance control strip is illustrated in FIG. 5 as print balance strip 402. As shown in FIG. 5, the strip comprises three color patches identified as the "over", "normal" and "under" patches. These patches comprise color densities which may be expected with respect to photographic paper that has been overexposed, normal and underexposed, respectively. The print balance control strips are employed to maintain a printing balance during the exposure of a negative onto the photographic paper. Again, in a similar manner with respect to the processing step associated with processing the negatives, the manufacturer will provide a print balance reference strip, in addition to a series of unprocessed print balance strips. The operator would again measure the color densities of the patches of the reference strip representative of overexposure, normal processing and underexposure. These color density values would then be compared against the actual color density values of materials processed by the operator's own equipment. These measurements can assist the operator in adjusting exposure times and filtering so as to achieve a proper color balance in exposing the negative onto the photographic paper.

With respect to the third step of the overall development process, i.e. the processing of the exposed photographic paper to obtain the final photographic prints, the manufacturers provide further reference and control strips to adjust variables in the processing step. A control strip commonly identified as the Kodak EP-2 strip (manufactured by the Eastman Kodak Company) is illustrated as control strip 404 in FIG. 6. Again, the operator would be provided with a reference strip having the "ideal" color densities. That is, the reference strip would comprise a strip of photographic print having the ideal color densities for this processing step. The operator would measure these reflection color densities and compare the densities against control strips processed by the operator's own equipment. Manufacturers provide written troubleshooting manuals for this processing step in a manner similar to the materials provided for the production of the film negatives. That is, differences in the measured color densities will typically indicate certain problems associated with this step of the film processing. As an example, a relatively substantial distinction in the color densities of particular color patches between a processed control strip and the reference strip may indicate that the bath temperature for the processing of the final photographic print is not appropriate.

The common use of control strips as previously described herein with respect to photographic processing raises several issues. For example, it can be noted that the entirety of the process as described above involves the measurement of optical transmission densities (for the negatives) and optical reflection densities (for the film paper). In addition, it is apparent that the measurement of the color densities of the reference strips and the control strips can involve a substantial amount of manual manipulation. Accordingly, it would clearly be advantageous to employ a densitometer having the combined functions of reflection density measurement and transmission density measurement. In addition, it would also be advantageous to provide a means for "automating" the density measurement functions, dependent upon the particular types of standardized reference and control strips being employed. For purposes of the description of the illustrative embodiment of the invention as subsequently disclosed herein, references to "control strips" will refer to both reference strips and control strips.

SUMMARY OF THE INVENTION

In accordance with the invention, a densitometer system is adapted for measuring color characteristics of object samples under test. The system includes light source means for generating light rays and directing the same onto the object samples. Filter means are responsive to the light rays reflected from the object samples, so as to discriminate predetermined color shade sets of spectral responses of the reflected light rays.

The densitometer system also includes detection means responsive to the light rays transmitted through the filter means, for purposes of generating signals representative of the intensity of the light rays transmitted through the filter means. Processing means are connected to the detection means for processing the signals and for generating data representative of color characteristics of the object samples.

Motive means are connected to the processing means and adapted to automatically move the object sampled under test through the densitometer system adjacent the light source means. In this manner, an automated measurement of a plurality of color patches associated with the object samples is provided. Further, guide means are mounted to the densitometer system and adjustable by an operator of the system, so as to provide a guidance in at least one dimension of the object samples through the densitometer system.

The filter means include reflection filter means positioned at a predetermined angle relative to the direction of object illumination by the light source means. The reflection filter means are responsive to light rays reflected from the object sample so as to discriminate a predetermined color shade set of spectral responses of the reflected light rays. In addition, the filter means include transmission filter means positioned relative to the direction of object illumination by the light source means. The transmission filter means are responsive to light rays transmitted through the object sample so as to discriminate a predetermined color shade set of spectral responses of the transmitted light rays.

The detection means also includes reflection detection means responsive to the light rays transmitted through the reflection filter means for generating, on separate paths, signals representative of the intensity of the light rays transmitted through the reflection filter means. Correspondingly, the detection means also includes transmission detection means responsive to the light rays transmitted through the transmission filter means for generating, on separate paths, signals representative of the intensity of the light rays transmitted through the transmission filter means.

In accordance with another aspect of the invention, the densitometer system includes multiplexing means connected to the detection means for time multiplexing the signals. The system also includes input means connected to the processing means for providing operator input to the densitometer system. Further, display means are provided which are connected to the processing means for providing visual displays to the operator, indicative of functions performed by the densitometer system.

The motive means can include an electric motor. Correspondingly, the guide means can include a film guide bar having an elongated configuration, and further having nubs or similar elements adapted to be secured into slots located adjacent a forward edge of a bottom housing of the densitometer system. The guide means also include a pair of film guides, including a left film guide and a right film guide for capturing an object sample under test for guidance in at least one dimension into the densitometer system.

The guide means can include a recessed portion of a housing assembly of the densitometer system, with the recessed portion including indicia for purposes of indicating the center of the path for color density measurement of the object samples under test. The guide means can also include numerical indicia located on a forward edge of a bottom housing of the densitometer system, with the numerical indicia centered with respect to the indicia positioned on the recessed portion, and extending lengthwise across the forward edge. Each of the film guides is manually adjustable by an operator for guiding and controlling guidance of an object sample under test into the densitometer system.

The densitometer system can also include reflection multiplexing means connected to the reflection detection means for time multiplexing the reflection signals on the separate paths. In addition, the densitometer system can also include transmission multiplexing means connected to the transmission detection means for time multiplexing the transmission signals on the separate paths.

In accordance with another aspect of the invention, the color characteristics include color densities, and at least one of the object samples is adapted for use as a calibration reference sample. The calibration reference sample includes at least one reference color patch and calibration indicating means for indicating previously measured color density values of the patch. The densitometer system further includes calibration means for adjusting slope between low and high color density measurements. The calibration means is adapted to read the calibration indicating means when the calibration reference sample is moved through the densitometer system adjacent the light source means. The calibration means is further adapted to adjust the slope based at least in part on the values of the reference color patch represented by the calibration indicating means.

The calibration indicating means includes a plurality of indicators. The position of each of the indicators is representative of a particular color density measurement value of the reference color patch. In addition, the calibration indicating means can include a plurality of color indicators and a reference indicator. The displacement of each of the color indicators relative to the reference indicator can be representative of particular color density measurement values of the reference color patch. Further, the displacement of at least one of the color indicators relative to the reference indicator can be representative of a particular color density measurement value of the color patch, while the displacement of at least another one of the color indicators relative to the reference indicator can be representative of another particular color density measurement value of the color patch, but offset by a predetermined value. In this manner, potential overlap of the color indicators is substantially avoided.

In accordance with a further aspect of the invention, the densitometer system includes means for providing information to the operator. This means provides such information for appropriate positioning of the guide means for purposes of guidance of individual ones of the object samples through the system.

BRIEF DESCRIPTION OF THE DRAWINGS

The invention will now be described with respect to the drawings, in which.

DETAILED DESCRIPTION

The principles of the invention are disclosed, by way of example, in a densitometer apparatus 410 as illustrated in FIGS. 3 and 7-30. The densitometer apparatus 410 comprises an automated strip reader color photographic densitometer, whereby film control strips, paper control strips and printer balance strips can be inserted for motorized and automatic measurements. In particular, the densitometer apparatus 410 is adapted to measure a plurality of different types of manufacturers' control strips, and sort data for measured fields, such as high density, low density and "stain." In addition, the densitometer apparatus 410 is adapted to display the data and, if desired by the operator, transmit the data to a peripheral device, such as a printer.

In the embodiment of a densitometer apparatus in accordance with the invention as described herein, the densitometer apparatus 410 is disclosed as providing an output of red, blue and green color density values for each measured field. However, it will be apparent to those skilled in the appropriate arts that various other color density outputs could be achieved without departing from any of the novel concepts of the invention. As will be further described herein, the densitometer apparatus 410 is adapted to measure both optical transmission densities (for film negatives) and optical reflection densities (for photographic paper) of the control strips. In addition, the densitometer apparatus 410 is also adapted to provide color density measurements of data aligned adjacent edges of a control strip or, alternatively, at the center of a control strip. Still further, and in accordance with the invention, the densitometer apparatus 410 is further adapted to provide automatic calibration for transmission and reflection densitometry.

Figure 7:
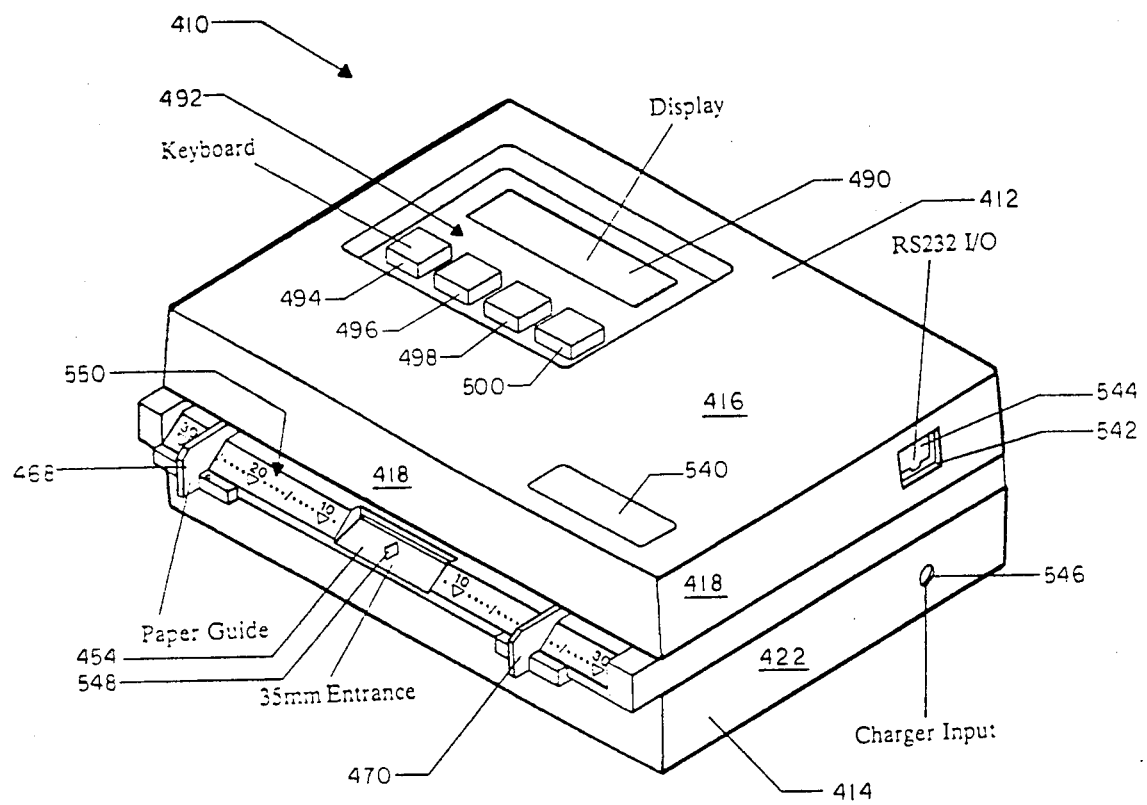
FIG. 7 is a perspective view of a densitometer apparatus in accordance with the invention.
Figure 8:
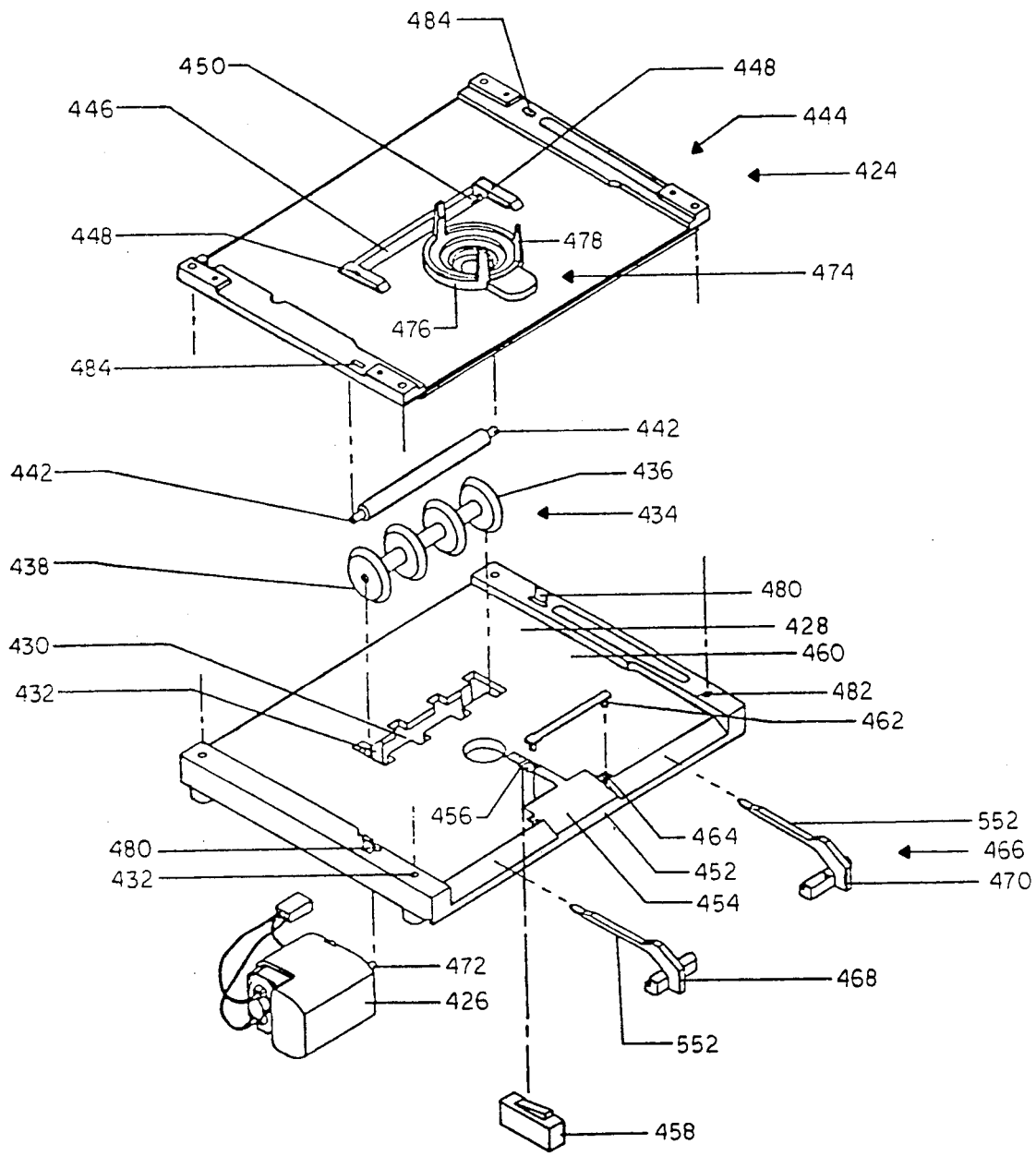
FIG. 8 is an exploded view of the densitometer apparatus shown in FIG. 7, and further showing the drive assembly for the apparatus.
Figure 9:
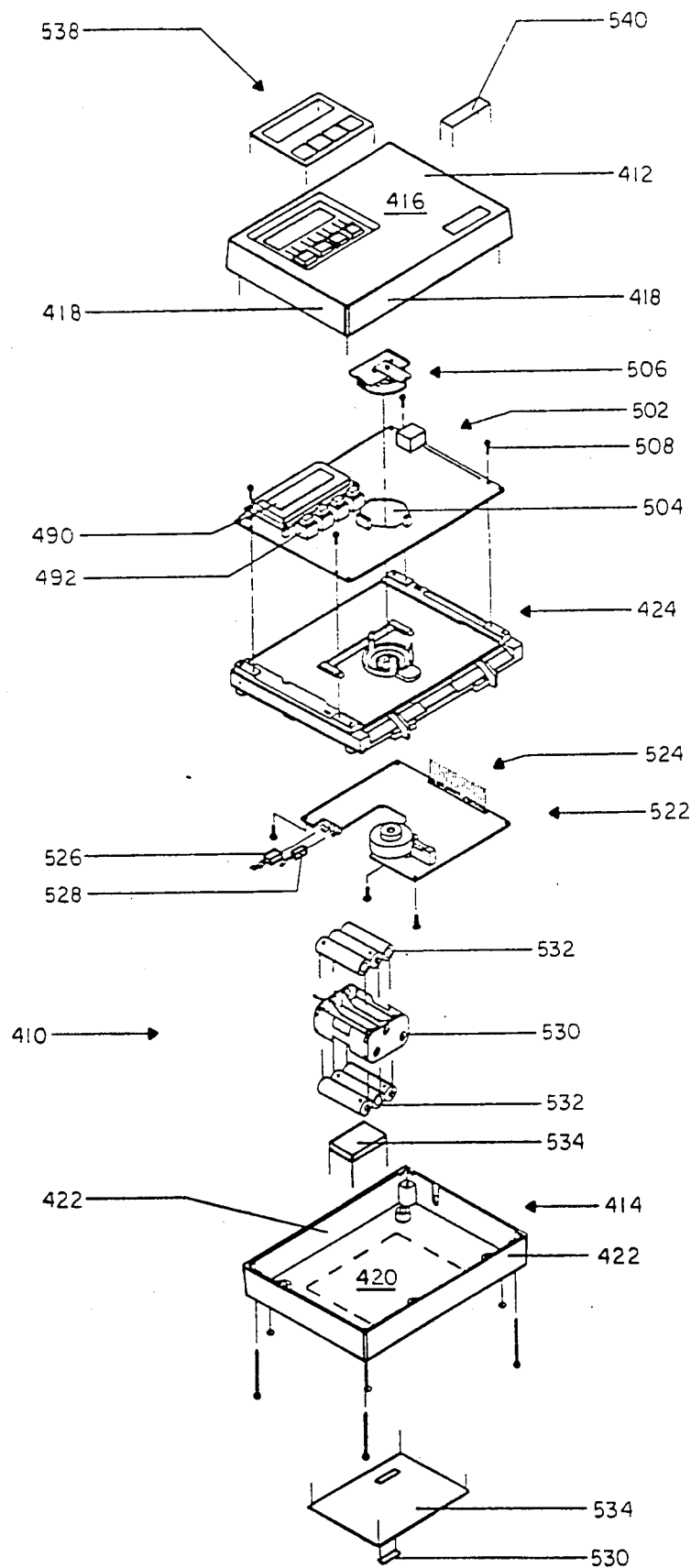
FIG. 9 is an exploded view of the apparatus shown in FIG. 7, and further showing various individual components of the apparatus.

The mechanical structure of the densitometer apparatus 410 is primarily illustrated in FIGS. 3 and 7 through 10. Referring specifically to FIG. 7, the densitometer apparatus 410 comprises a relatively compact structure suitable for use on a desk top or similar work surface. The apparatus 410 includes a top cover 412 and a bottom cover 414. The top cover 412 is primarily illustrated in FIGS. 7, 9 and 10, and comprises an upper surface 416 having a rectangular configuration and integral with downwardly extending side surfaces 418 at the edges thereof. As illustrated in FIG. 9, the bottom cover 414 comprises a lower and rectangular flat surface 420 having outwardly extending side surfaces 422 integral with the flat surface 420.

Figure 10:
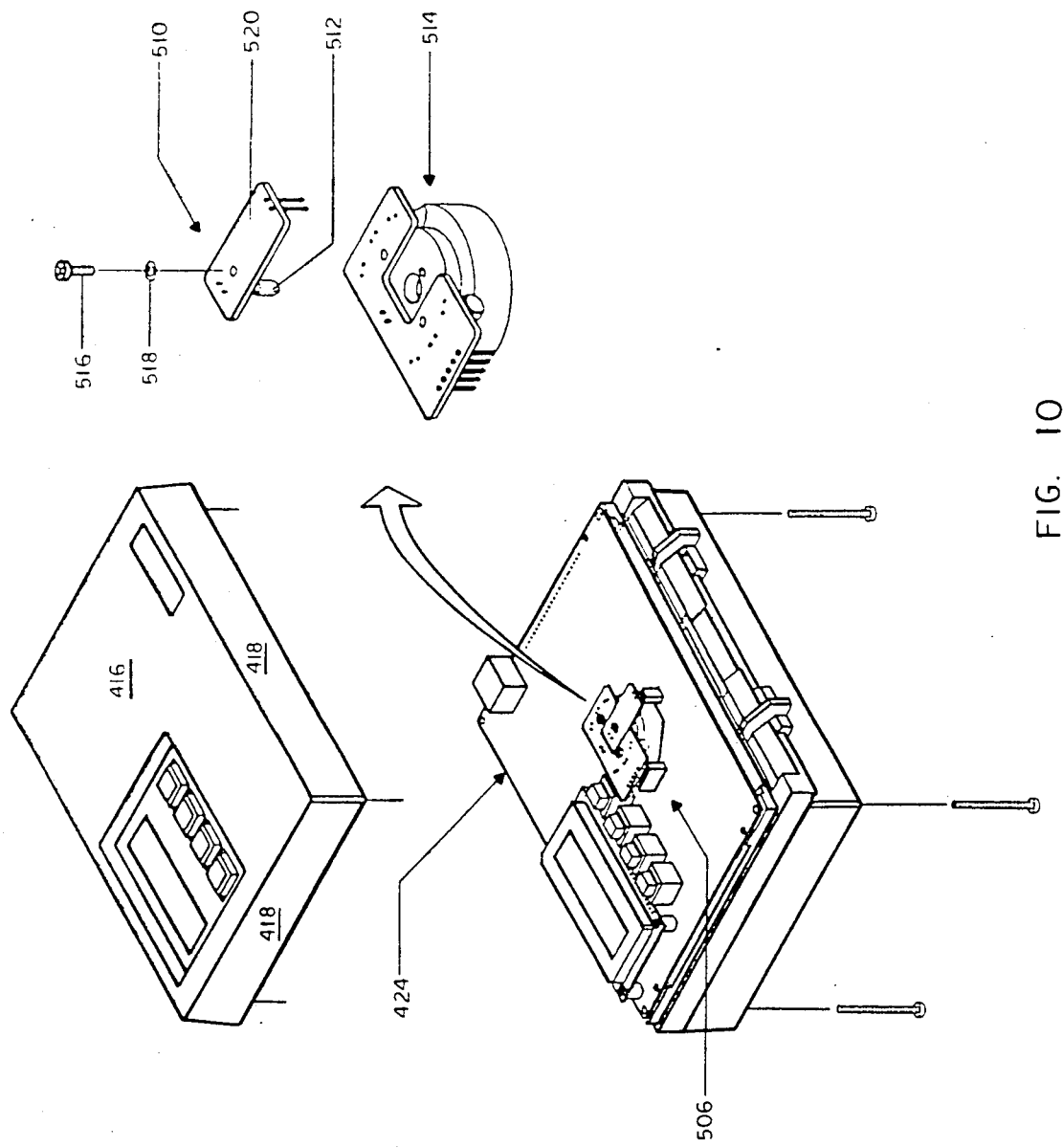
FIG. 10 is an exploded view of the densitometer apparatus shown in FIG. 7, and specifically showing elements of the lamp assembly of the apparatus.

Intermediate the top cover 412 and the bottom cover 414, and enclosed therebetween is a housing assembly 424 as primarily illustrated in FIGS. 8, 9 and 10, and specifically illustrated in an exploded view in FIG. 8. Referring specifically to FIG. 8, the housing assembly 424 comprises a motor assembly 426. The motor assembly 426 can be any of a series of conventional D.C. motors available on the commercial market. For example, the D.C. motor assembly 426 may comprise a D.C. motor having a rating of 6 volts and 300 milliamps, and manufactured by Buhler. The housing assembly 424 further comprises a bottom housing 428 having a structural configuration as illustrated in FIG. 8. The bottom housing 428 includes an aperture 430 having slots 432 for purposes of receiving a drive wheel assembly 434 comprising an axle 436 with a series of drive wheels 438 axially positioned on the axle 436. The slots 432 are adapted to partially receive each of the drive wheels 438.

In addition to the drive wheel assembly 434, the housing assembly 424 also comprises an idler wheel assembly 440 comprising an elongated and cylindrical structure as further illustrated in FIG. 8. Attached to each end of the idler wheel assembly 440 are a pair a spindles 442. The housing assembly 424 further comprises a top housing 444 having a structural configuration as illustrated in FIG. 8. The top housing 444 includes an aperture 446 having an elongated configuration and through which the idler wheel assembly 440 is partially received. Located at each end of the elongated aperture 446 is a brace 448 having recessed portions 450 adapted to rotatably receive the spindles 442 of the idler wheel assembly 440. Further, the braces 448 are spring loaded in a suitable manner so as to properly retain the idler wheel assembly 440.

Returning to the bottom housing 428 as illustrated in FIG. 8, the bottom housing further comprises a forward edge 452 having a slanted configuration and comprising a slightly recessed portion 454. The recessed portion 454 comprises a width appropriate for insertion of 35 millimeter (35 mm) film strips for color density measurements utilizing the apparatus 410. The bottom housing 428 additionally includes a slot 456 adapted to receive a conventional microswitch assembly 458. As it will be described subsequently herein, the microswitch assembly 458 comprises a "read" switch which is enabled by movement of a control strip into the densitometer apparatus 410 so as to activate the motor assembly 426.

The bottom housing 428 also comprises a film guide bar 460 having an elongated configuration and further having nubs 462 or similar elements adapted to be secured into slots 464 located adjacent the forward edge 452 of the bottom housing 428. In addition to the foregoing elements, a pair of film guides 466 are also included with the housing assembly 424. Specifically, the film guides 466 comprise a "left" film guide 468 and a "right" film guide 470. The film guides, as described subsequently herein, provide a means for guiding the control strip into the densitometer apparatus 410. Although not specifically shown in FIG. 8, the forward edge 452 of the bottom housing 428 can also comprise a series of numbered indicia indicating the relative positioning of the film guides 466.

As still further shown in FIG. 8, the motor assembly 426 comprises a driven shaft 472 which is adapted to be received through one end of the axle 436 of the drive wheel assembly 434. Accordingly, when the motor assembly 426 is activated, the drive shaft 472 will cause the drive wheel assembly 436 to rotate.

The top housing 444 can further comprise an optics assembly holder 474 which includes an aperture 476 which provides a slot for purposes of obtaining the transmission and reflection density measurements. The assembly holder 474 further comprises an annular portion 476 having a series of upright standards 478 extending upwardly therefrom.

For purposes of interconnecting the top housing 444 with the bottom housing 428, the bottom housing 428 includes a pair of standards 480 located substantially diagonal from each other and on opposing ledges 482 extending along opposing edges of the bottom housing 428. Correspondingly, the top housing 444 includes a pair of slots 484 positioned so as to be aligned with the standards 480. The alignment between the standards 480 and the slots 484 is such that the top housing 444 is essentially "snap" fitted with the bottom housing 428.

Returning to FIGS. 7 through 10, the densitometer apparatus 410 further comprises a visual display device 490 which can comprise, for example, a 2×16 LCD conventional display device. In addition, as further shown in FIG. 7, the apparatus 410 includes a keyboard 492 having a series of four key switches 494, 496, 498 and 500. The key switches comprising the keyboard 492 are conventional switches for providing manual input entry for the densitometer apparatus 410.

As illustrated in FIG. 9, the actual visual display device 490 and keyboard 492 are positioned on an upper printed circuit (PC) board assembly 502. The upper board assembly 502 includes an aperture 504 through which an optics assembly 506 can be mounted and secured to the previously described optics assembly holder 474 located on the housing assembly 424. As further illustrated in FIG. 9, the upper PC board assembly 502 can be suitably mounted to the housing assembly 424 by means of screws 508 or other suitable connecting means.

As illustrated in FIG. 10, the optics assembly 506 comprises a lamp assembly 510 adapted to secure and hold a suitable and conventional light source lamp 512. The lamp assembly 510 is secured within a lamp housing 514 by means of a conventional screw 516 and washer assembly 518. The components comprising the lamp assembly 510 and lamp housing 514 are relatively conventional in design with respect to known densitometer apparatus. The lamp assembly 510 includes a lamp printed circuit board 520 on which appropriate circuitry (as subsequently described herein) associated with the light source lamp 512 can be located.

As further illustrated in FIG. 9, the densitometer apparatus 410 comprises a lower optics assembly 522 which may better be characterized as a lower PC board assembly. As will be described in subsequent paragraphs herein, the lower PC board assembly 522 comprises circuitry associated with transmission density measurements by the apparatus 410. As shown in FIG. 9, the lower PC board assembly comprises a series of pins 524 comprising conventional elements for interconnecting the circuitry of the PC board assembly 522 to other circuitry associated with the apparatus. In addition, the lower PC board assembly 522 includes a pin connector 526 specifically adapted for providing circuit connections with the motor assembly 426. In addition, the PC board assembly 522 can also comprise an additional pin connector 528 suitable for connecting the circuitry of the lower PC board assembly 522 to power from rechargeable batteries.

As still further shown in FIG. 9, the densitometer apparatus 410 can comprise a battery holder assembly 530 adapted to receive a series of six rechargeable batteries 532. The rechargeable batteries 532 provide a means for operation of the density monitor apparatus 410 without requiring any type of utility or external power. However, it should be emphasized that such a battery arrangement is purely optional, and does not comprise any of the basic and principal novel concepts of the invention.

For purposes of providing installation and appropriate positioning of the battery holder assembly 530, the apparatus 410 can further comprise a battery pad 534 positioned below the lower set of the rechargeable batteries 532. In addition, if desired, the apparatus 410 can further comprise a back label 535 and serial number label 536. In addition, located on the top cover 412, and positioned to be received over the display 490 and keyboard 492 can be a nameplate 538. Finally, a label 540 or other suitable identification means can further be positioned on the top cover 412.

Returning again to FIG. 7, the top cover 412 further comprises, in one side surface 418, an aperture 542 with an electrical receptacle 544 located within but spaced slightly apart from the aperture 542. The receptacle 544 comprises an input/output (I/O) port for a conventional RS 232 interface for purposes of providing a means for inputting data to and outputting data from the densitometer apparatus 410. The concept of providing I/O data through the RS 232 interface will be described in subsequent paragraphs herein.

In addition to the aperture 542, the densitometer apparatus 410 also comprises a second aperture 546 positioned on a side surface 422 of the bottom cover 414. Positioned within the aperture 546, but not specifically shown in FIG. 7, is an input receptacle for purposes of providing charger input for the batteries 532. Preferably, if the densitometer apparatus 410 comprises the batteries 532, the batteries 532 are conventional rechargeable batteries. The aperture 546, in combination with appropriate and conventional circuitry, can comprise a means for recharging the batteries 532 as necessary.

Figure 3:
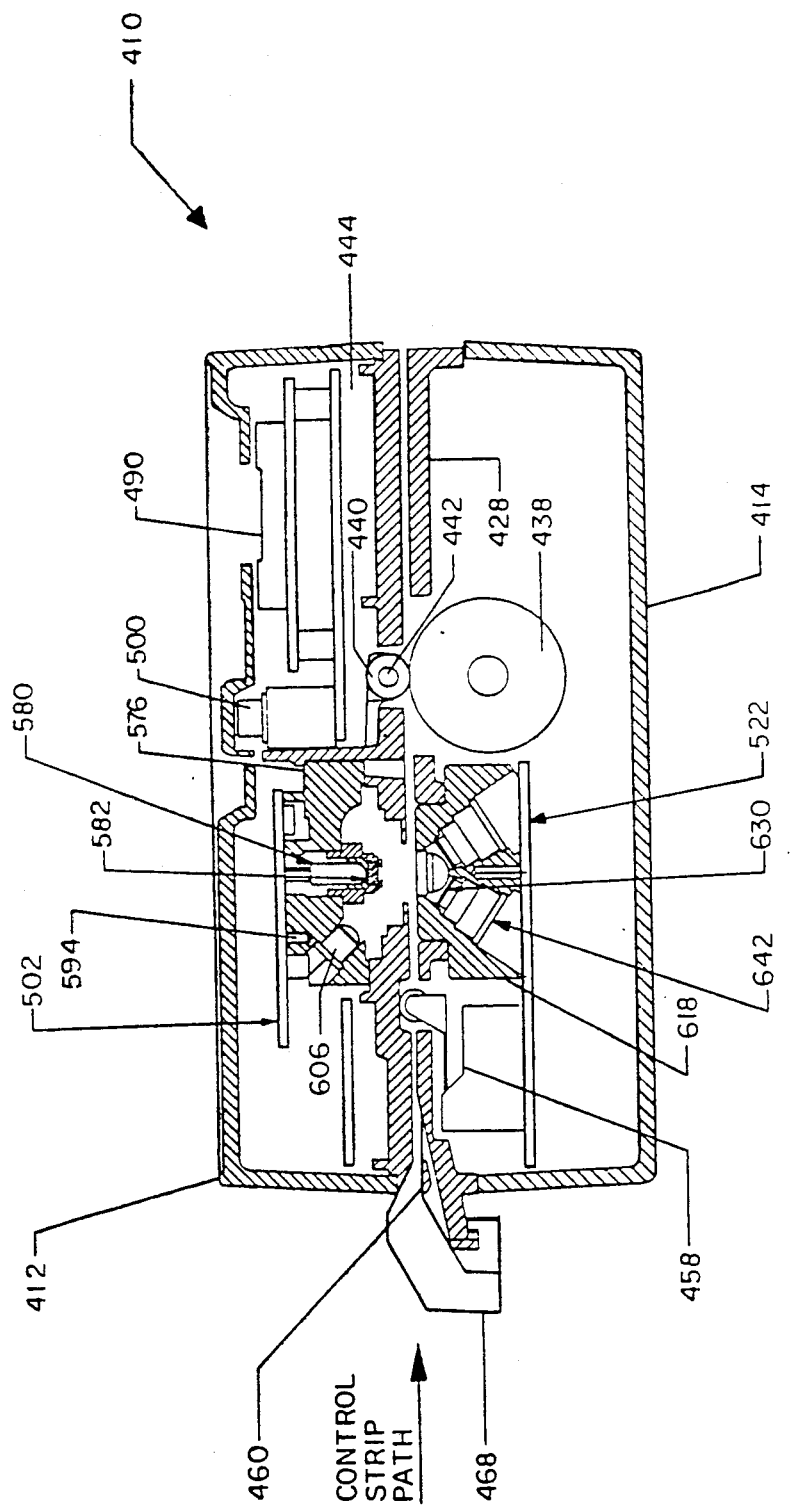
FIG. 3 is a cross sectional diagram of a densitometer apparatus in accordance with the invention, illustrating the structural configuration of various elements of the apparatus.
Figure 4:
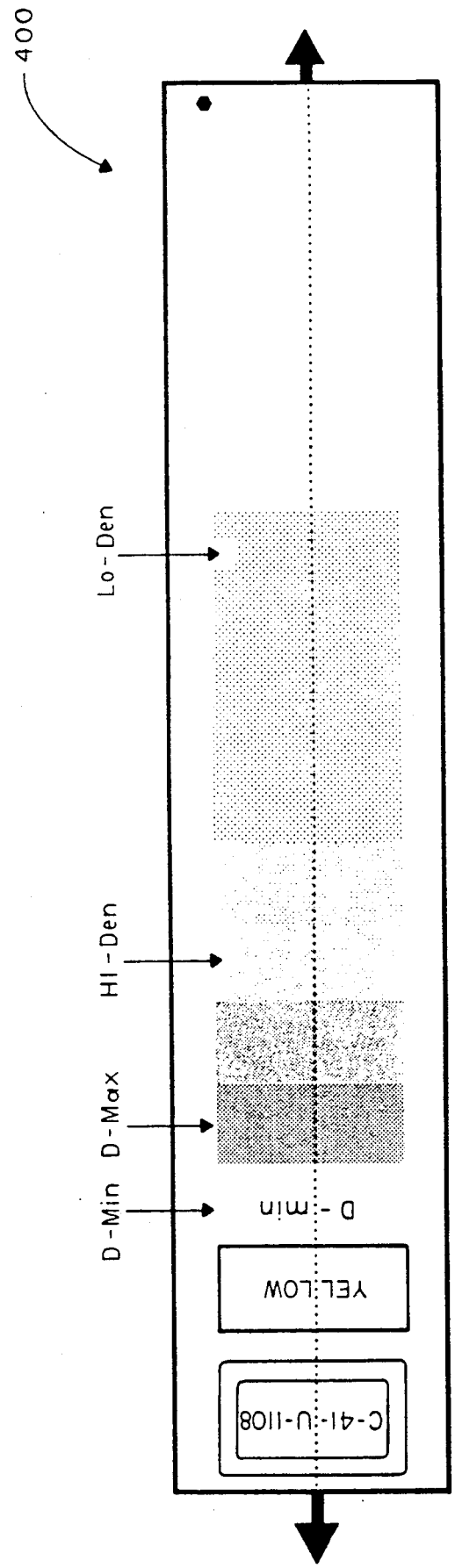
FIG. 4 is an illustrative embodiment of a control strip which can be utilized in accordance with the invention.
Figure 5:
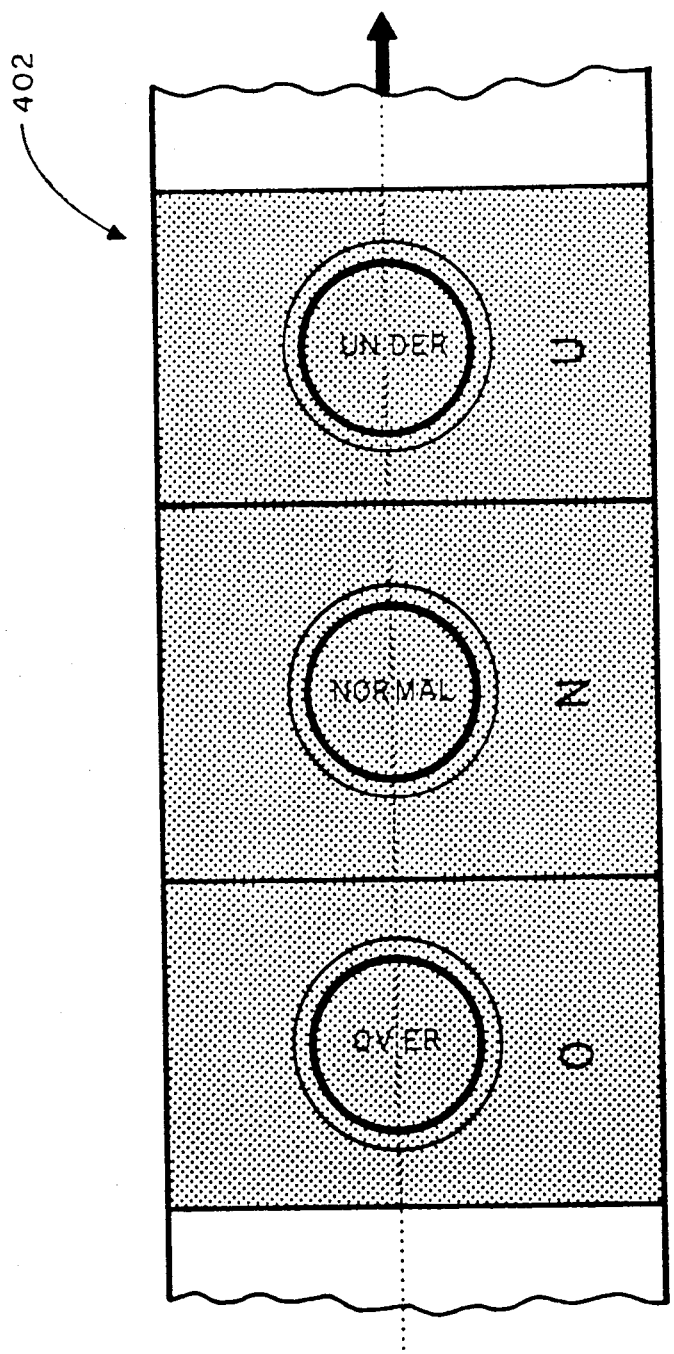
FIG. 5 is an illustrative embodiment of a print balance control strip which can be utilized in accordance with the invention.
Figure 6:
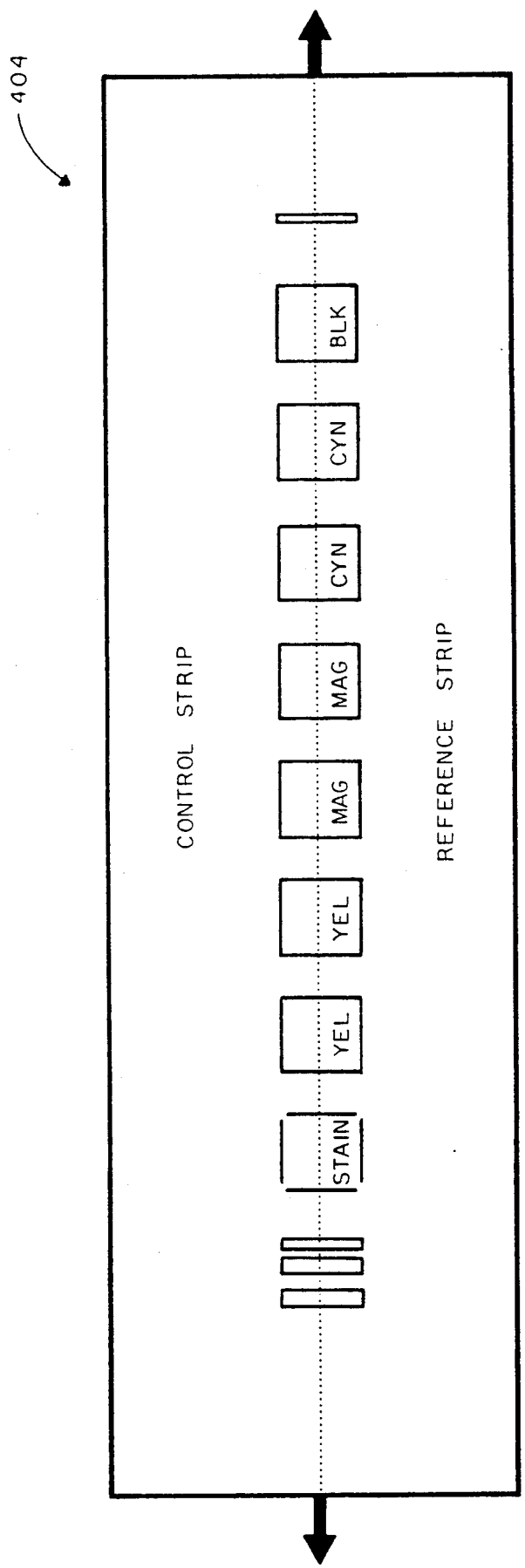
FIG. 6 is an illustrative embodiment of a further control strip which can be utilized in accordance with the invention.

As further illustrated in FIG. 7, the recessed portion 454 of the housing assembly 424 can include a "diamond" or other appropriate indicia 548 for purposes of indicating the center of the path for color density measurements of the control strips. In addition, and as previously referenced with respect to the description of FIG. 8, the forward edge 452 of the bottom housing 428 of the housing assembly 424 can include numerical indicia 550 centered with respect to the diamond indicia 548 and extending lengthwise across the forward edge 452. The numerical indicia 550 provide a means for indicating appropriate settings of the left and right film guides 468 and 470, respectively. As further shown in FIG. 7, the left and right film guides 468, 470 are conventional guides which are located at the forward edge 452 of the bottom housing 428 of housing 424. As shown in FIG. 8, the guides 468, 470 include elongated portions 552 which extend inwardly above the bottom housing 428 of housing assembly 424 and below the top housing 444. Each of the film guides 468, 470 is manually adjustable by the operator and comprise a means for guiding and controlling guidance of a control strip into the densitometer apparatus 410. FIG. 3 is a cross sectional view illustrating the configuration of the structural and circuit elements of densitometer apparatus 410 described herein.

Figure 11:
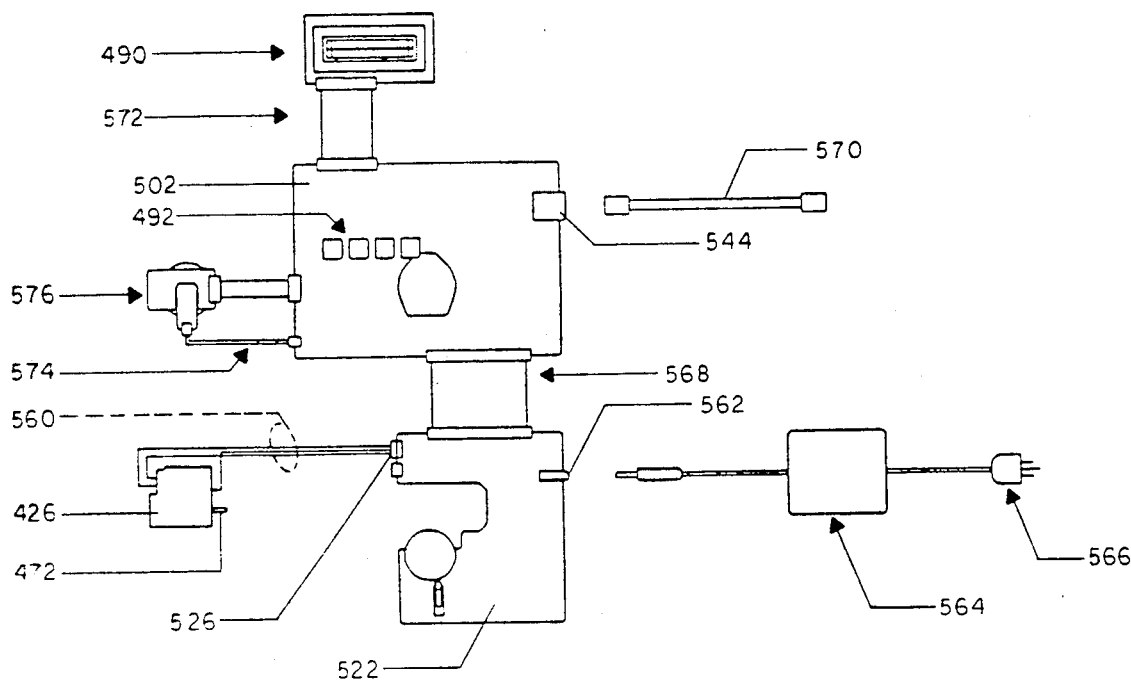
FIG. 11 is a partially schematic block diagram illustrating circuit interconnection of various elements of the densitometer apparatus in accordance with the invention.

The circuitry associated with the densitometer apparatus 410 will now be described with respect to FIGS. 11 through 23. FIG. 11 illustrates a block diagram in simplified format showing the interconnection of various elements of the circuitry of densitometer apparatus 410. Referring specifically to FIG. 11, the motor assembly 426 is illustrated as comprising a set of electrically conductive leads 560 interconnected through the connector element 526 to circuitry associated with the bottom PC board assembly 522. Correspondingly, and as previously described with respect to FIG. 7, a connector element 562 is also provided on the bottom PC board assembly 522 and is adapted to interconnect with any of numerous conventional AC/DC adaptor devices 564. Such an AC/DC adaptor device 564 is utilized in conjunction with a conventional electrical plug 566 to provide utility and external power to the apparatus 410, while converting the conventional utility AC power to an appropriate DC voltage level. As will be described in greater detail in subsequent paragraphs herein, the bottom PC board assembly 522 also includes the appropriate optics assembly for purposes of measuring transmission densities of film materials such as negatives.

The bottom PC board assembly 522 is electrically connected through appropriate connector leads 568 to the upper PC board assembly 502. As previously described with respect to FIG. 7, the upper PC board assembly 502 includes a connection receptacle 544 which is adapted to interconnect with a modular interface cable 570 for purposes of providing an I/O RS 232 interface to peripheral devices, such as a printer or the like. As further shown in FIG. 11, the upper PC board assembly 502 also comprises appropriate interconnections to the keyboard switches 492. In addition, through appropriate conductive connectors 572, the upper PC board assembly 502 is electrically connected to the display device 490.

As will be described in greater detail in subsequent paragraphs herein, the densitometer apparatus 410 also comprises a reflection optics assembly 576 for purposes of measuring reflectance densities of opaque materials such as photographic paper and the like. As illustrated in FIG. 11, an interconnection is provided through connector lead sets 574 to the reflection optics assembly 576.

Figure 12:
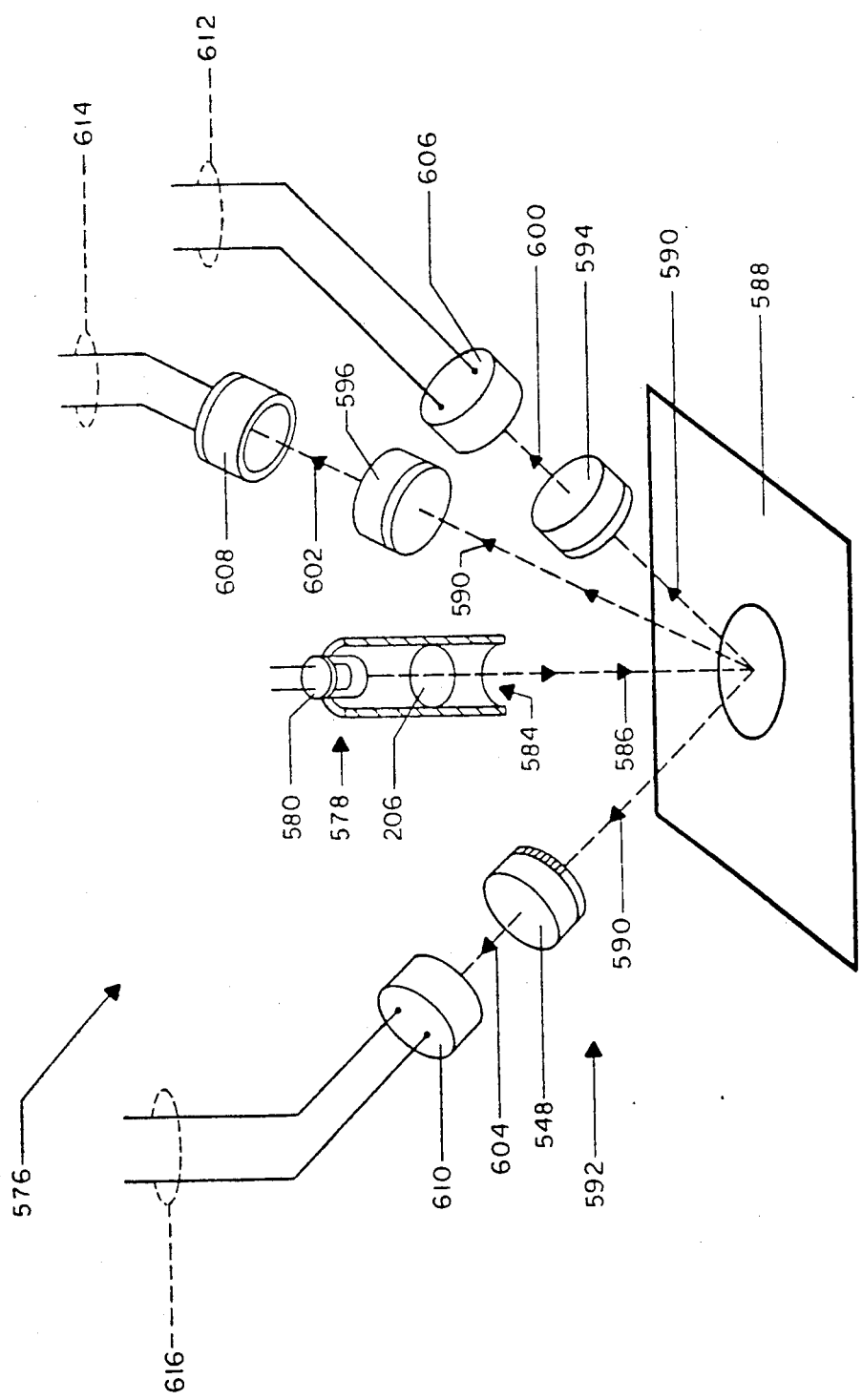
FIG. 12 is an illustration of the reflection optics assembly of the densitometer apparatus shown in FIG. 7.

In accordance with the invention, the densitometer apparatus 410 includes appropriate optics assemblies for measuring both transmission densities and reflection densities. FIG. 12 illustrates an exemplary reflection optics assembly 576 which can be utilized with the densitometer apparatus 410 in accordance with the invention. Referring specifically to FIG. 12, and the numerical references therein, the densitometer apparatus 410 includes a light source unit or a lamp assembly 578 having a source light 580. Various standards have been developed for densitometer light source illuminants for optical density measurements in the field of photography. For example, densitometer standards have previously been described in terms of a tungsten lamp providing an influx from a lamp operating at a Planckian distribution of 3000K. Other suggested standards have been developed by ANSI and the International Organization for Standardization ("ISO"). These source light densitometry standards are typically defined in terms of the spectral energy distribution of the illuminant. The source light 580 preferably conforms to an appropriate standard and can, for example, comprise a filament bulb meeting a standard conventionally known in the industry as 2856K ANSI. As previously described, power for the source light 580 and other elements of the densitometer apparatus 410 can be provided by means of conventional rechargeable batteries or, alternatively, interconnection to AC utility power.

The source light 580 projects light through a collimating lens 582 which serves to focus the electromagnetic radiation form the source light 580 into a narrow collimated beam of light rays. Various types of conventional and well-known collimating lenses can be employed. The light rays transmitted through the collimating lens 582 project through an aperture 584. The dimensions of the aperture 584 will determine the size of the irradiated area of the control strip. Various standards have been defined for preferable sizes of the irradiated area. Ideally, the aperture 584 is of a size such that the irradiance is uniform over the entire irradiated area. However, in any physically realizable densitometer arrangement, such uniform irradiance cannot be achieved. Current standards suggest that the size of the irradiated area should be such that irradiance measured at any point within the area is at least 90% of the maximum value. In addition, however, aperture size is typically limited to the size of color bar areas to be measured, and is also sized so as to reduce stray light.

The light rays emerging from the aperture 584 (illustrated as rays 586 in FIG. 12) are projected onto the irradiated area surface of the control strip 588 under test. The control strip 588 may be a print balance strip or, alternatively, photographic paper or the like.

As the light rays 586 are projected onto the control strip 588, electromagnetic radiation shown as light rays 590 will be reflected from the control strip 588. As previously described in the section entitled "Background of the Invention", it is necessary to obtain quantitative measurements of this reflected light for purposes of determining the relative proportions of the light reflected from various object samples. As also previously described, it is substantially impossible to measure all of the light reflected from the control strip 588. Accordingly, standard detection configurations have been developed, whereby reflected light is detected at a specific angle relative to the illumination light rays 586 projected normal to the plane of the control strip 588. More specifically, standards have been developed for detection of reflected light rays at an angle of 45° to the normal direction of the light rays 586. This angle of 45° has become a standard for reflectance measurement and is considered desirable in that this configuration will tend to maximize the density range of the measurements. In addition, however, the 45° differential also represents somewhat of a relatively normal viewing configuration of a human observer (i.e. illumination at a 45° angle from the viewer's line of sight).

For purposes of providing light detection, a spectral filter apparatus 592 is provided. The filter apparatus 592 can include a series of filters 594, 596 and 598. The filters 594, 596 and 598 are employed for purposes of discriminating the cyan, magenta and yellow spectral responses, respectively. That is, each of the filters will tend to absorb light energy at frequencies outside of the bandwidth representative of the particular color hue of the filter. For example, the cyan filter 594 will tend to absorb all light rays, except for those within the spectral bandwidth corresponding to a red hue. By detecting reflected light rays only within a particular color hue bandwidth, and obtaining an optical density measurement with respect to the same, a "figure of merit" can be obtained with respect to the quality and color measurement of the control strip patch associated with that particular color hue.

Figure 1:
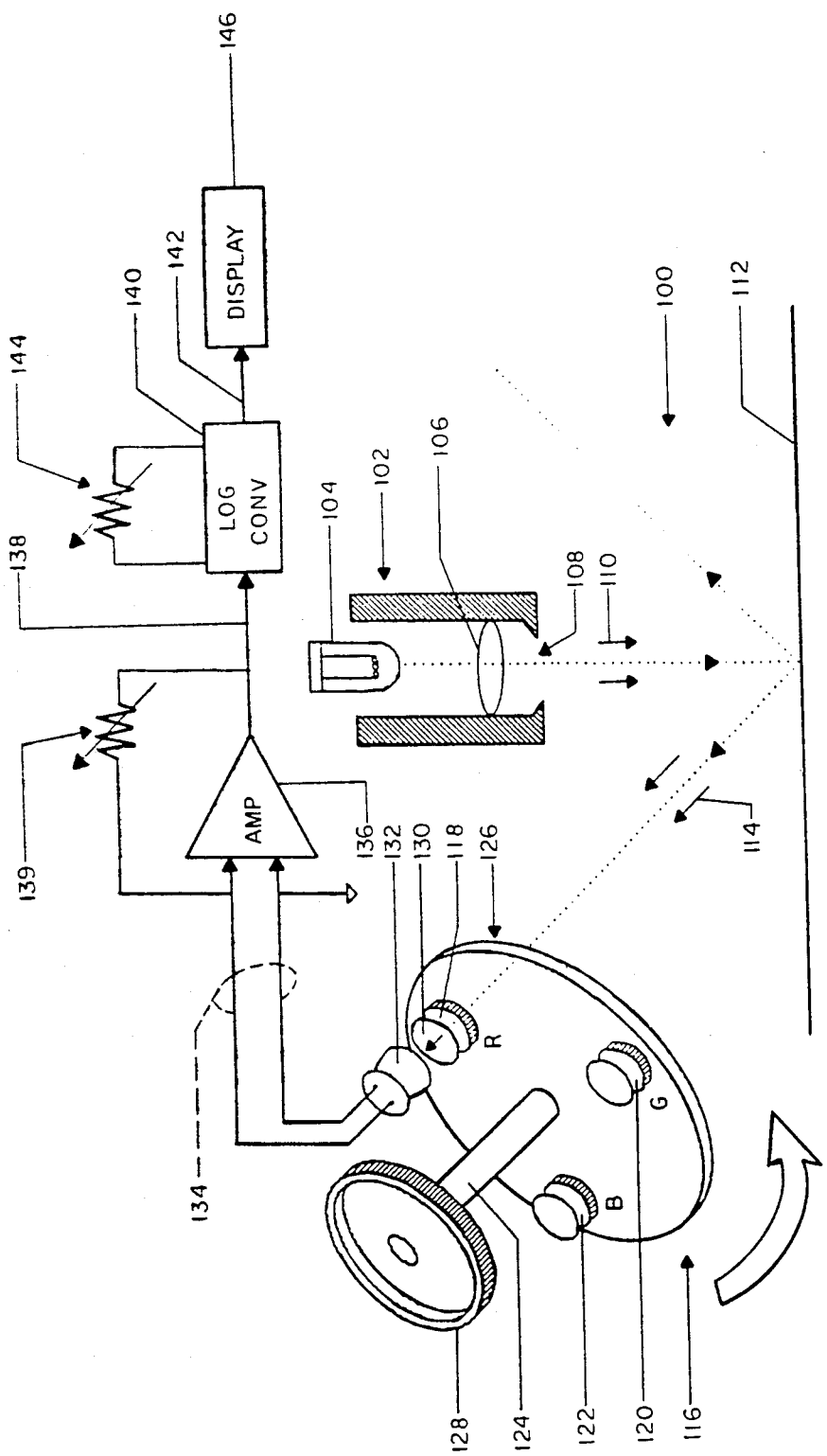
FIG. 1 is a prior art illustration of a partially schematic block diagram of a densitometer apparatus for measuring color densities.
Figure 2:
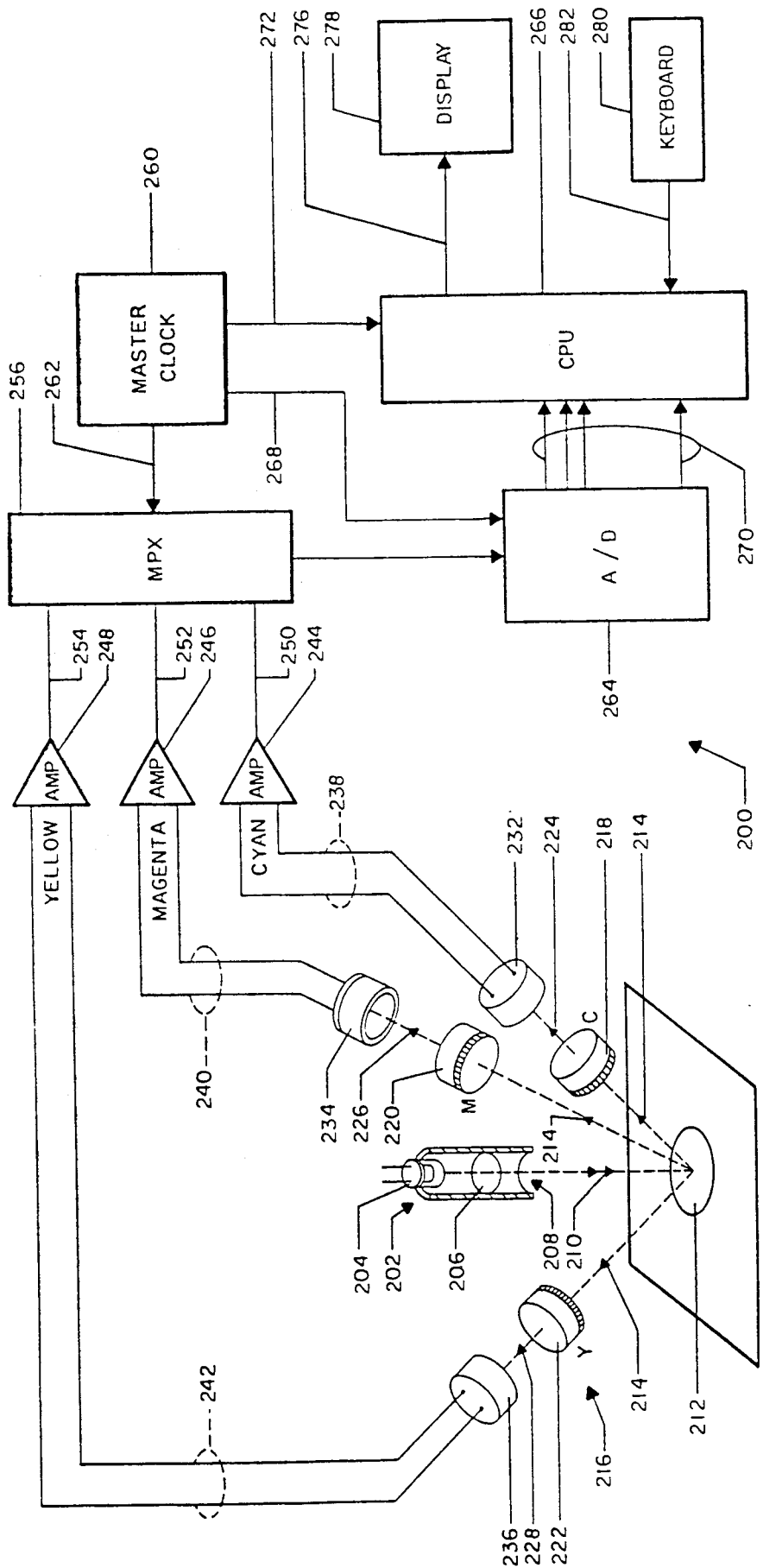
FIG. 2 is a prior art partially schematic block diagram of a further densitometer apparatus for measuring color densities.

It is apparent from the foregoing that the actual quantitative measurement of color density for reflectance is dependent in substantial part on the spectral transmittance characteristics of the filters. Accordingly, various well known standards have been developed with respect to spectral characteristics of densitometer filters. Standards were previously described with respect to the prior art densitometer apparatus 100 illustrated in FIG. 1. For example, Status A filters can be employed.

Although the filters 594, 596 and 598 are illustrated in the embodiment shown in FIG. 12 as the cyan, magenta and yellow color shades, other color shades can clearly be employed. These particular shades are considered somewhat preferable in view of their relative permanence and because they comprise the preferred shades for use in reflection densitometer calibration. However, it is apparent that different shades of red, blue and green, as well as entirely different colors, can be utilized with the densitometer apparatus 410 without departing from the novel concepts of the invention.

The spectral filters 594, 596 and 598 may not only comprise various shades of color, but can also be of any several specific types of spectral response filters. For example, the filters can comprise a series of conventional Wratten gelatin filters and infrared glass. However, various other types of filter arrangements can also be employed.

The spectral filters 594, 596 and 598 are preferably positioned at a 45° angle relative to the normal direction from the plane of the control strip 588 under test. However, unlike the densitometer configuration 100 previously described, each of the filters 594, 596 and 598 are maintained stationary and are utilized to simultaneously receive light rays reflected from the control strip 588 under test. Accordingly, it is unnecessary for the user to manually rotate or otherwise sequentially move spectral filters into receptive positions. Various types of densitometer structural configurations can be utilized to appropriately position each of the filters at the preferable 45° angular position.

As further shown in FIG. 12, the portion of the reflected light rays 590 which pass through the filters 594, 596 and 598 (shown as light rays 600, 602 and 604, respectively) impinge on receptor surfaces of photovoltaic sensor cells. The sensor cells are illustrated in FIG. 12 as sensors 606, 608 and 610 associated with the spectral filters 600, 602 and 604, respectively The sensors 606, 608 and 610 can comprise conventional photoelectric elements adapted to detect the light rays eminating through the corresponding spectral filters. The sensors are further adapted to generate electrical currents having magnitudes proportional to the intensities of the sensed light rays. As illustrated in FIG. 12, the electrical current generated by the cyan sensor 606 in response to the detection of light rays projecting through the filter 608 is generated on line pair 612. Correspondingly, the electrical current generated by the magenta sensor 608 is applied to the line pair 614, while the electrical current generated by the yellow sensor 610 is applied as output current on line pair 616. Photoelectric elements suitable for use as sensors 606, 608 and 610 are well known in the art, and various types of commercially available sensors can be employed.

The magnitude of the electrical current on each of the respective line pairs will be proportional to the intensity of the reflected light rays which are transmitted through the corresponding spectral filter. These light rays will have a spectral distribution corresponding in part to the product of the spectral reflectance curve of the control strip sample 588 under test, and the spectral response curve of the corresponding filter. Accordingly, for a particular color shade represented by the spectral response curve of the filter, the magnitude of the electrical current represents a quantitative measurement of the proportion of reflectance of the control strip sample 588 within the frequency spectrum of the color shade.

Figure 13:
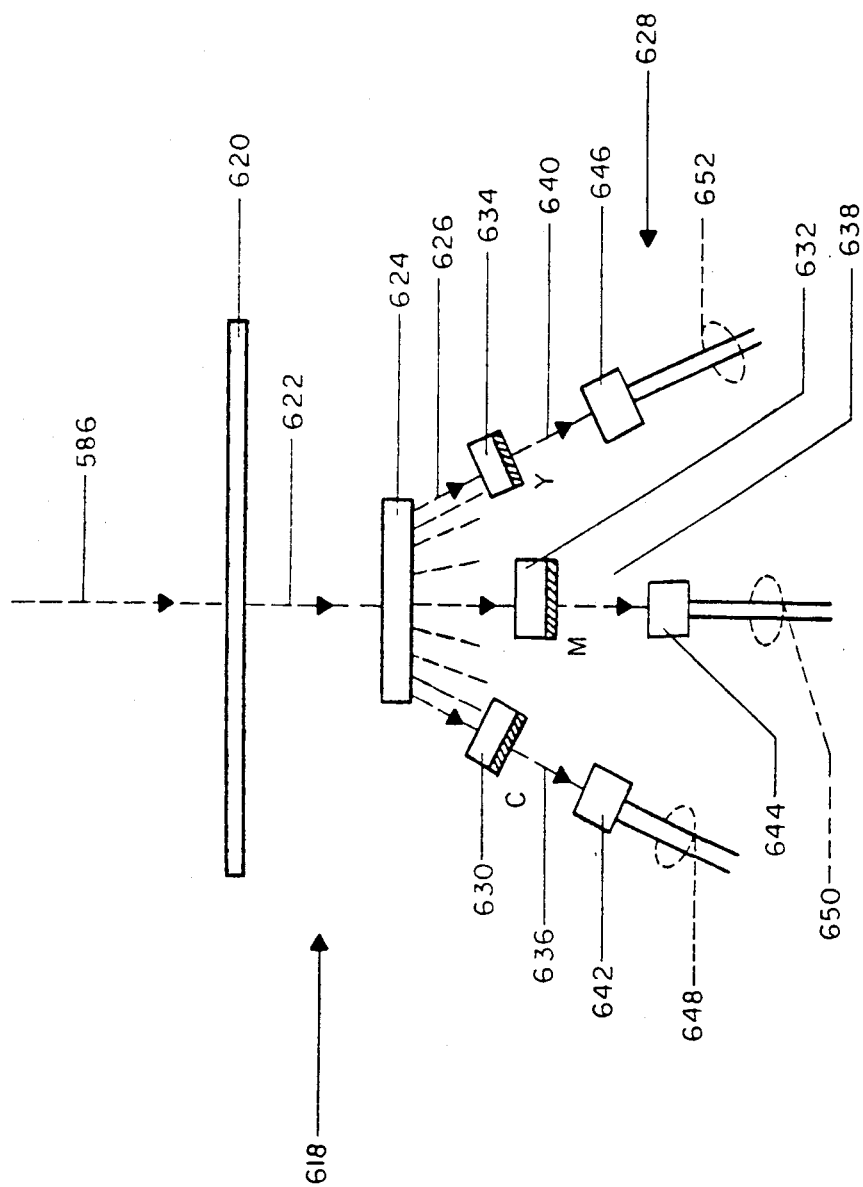
FIG. 13 is a partially schematic diagram of the transmission optics assembly of the densitometer apparatus shown in FIG. 7.

In accordance with the invention, the densitometer apparatus 410 includes not only a reflection optics assembly 576 as previously described with respect to FIG. 12, but further includes a transmission optics assembly 618 depicted in simplified schematic form in FIG. 13. As previously described with respect to FIGS. 7 through 11, the transmission optics assembly 618 is mounted on the lower PC board assembly 522. The exact method and structure associated with the mounting of the transmission optics assembly 618 will be apparent to one skilled in the art of optics and densitometer design, and will not be described in detail herein. FIG. 3 substantially illustrates the structural positioning.

Referring specifically to FIG. 13, a film control strip 620 for which transmission density is to be measured is positioned so that the light rays 586 from the source light 580 (previously described with respect to FIG. 12) are projected from above the film control strip 620 onto the irradiated area surface of the strip 620. The film control strip 620 may be any of numerous types of materials for which the transmission density will provide an indication of the photographic quality of the associated photographic process. For example, the control strip 620 can be a film negative.

As the light rays 586 are projected onto the film control strip 620, electromagnetic radiation shown as light rays 622 will be transmitted through the control strip 620. For purposes of determining the relative proportions of the light transmitted through various object samples, it is necessary to obtain quantitative measurements of this transmitted light. However, it is substantially impossible to measure all of the light transmitted through the control strip 620. Accordingly, the transmitted light rays 622 are projected through a diffuser element 624 which causes the light rays to be substantially uniformly diffused. The diffuser element 624 is a relatively common and well known optical device, and can be characterized as an "opal." The diffused light rays transmitted through the diffuser element 624 are shown in FIG. 13 as light rays 626.

For purposes of providing light detection, a spectral filter apparatus 628 is provided. The filter apparatus 628, similar to the filter apparatus 592 described with respect to FIG. 12, comprises a series of three filters 630, 632 and 634. The filters 630, 632 and 634 are employed for purposes of discriminating the red, blue and green spectral responses (cyan, magenta and yellow), respectively. That is, each of the filters will tend to absorb light energy at frequencies outside of the bandwidth representative of the particular color hue of the filter. By detecting reflected light rays only within a particular color hue bandwidth, and obtaining an optical density measurement with respect to the same, a "figure of merit" can be obtained with respect to the quality of the object sample coloring associated with that particular color hue.

The spectral filters 630, 632 and 634 can be positioned at any of a number of desired angles relative to the plane of the opal 624 and the control strip 620. Although FIG. 13 shows the filters of the filter apparatus 628 in a two dimensional elevation view, the filters of the apparatus 628 will actually be angled in a manner similar to the configuration shown in the perspective view of FIG. 12 with respect to the reflection filters. Further, although the filters 630, 632 and 634 are illustrated in the embodiment shown in FIG. 13 as the red, blue and green color shades, other color shades can clearly be employed.

It is apparent from the foregoing that the actual quantitative measurement of color density of transmittance is dependent in substantial part on the spectral transmittance characteristics of the filters. Accordingly, various well-known standards have been developed with respect to spectral characteristics of transmittance densitometer filters. For example, these filters can be filters commonly characterized as Status M filters. Standards associated with various types of filters were previously described with respect to the prior art densitometer apparatus 100 illustrated in FIG. 1.

Like the reflection filters previously described, the filters of the filter apparatus 628 are maintained stationary and utilized to simultaneously receive the light rays 626 transmitted through the control strip 620. Accordingly, it is unnecessary for the user to manually rotate or otherwise sequentially move spectral transmittance filters into receptive positions.

As further shown in FIG. 13, the portion of the transmitted light rays 626 which pass through the filters 630, 632 and 634 (shown as light rays 636, 638 and 640, respectively) impinge on receptor surfaces of photovoltaic sensor cells. The sensor cells are illustrated in FIG. 13 as sensors 642, 644 and 646 associated with the spectral filters 630, 632 and 634, respectively. The sensors 642, 644 and 646 can comprise conventional photoelectric elements adapted to detect the light rays eminating through the corresponding spectral filters. The sensors are further adapted to generate electrical currents having magnitudes proportional to the intensities of the sensed light rays. As illustrated in FIG. 13, the electrical current generated by the red sensor 642 in response to the detection of light rays projecting through the filter 630 is generated on line pair 648. Correspondingly, the electrical current generated by the blue sensor 644 is applied to the line pair 650, while the electrical current generated by the green sensor 646 is applied as output current on line 652. Photoelectric elements suitable for use as sensors 642, 644 and 646 are well known in the art, and various types of commercially available sensors can be employed.

The magnitude of the electrical current on each of the respective line pairs will be proportional to the intensity of the reflected light rays which are transmitted through the corresponding spectral filter. These light rays will have a spectral distribution corresponding in part to the product of the spectral transmittance curve of the control strip 620, and the spectral response curve of the corresponding filter. Accordingly, for a particular color shade represented by the spectral response curve of the filter, the magnitude of the electrical current represents a quantitative measurement of the proportion of transmittance of the control strip 620 within the frequency spectrum of the color shade.

Figure 14:
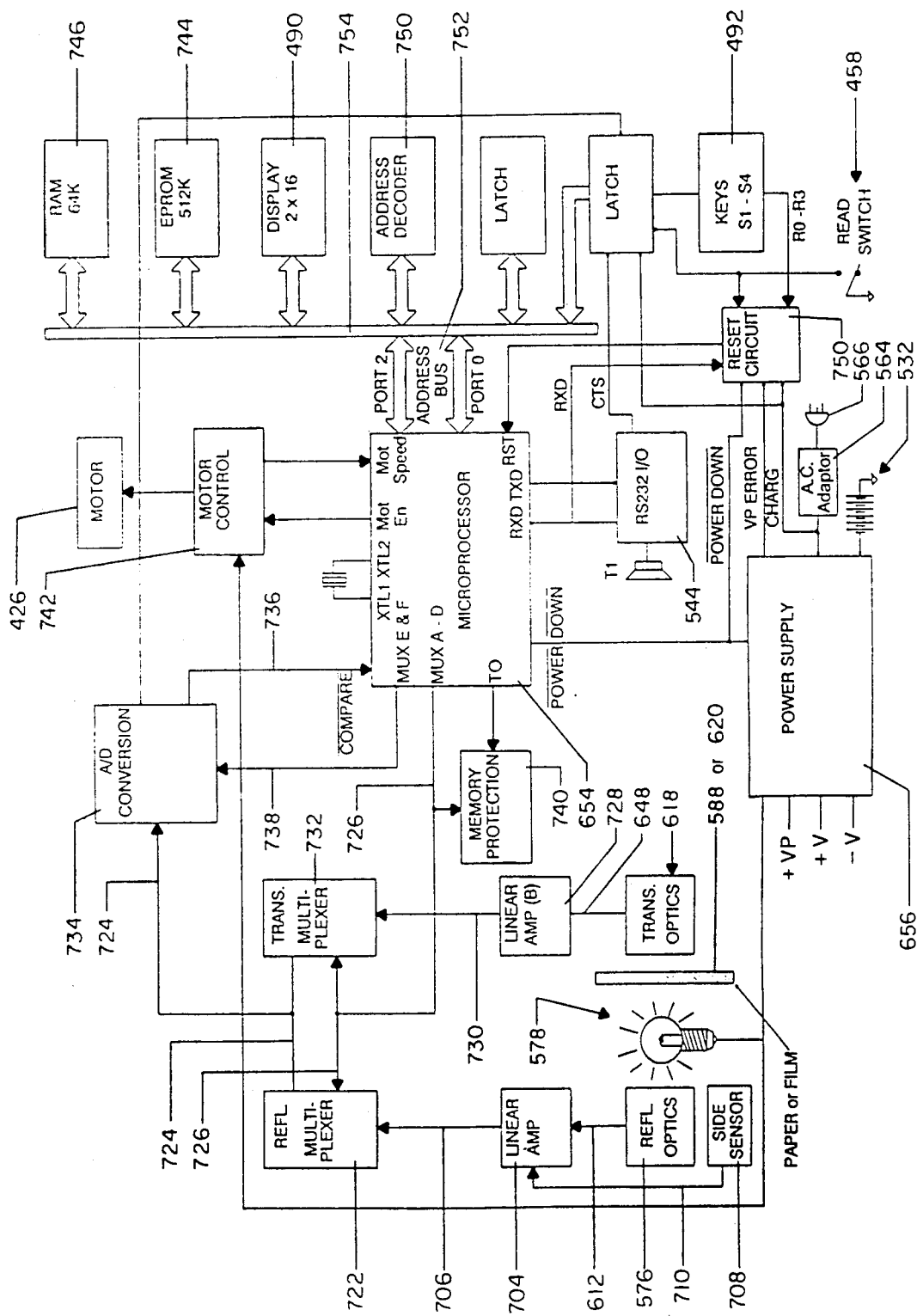
FIG. 14 is a partially schematic block diagram of circuit elements of the densitometer apparatus shown in FIG. 7.

A general simplified block diagram of the electronics of the densitometer apparatus 410 is illustrated in FIG. 14. As shown therein, and as previously described, the densitometer apparatus 410 includes a light source unit 578 utilized for measuring color densities of the control strip 588 or 620. If the control strip is control strip 588, the apparatus 410 is adapted to measure reflection density. If the control strip is strip 620, the apparatus 410 is adapted to measure transmittance density through the use of the transmittance optics assembly 618. For purposes of description, although the reflection optics assembly 576 and the transmission optics assembly 618 each comprise three spectral filters and photosensors, and three paths for determining the color densities of different color hues of the spectrum, the electronics associated with the same will be described only with respect to one path. Accordingly, as shown in FIG. 14, only the line pair 612 is shown as being interconnected to the reflection optics assembly 576. Correspondingly, only the line pair 648 is shown as being interconnected with the transmission optics assembly 618. However, other line pairs as previously described with respect to FIGS. 12 and 13 will be interconnected to each of the optics assemblies 576 and 618.

As further shown in FIG. 14, the densitometer apparatus 410 includes a conventional microprocessor 654 utilized for purposes of obtaining data representative of color densities of a control strip under test, and further utilized to control various activities associated with operation of the apparatus 410. For these purposes, the microprocessor 654 will comprise various control programs adapted to perform a number of functions associated with operation of the apparatus 410. These control programs will become apparent from the functions of the electronics and the general operation of the densitometer apparatus 410 as described in subsequent paragraphs herein. Accordingly, the actual control programs will not be described in detail. Further, various additional illustrations show numerous elements associated with the detailed circuitry of the densitometer apparatus 410. However, the specific structural configuration of such circuitry will be apparent to one skilled in the art of densitometer design from the general description of the block diagrams of the circuitry, and illustrations of the specific circuit elements. Accordingly, although illustrations of the drawings will show specific circuit detail, not all of this detail is described herein.

Figure 15:
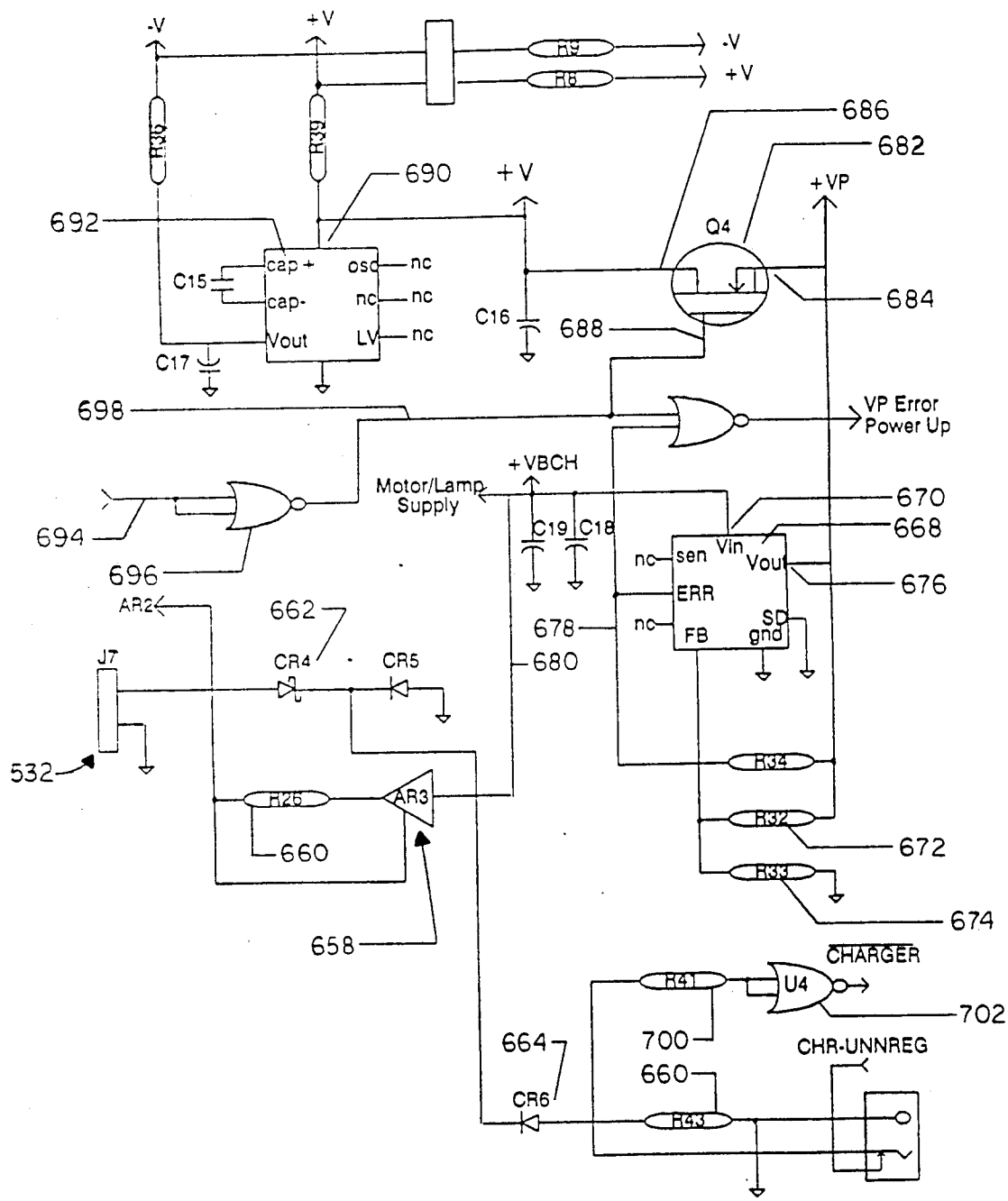
FIG. 15 is a circuit diagram of an illustrative embodiment of a power supply for use with the densitometer apparatus shown in FIG. 7.

Returning to FIG. 14, the densitometer apparatus 410 includes a relatively conventional power supply 656. The power supply 656 is adapted to provide power to various elements of the circuitry of apparatus 410. A more detailed diagram of the power supply 656 is shown in FIG. 15. The power supply 656 can actually obtain power from either the batteries 532 (illustrated in FIG. 14) or from utility power through the AC adaptor 564 also illustrated in FIG. 14. When the adaptor 564 is enabled, the batteries 532 will be charged with electrical current flowing through regulator 658 and resistor 660. Correspondingly, diode 662 and diode 664 will block current flow from either direction, depending upon which power source is currently being utilized. The resistor 666 is utilized to hold the input line low when the adaptor 564 is de-energized.

Voltage from the source is fed into a low power CMOS regulator 668 at pin 670. The output voltage is set up by resistors 672 and 674 which provide an output voltage on pin 676.

The capacitors 678 and 680 provide stabilization for the power supply circuitry. The output voltage, illustrated in FIG. 15 as voltage VP, is utilized for providing power to the microprocessor 654 and various other circuitry associated with the apparatus 410. This output voltage VP is applied as an input into the P channel field effect transistor 682 source pin 684, and a voltage +V is output on the drain pin 686 of transistor 682 when the gate pin 688 is held low during operation. The +V voltage is also utilized as a power supply for various circuitry of the densitometer apparatus 410.

The +V voltage is applied as an input into pin 690 of the voltage invertor circuit 692. The voltage invertor circuit 692 is utilized to output the voltage −V as illustrated in FIG. 15.

The power supply 656, in combination with the microprocessor 654, includes a feature whereby the microprocessor 654 is adapted to "power down" the circuitry after a predetermined period of time of nonuse. More specifically, the microprocessor 654 can generate a signal which is applied on line 694 and applied through NOR gate 696. The NOR gate 696 is adapted to apply a signal on line 698 which is further applied to the gate pin 688 of the field effect transistor 682. This signal will cause the +V voltage to "turn off", which prevents the voltage invertor 692 from outputting the −V voltage. In this manner, battery consumption is conserved during nonuse or storage of the unit. When one of the previously described key switches is depressed or a measurement taken, the signal on line 694 will change states so as to cause the +V and −V voltages to again be enabled. Also, it should be emphasized that when the adaptor 564 is enabled, this "power down" cycle is bypassed by applying a particular signal through resistor 700 as an input to the NOR gate 702. These signals will cause the power down cycle to by bypassed with the adaptor 564 enabled.

Returning to FIG. 14, when the reflection optics assembly 576 is utilized, an electrical current representative of the reflectance is applied on line pair 612 as an input signal to the conventional linear amplifier 704. The amplifier 704 is responsive to the current output of the associated sensor on line pair 612 to provide a means for converting low level output current from the respective sensor on the corresponding line pair 612 to a voltage level signal on the conductor 706. The voltage level of the signal on the conductor 706 is of a magnitude suitable for subsequent analog-to-digital (A/D) conversion functions. Such amplifiers are well known in the circuit design art and are commercially available with an appropriate volts per ampere conversion ratio, bandwidth and output voltage range. The magnitude of the output voltage on conductor 706 represents the intensity of reflected light rays transmitted through the corresponding spectral filter.

The densitometer apparatus 410 also includes a side sensor 708 which is utilized to compensate for changes in lamp intensity of the source light 578. Output from the side sensor 708 is applied to the linear amplifier circuit 704 on transmission line 710.

Figure 16:
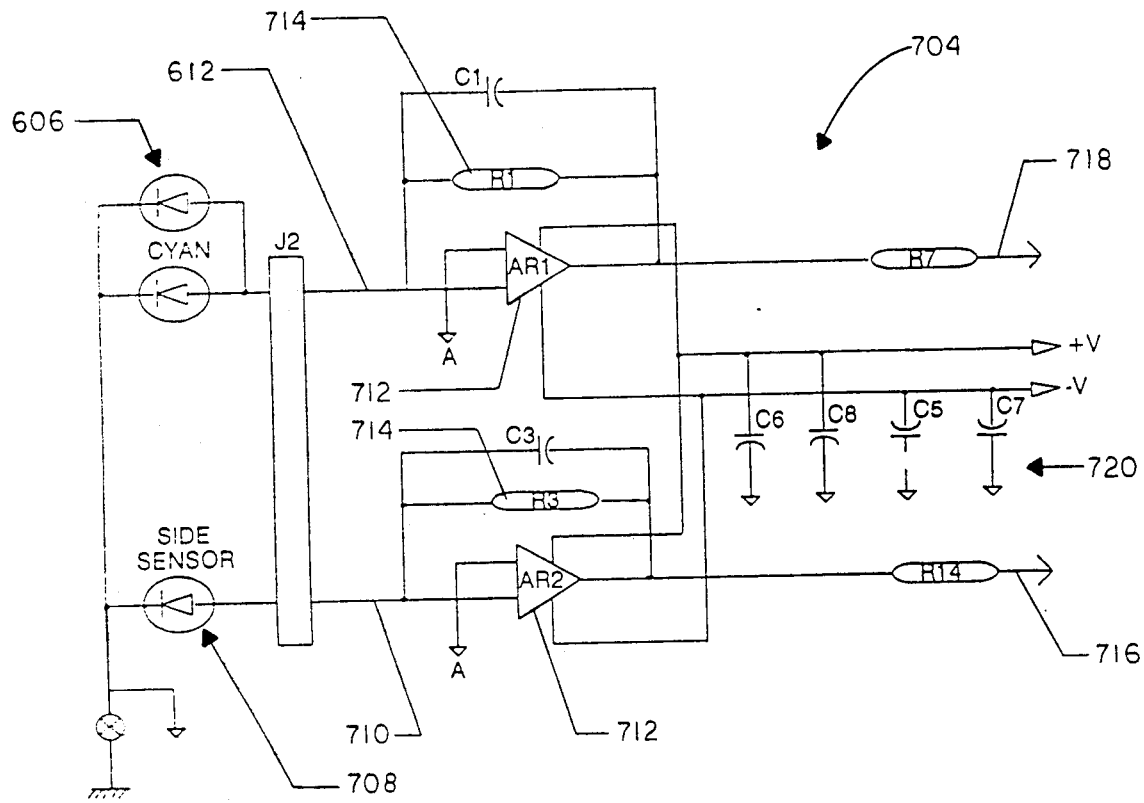
FIG. 16 is a circuit diagram of an illustrative embodiment of the reflection linear amplifier circuitry and side sensor circuitry for the densitometer apparatus.

A more detailed circuit diagram of the linear amplifier 704 is illustrated in FIG. 16. Referring specifically thereto, the sensor elements illustrated in FIG. 12 are shown in FIG. 16 as actually comprising two photodiodes wired in parallel. Each color channel, as previously described herein, will comprise one linear amplifier circuit. The side sensor 708 is illustrated as comprising a single photodiode. Each of the linear amplifier circuits 704 will generate a logarithmic output voltage from the linear input current. As illustrated in FIG. 16, the linear amplifier circuit 704 includes a pair of linear amplifier elements 712, with one of the linear amplifier elements 712 employed for the color channel and one employed for the side sensor. The feedback resistors 714 which are shown as being interconnected between the input and output of each linear amplifier element 712 are set up for appropriate gain for each color channel. Accordingly, relatively low and negative densities can be measured.

The linear amplifier element 712 associated with the side sensor 708 is utilized to detect whether the source light 578 is working, or if there is any variation in lamp intensity. When the source light 578 is enabled, the linear amplifier element 712 associated with the side sensor channel will output an appropriate current on line 716 which is applied to the multiplexer subsequently described herein. If the source light 578 has a relatively slight intensity variation, the output voltage of the linear amplifier element 712 associated with the side sensor channel will vary, allowing for the analog circuit to compensate for the source light intensity change.

The output voltage of the linear amplifier element 712 associated with the color channel is applied on transmission line 718 to the subsequently described multiplexer. It should also be noted that the voltage power supplied to the linear amplifier elements 712 is also fed to the capacitor bank 720 and the resistors, which operate as a low bypass filter to reduce ripple on the negative and positive voltages.

Each of the voltage signal outputs from the linear amplifier circuitry for each color channel are applied as input signals to a single conventional multiplexer 722. For example, as illustrated in FIG. 14, the output voltage from linear amplifier circuitry 704 is applied on the transmission line 706 as an input signal to the reflection multiplexer 722. It should be emphasized that although there are three linear amplifier circuits, one for each color channel, only a single reflection multiplexer 722 is provided. The multiplexer 722 operates so as to time multiplex the output signals from each of the linear amplifier circuits (including linear amplifier circuit 704) onto the conductive paths 724 and 726. Timing for operation of the reflection multiplexer 722 can be provided by means of clock signals from a conventional master clock. During an actual density measurement of a control strip, the densitometer apparatus 410 will utilize a segment of the resultant multiplexed signal which sequentially represents a voltage output signal from each of the linear amplifier circuits associated with different color channels.

Figure 17:
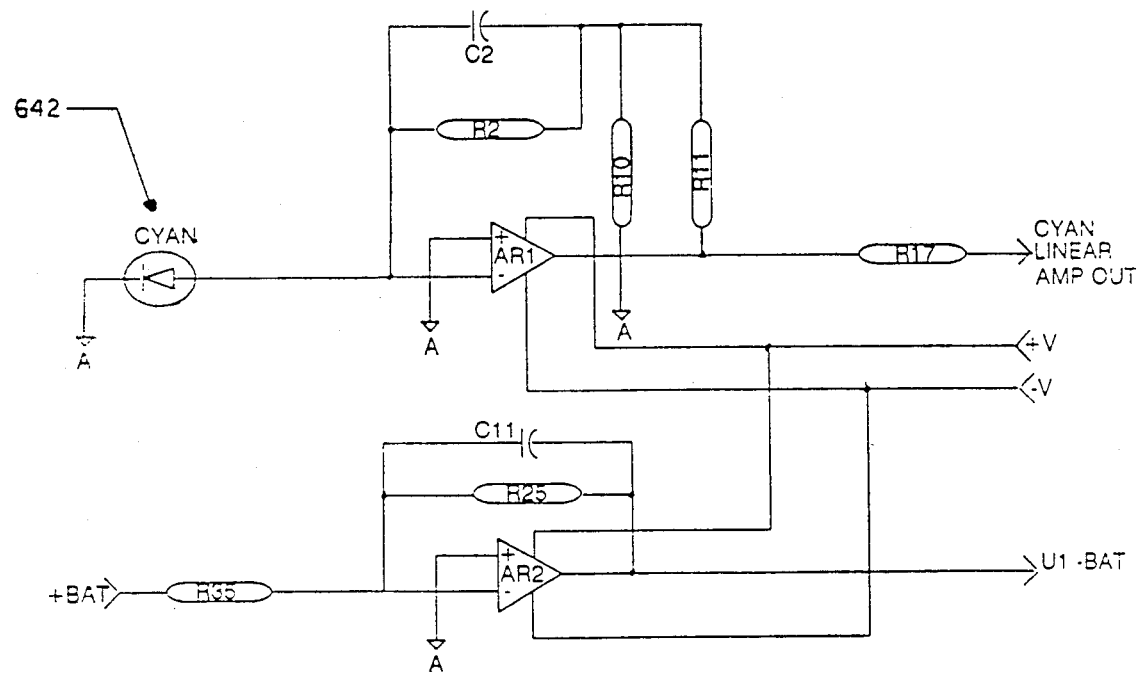
FIG. 17 is a circuit diagram of an illustrative embodiment of the transmission linear amplifier circuitry for the densitometer apparatus.

Correspondingly, as further illustrated in FIG. 14, the current output signal on line pair 648 from the transmission optics assembly 618 is applied to a linear amplifier circuit 728. A linear amplifier circuit 728 is provided for each of the color channels associated with the transmission optics assembly 618. The linear amplifier circuit 728 provides a means for converting low level output current from the respective sensor on the corresponding line pair 648 to a voltage level signal on the conductor 730. The voltage level of the signal on the conductor 730 is of a magnitude suitable for subsequent A/D conversion functions. A detailed circuit diagram of the linear amplifier circuitry 728 is illustrated in FIG. 17. The circuitry shown in FIG. 17 is relatively self explanatory and will not be described in detail herein. However, it should be emphasized that such linear amplifier circuitry is well known in the circuit design art and appropriate linear amplifiers are commercially available with an appropriate volts per ampere conversion ratio, bandwidth and output voltage range.

As further shown in FIG. 14, the voltage signal output from the linear amplifier circuitry 728 on conductive path 730 is applied as an input signal to a conventional transmission multiplexer 732. Like the reflection multiplexer 722, the transmission multiplexer 732 operates so as to time multiplex the output signals from each of the linear amplifier circuits associated with the transmission optics assembly 618. Again, timing for operation of the multiplexer 732 can be provided by means of clock signals from a master clock. During an actual transmission density measurement of a control strip, the densitometer apparatus 410 will utilize a segment of the resultant multiplexed signal which sequentially represents a voltage output signal from each of the linear amplifier circuits associated with the transmission optics assembly 618.

The resultant multiplexed signal from the transmission multiplexer 732 is applied as an output signal on the conductive path 724. The resultant multiplexed signal from either the reflection multiplexer 722 or the transmission multiplexer 732 is applied as an input signal to a conventional A/D converter 734. The A/D converter 734 comprises a means for converting the analog multiplexed signal on the conductive path 724 to a digital signal for purposes of subsequent processing by the microprocessor 654. The A/D converter 734 is preferably controlled by means of clock pulses applied from a conventional master clock.

As illustrated in FIG. 14, the digital output signals from the A/D converter 734 are applied as input signals on transmission line 736 to the microprocessor 654. Further, the microprocessor 654 is utilized to provide various control signals to the reflection multiplexer 722 and transmission multiplexer 732 (on transmission line 726). Still further, control signals are also applied from the microprocessor 654 to the A/D converter 734 by means of the transmission line 738. In addition to the foregoing elements, the densitometer apparatus 410 also comprises a memory protection circuit 740 which is further controlled in part by the microprocessor 654. The memory protection circuit 740 is conventional in design and comprises a well known arrangement for protecting the memory against power surges and power outages.

Figure 18:
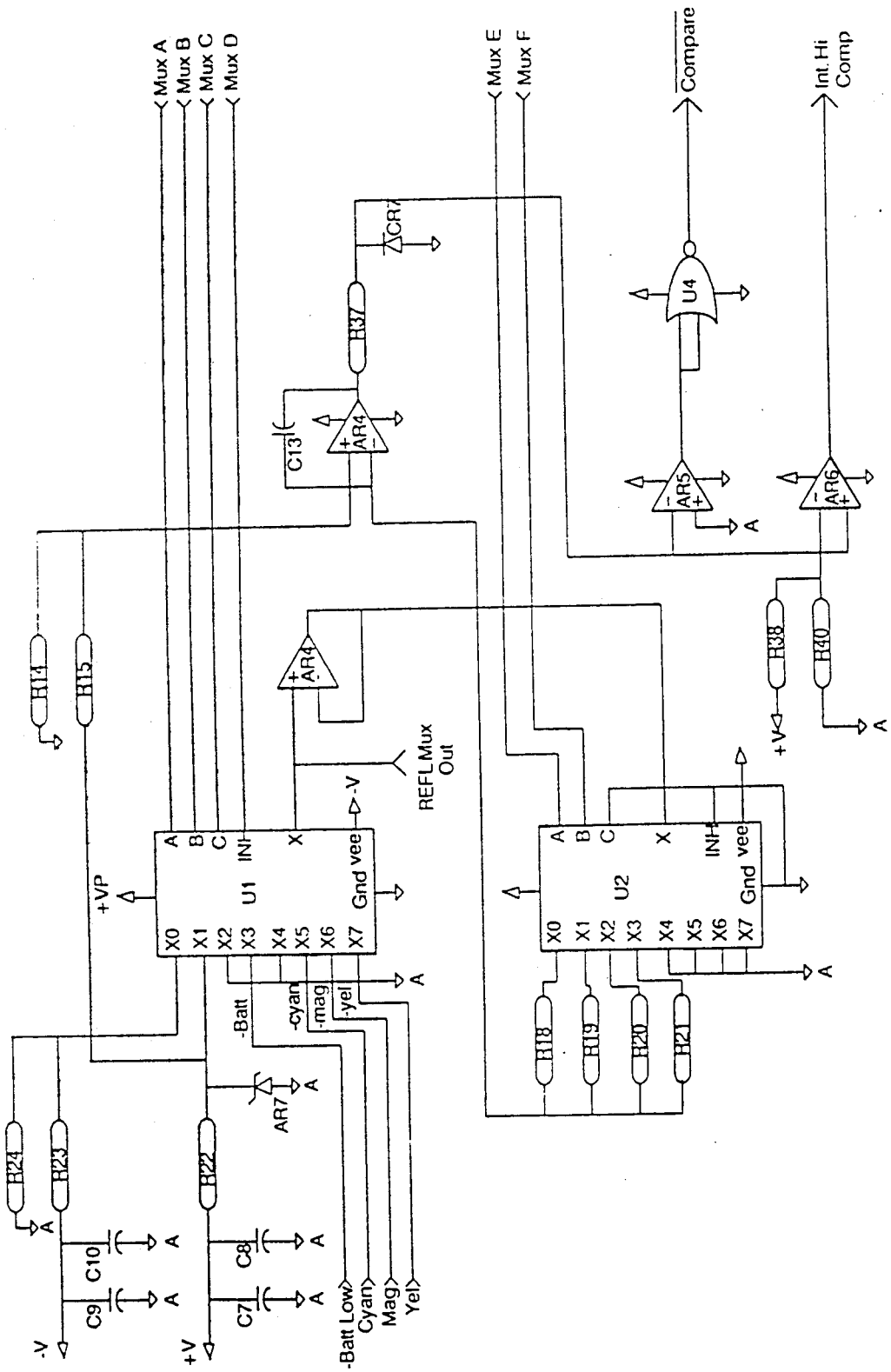
FIG. 18 is a circuit diagram of an illustrative embodiment of the transmission A/D conversion circuitry for the densitometer apparatus.
Figure 19:
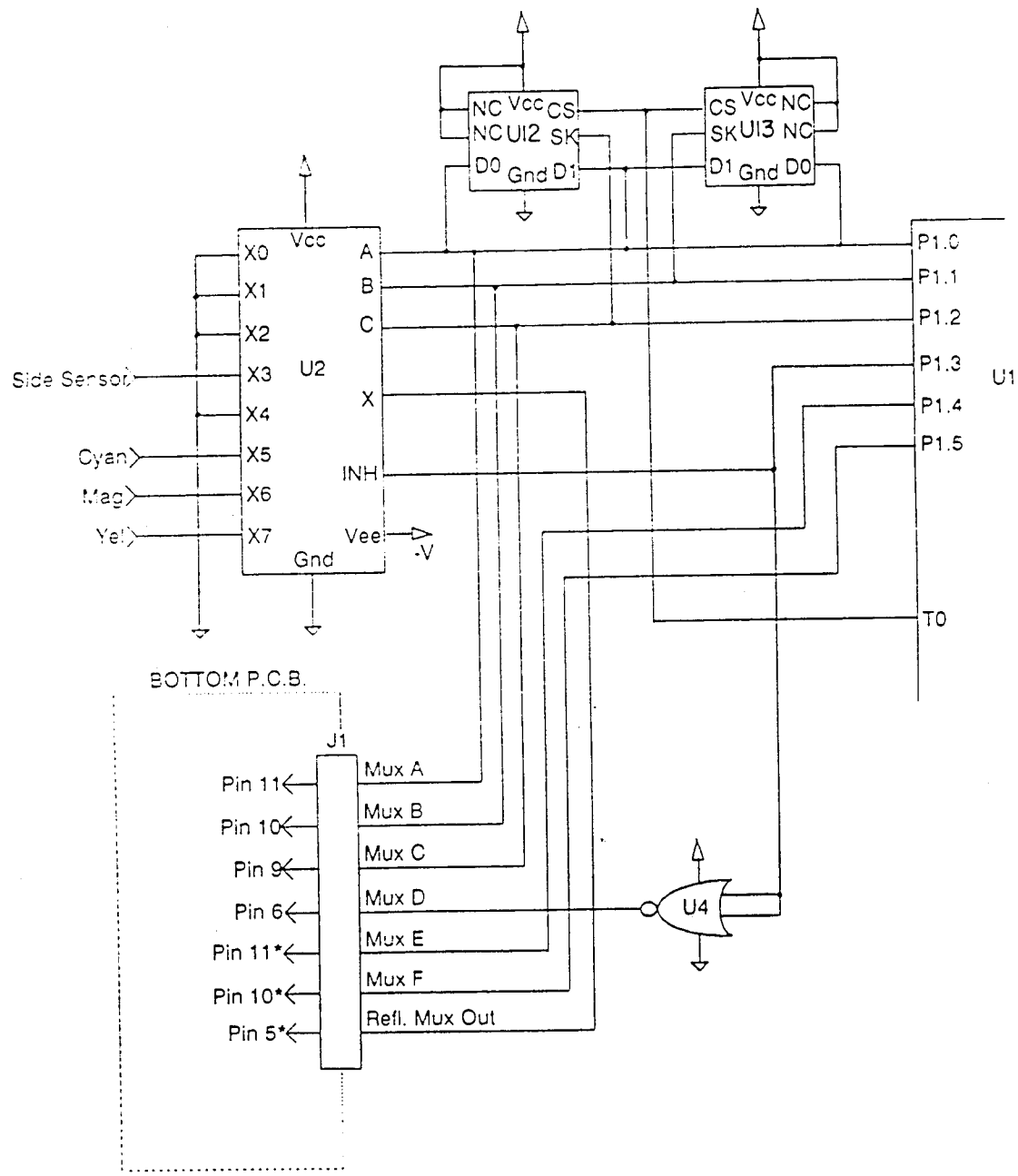
FIG. 19 is a circuit diagram of an illustrative embodiment of the reflection A/D conversion circuitry and memory protection circuitry of the densitometer apparatus.

With respect to the reflection multiplexer 722, transmission multiplexer 732 and A/D converter 734, numerous types of conventional and well known circuit elements can be utilized. For purposes of providing an example, FIG. 18 illustrates circuitry associated with the transmission multiplexer 732 and the A/D converter 734. Correspondingly, FIG. 19 illustrates a detail circuit diagram of circuit interconnections and elements associated with the reflection multiplexer 722 and the A/D converter 734. The circuit elements and interconnections shown in FIGS. 18 and 19 will be apparent to those skilled in the art of densitometry circuit design, and will not be described in detail herein.

Figure 20:
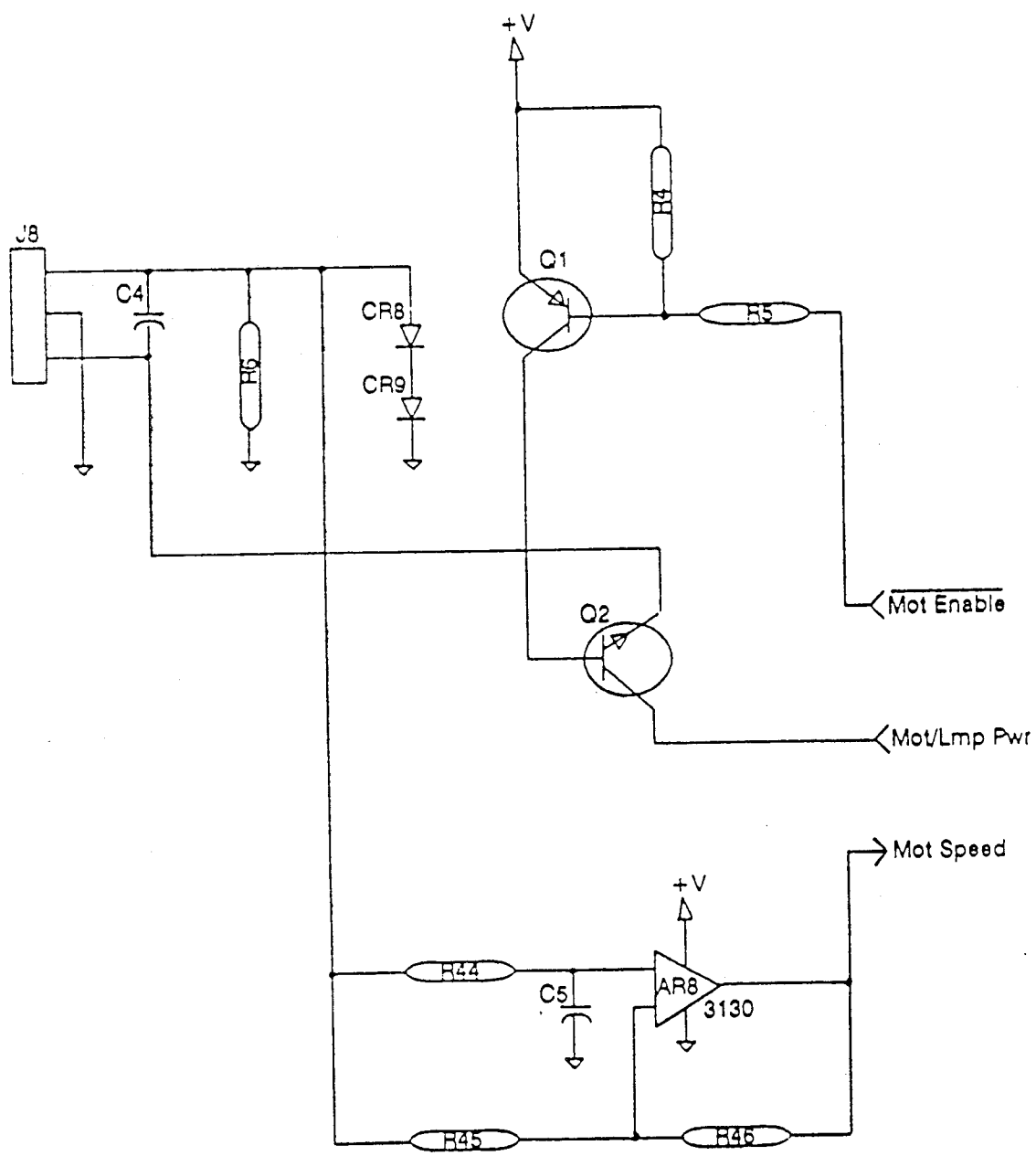
FIG. 20 is a circuit diagram of an illustrative embodiment of a motor control circuit for the densitometer apparatus.

As previously described, the densitometer apparatus 410 also comprises a motor 426. The motor is operated under control of a motor control circuit 742 as illustrated in FIG. 14. Correspondingly, the motor control circuit 742 is controlled by the microprocessor 654, with power being supplied by the power supply 656. Various types of motor control circuits can be employed with the densitometer apparatus 410 in accordance with the invention. An illustrative detailed circuit diagram of a motor control circuit which may be employed with the apparatus 410 in accordance with the invention is shown in FIG. 20. Primarily, the motor control circuit 742 can be utilized under control of the microprocessor 654 to control enablement, direction and speed of the motor 426.

Figure 21:
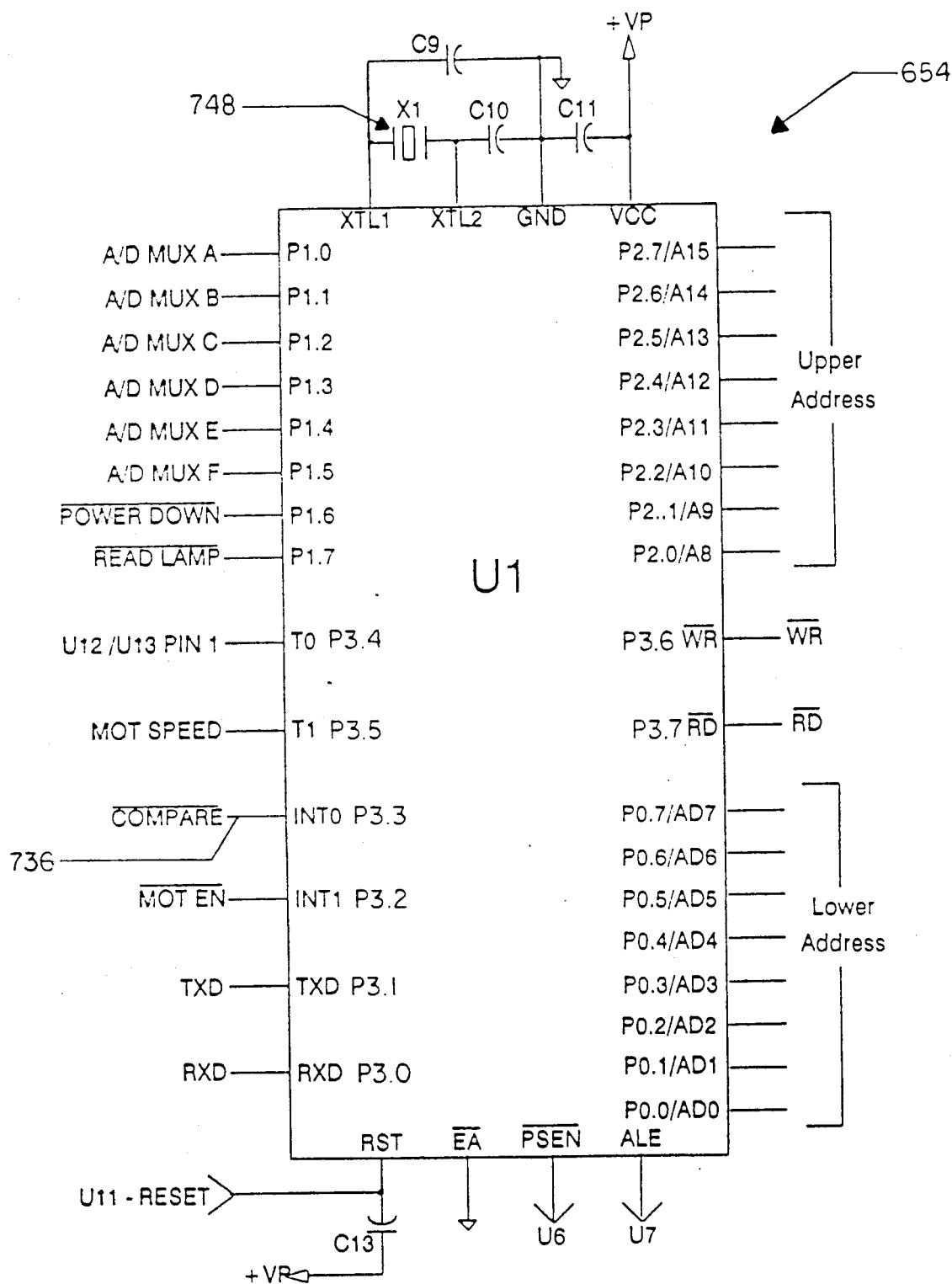
FIG. 21 is an illustrative embodiment of a microprocessor for use with the densitometer apparatus.

The microprocessor 654 is utilized for control of various functions associated with the densitometer apparatus 410. Numerous types of conventional and commercially available microprocessors can be employed for the microprocessor unit 654. An exemplary microprocessor could, for example, comprise the Intel 80C31 8-Bit CMOS Microcomputer commercially available from the Intel Corporation. FIG. 21 illustrates a more detailed diagram of the microprocessor 654. As illustrated in FIG. 21, the microprocessor 654 comprises 128 bytes of read/write data memory, 32 I/O lines configured as 4-bit parallel ports and two 16-bit timer/counters.

As illustrated in FIG. 21, the microprocessor 654 comprises four control/timing signals. Specifically, the RST signal input provides a means for causing the microprocessor 654 to reset. The EA signal is held in a constant state, and allows instruction codes to be obtained from the external memory 744 illustrated as an electrically-programmable read only memory (EPROM). The ALE control signal allows the latching of an address into program memory during normal operation. The PSEN signal is a read strobe that enables the program memory onto the bus during external fetch operations.

The microprocessor 654 also has four sections of I/O ports. The section identified as P0 is an 8-bit open drain bidirectional I/O. It provides the multiplexed low-order address and data bus during access to the external memory 744 illustrated in FIG. 14, as well as the random access memory (RAM) 746 also illustrated in FIG. 14. The I/O ports identified as P1 comprise an 8-bit quasi-bidirectional I/O. The signals identified as P1.0 through P1.5 comprise output signals which control the analog to digital multiplexing. The signal identified as P1.6 provides a power down signal to the power supply 656 after a predetermined period of nonuse. The signal identified as P1.7 is a serial input port which receives data by means of a serial interface.

The section of the I/O port identified as signals P2 also comprises an 8-bit quasi-bidirectional I/O. The signals are utilized to emit the high-order address byte during fetches from program memory. The I/O port section identified as signals P3 also comprise an 8-byte bidirectional I/O. More specifically, the signal identified as P3.0 is a serial input port which receives data by means of the serial interface. Signal P3.1 is a serial output port which transmit data out to the serial interface. Signal P3.2 is an external interrupt, and provides a signal to the motor control circuit 742 for enabling and disabling the motor 426. The signal P3.3 is an external interrupt, utilized as an interrupt for the input line from the A/D converter 734. Correspondingly, the signal identified as P3.4 is utilized to provide output signals to the memory protection circuit 740. The signal identified as P3.5 provides an output signal indicative of the speed of the motor 426, and is applied to the motor control circuit 742. The signal identified as P3.6 is the external data memory write strobe, while the signal identified as P3.7 is the external data memory read strobe. In addition, the element identified as the crystal 748 is connected to inputs XTL1 and XTL2 of microprocessor 654, and provides a clock driving mechanism at a predetermined frequency.

Figure 22:
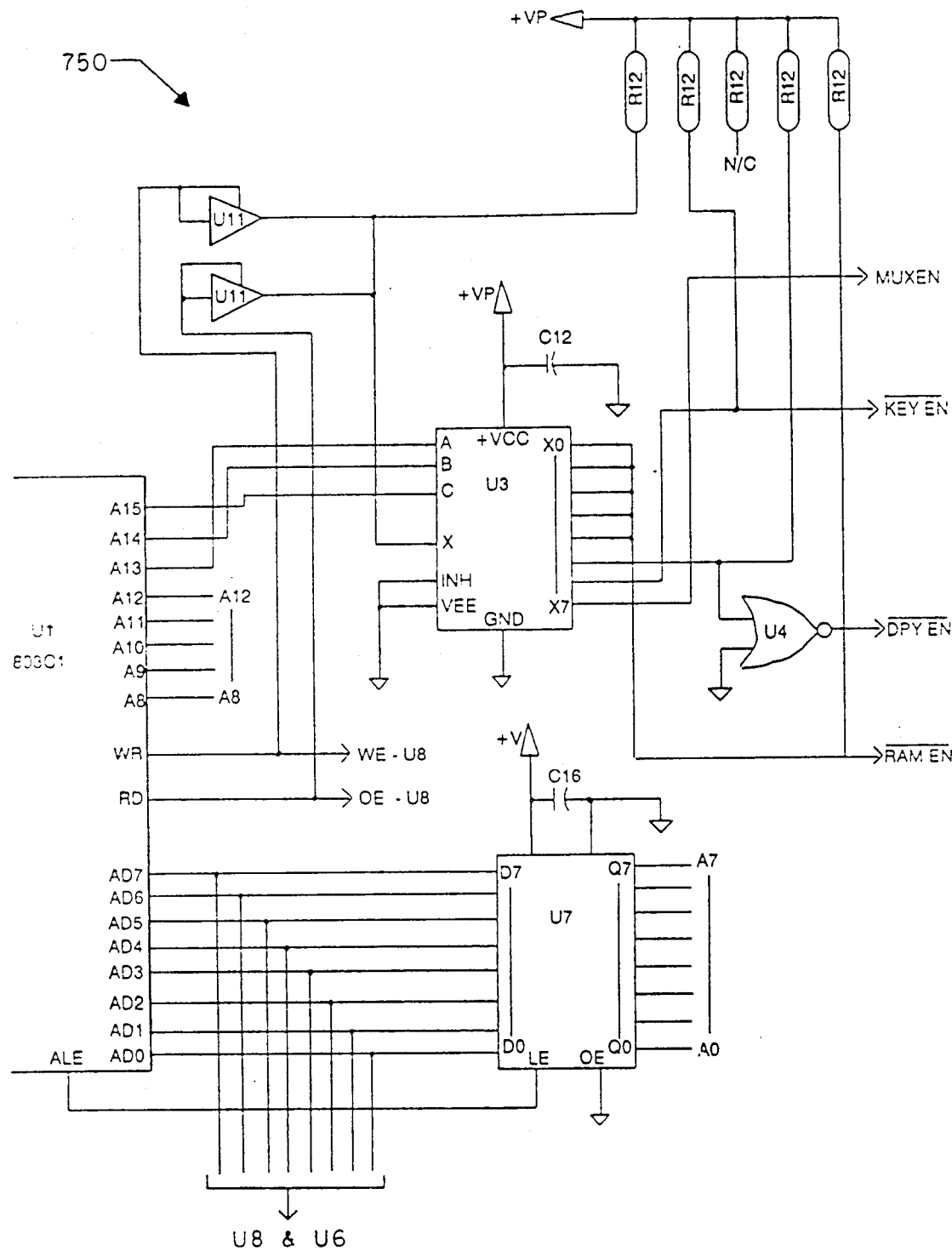
FIG. 22 is a circuit diagram of an illustrative embodiment of the decoding and address latching circuitry for the densitometer apparatus.

Returning to FIG. 14, the densitometer apparatus 410 also comprises an address decoder 750 interconnected to the address bus 752 of the microprocessor 654. The address decoder 750 is utilized to decode the address range for the various devices associated with the bus 754. The address decoder 750 is conventional in design. FIG. 22 is a circuit diagram illustrating an exemplary configuration for the address decoder 750.

As also previously described, the densitometer apparatus 410 includes an EPROM 744 which can comprise, for example, a CMOS 512K EPROM. In addition, the apparatus 410 can also comprise the random access memory 746. The RAM 746 can, for example, comprise an 8192 byte static random access memory.

Figure 23:
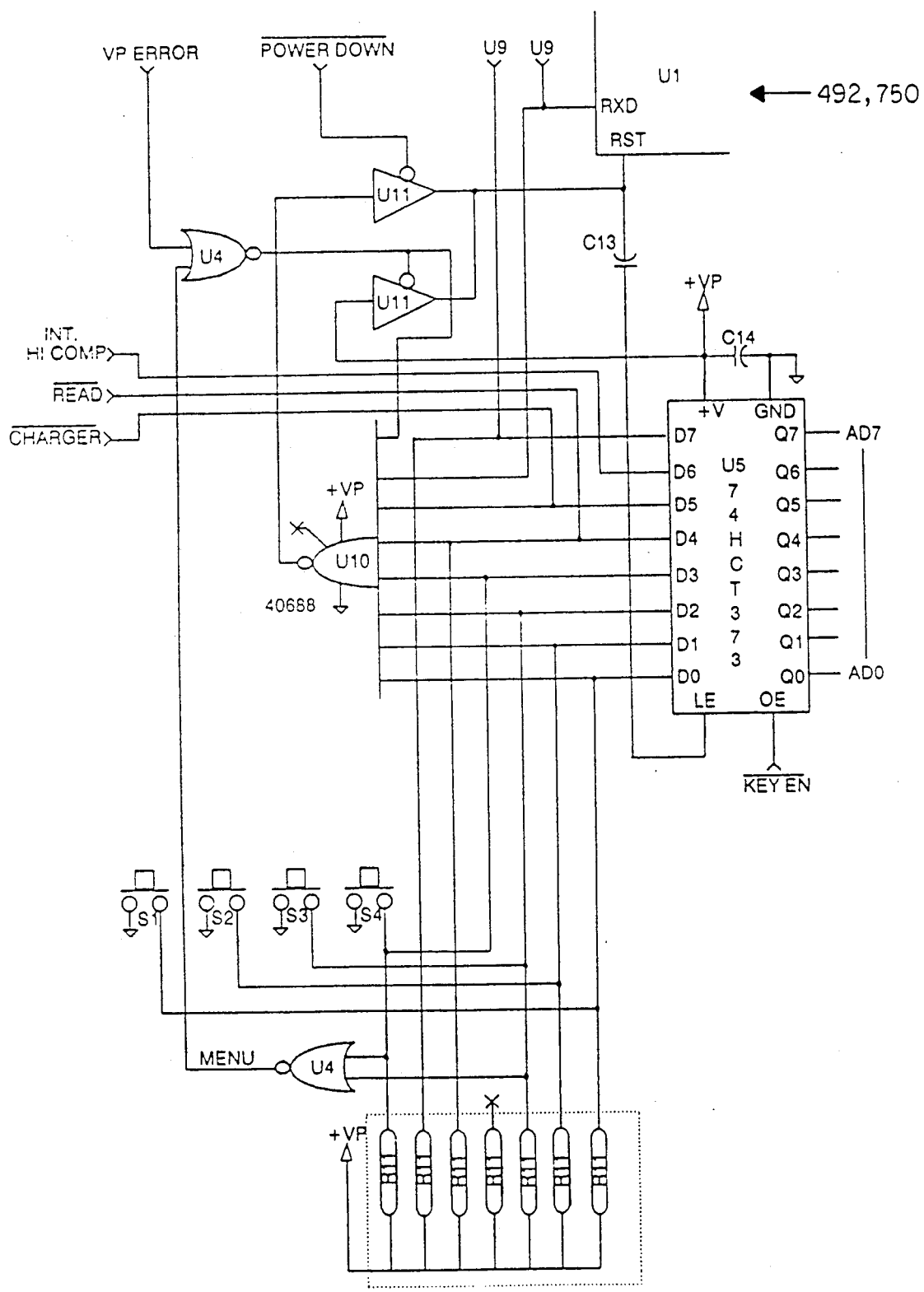
FIG. 23 is a circuit diagram of an illustrative embodiment of the reset circuitry and key switch circuit assembly for the densitometer apparatus.

As also previously described, the densitometer apparatus 410 can include a series of key switches 492. These key switches will operate in conjunction with a reset circuit 750 as illustrated in FIG. 14. As previously described, the reset circuit 750 is controlled in part by the microprocessor 654. A detailed circuit diagram of an exemplary reset circuit 750 and key switch arrangement 492 is illustrated in FIG. 23.

The operation of the densitometer apparatus 410 will now be described with respect to functions which can be performed by the apparatus 410 in accordance with the invention. The functions to be provided by apparatus 410 will utilize various structural components of the densitometer apparatus. However, in most instances, these functions will also employ certain computer programs and stored data associated with the microprocessors 654 and the memories 744 and 746. Although the detailed instruction code of these programs is not set forth in detail herein, the actual programming of the functions, given knowledge of the sequence of operations to be performed, will be apparent from the subsequent detail herein.

The functions to be performed by the densitometer apparatus 410 in accordance with the invention will also be described with illustrations of displayed information within the display 490, and the operation of the individual key switches of the key switch assembly 492. In the drawings associated with these functions, an illustrative example of the data which can be displayed in the visual display 490 will be shown. Also, the particular individual key switches of the key switch assembly 492 which may be used by the operator during any particular functions will also be illustrated. For purposes of understanding, the drawings associated with the description of the operation will represent displayed information in the display 490 (i.e. functions, messages, etc.) through uppercase letters. Lowercase letters shown in the display 490 will indicate particular functions which may then be performed by activation of the keys of the key switch assembly 492. In particular, active keys of the key switch assembly 492 (i.e. those keys which may be utilized with respect to the particular function) will also be shown.

In accordance with the invention, the densitometer apparatus 410 includes certain prestored data associated with the most commonly used control strips for control of photograph processing. This data can be prestored within the memories 744 and 746 in any desired organization. When a particular control strip is to be "selected" by the operator, the microprocessor 654 is programmed so as to generate data to the display 490 which will identify the particular selected control strip. For purposes of information to the operator, it is also possible to display a lowercase letter next to the strip type on the display 490 for purposes of designating the manufacturer of the strip. For example, the lowercase letter "k" next to a strip type on the display 490 can indicate that the manufacturer of the strip is the Eastman Kodak Company.

Figure 24:
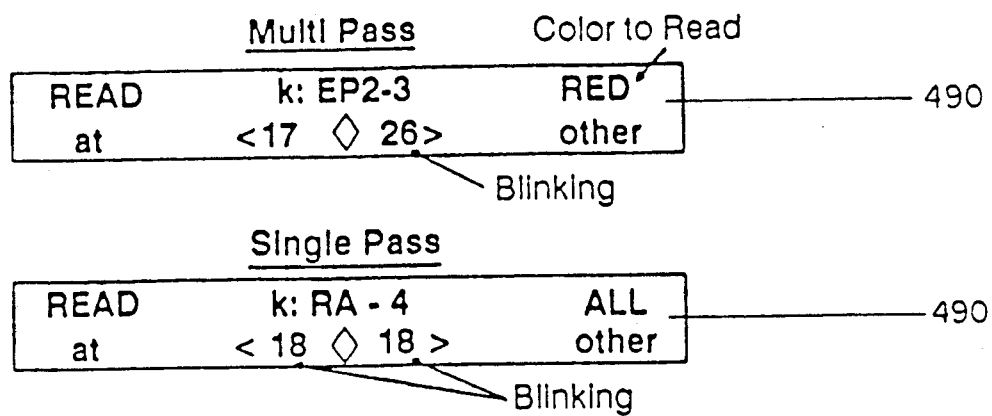
FIG. 24 illustrates the user interface visual display assembly.

Also in accordance with the invention, the densitometer apparatus 410 can display various information on the display 490 relating to the guide setting positions for the guides 468 and 470. FIG. 24 illustrates two types of indicia which may appear on the display 490. On the display 490 identified as the "multi-pass" display, the guide settings for the guides 468 and 470 are identified at the lower center portion of the display 490. For example, as shown in FIG. 24, the left guide 468 is identified as being set at location 17 of indicia 550, while the right guide 470 is indicated to be set at location 26 of indicia 550. Correspondingly, in the example display 490 identified as the "single pass" display in FIG. 24, both the left and right guides 468, 470 are indicated to be set at locations 18 of indicia 550. In addition, the apparatus 410 is also adapted to generate signals to the display 490 which cause the location indicators for indicia 550 to be blinking in certain instances. For example, one guide setting for the indicia 550 can be set to a blinking mode by appropriate signals from the microprocessor 654 to the display 490, in the event that the control strip to be tested is to "rest" first on this particular guide setting when the control strip is inserted into the apparatus 410. Correspondingly, if the control strip to be tested need only be passed through the densitometer apparatus 410 once, both indicator guides can be set to a blinking state.

Again, the densitometer apparatus 410 is adapted to operate as an automated instrument for measuring color densities of film control strips, paper control strips and printer balance strips. The densitometer apparatus 410 is motorized and comprises fixed optics assemblies (rather than moveable optics assemblies) for purposes of measuring the color densities. As desired, the microprocessor 654 can be programmed so as to appropriately sort the data for measured control strip fields such as HD, LD, and "Stain." In addition, through the RS 232 interface 544 as illustrated in FIG. 14, the sorted data can be transmitted to a peripheral device, such as a printer, while simultaneously applying signals so as to display the data on the display 490. Correspondingly, the RS 232 interface can be "set up" to receive instructions for the microprocessor 654 from external computing devices. Concepts, structures and procedures for such external control through the interface are disclosed in Peterson et al. U.S. Pat. No. 4,591,978 issued May 27, 1986.

Control strips are typically broken down into three categories, namely paper, film, and printer balance strips. Relatively common paper control strips utilized in the industry are identified as EP2, RA-4, CP-21, AP-92, R-3, and P-3. Common film control strips well known in the industry are CD-41, KBM, CN-16. Relatively common printer balance control strips comprise strips known as the generic normal bulls-eyes, generic "UNO" 3 print series, MC/3510/2610 5 print series, and others.

In accordance with the invention, the densitometer apparatus 410 will provide an output of a red, blue and green color density value for each field of the control strip which is measured. The only requirement placed on the areas to be measured is that the control strip areas must be aligned to either the left side, right side or center line of the strip, in a straight line format.

Further in accordance with the invention, the densitometer apparatus 410 can accommodate differing sized control strips by use of the paper guides 468 and 470. These adjustable paper guides provide adjustment by merely sliding the paper guides to the appropriate settings which may be applied from the microprocessor 654 to the display 490. The guides thus provide control of movement in one dimension.

The densitometer apparatus 410 in accordance with the invention comprises a number of features. As earlier described, both reflection color densities (for paper control strips) and transmission color densities (for film control strips) can be measured by the apparatus, through the reflection optics assembly 576 and the transmission optics assembly 618. In addition, with the use of the microprocessor 654 and the associated memories 744 and 746, data related to the measured color densities can be stored and sorted as required, given predetermined information stored in the microprocessor 654 relating to the sequence of color areas to be measured on known control strips.

Still further, as described in subsequent paragraphs herein, the densitometer apparatus 410 is adapted to provide automatic calibration for transmission and reflection densitometry. Control of the densitometer apparatus 410 by the operator is provided by a relatively simple 4-key operation using the key switch assembly 492. The display 490, as earlier described, can comprise a 16 character by 2 line conventional LCD display.

For purposes of utilizing the densitometer apparatus 410 in accordance with the invention, it is preferable to include prestored data comprising a library of preprogrammed strip formats (paper, film and printer balance). The data to be stored with respect to the strip formats includes identification data for the particular control strips, the sequence of color areas on the control strips, and other appropriate relevant data.

When a control strip is to be read, the strip can be inserted into the appropriate slot formed between the paper guides 468 and 470. If the control strip is a 35 millimeter strip, the strip can immediately be inserted into the densitometer apparatus 410 in the slot 454. As the control strip is inserted between the guides 468, 470, the forward edge of the control strip will contact the read switch 458. Operation of the read switch 458 will cause the motor assembly 426 to be activated and enabled through the motor control 742. In this manner, the control strip to be read will be moved through the optics assemblies 576 and 618 by means of the previously described idler wheel assembly 440 and drive wheel assembly 434 as illustrated in FIG. 8. As the control strip to be tested is moved through the densitometer apparatus 410 and under the source light 578, either reflection color densities or transmission color densities can be measured, depending on the type of control strip. If the control strip is a paper control strip, reflection densities will be measured. Alternatively, if the control strip is a transmission control strip, transmission densities will be measured. These signals indicative of the color densities are applied to the microprocessor 654 as previously described with respect to FIG. 14 and associated drawings. This data indicative of the color densities of the various areas of the control strips can then be utilized as required to generate appropriate display information to the operator through the display 490.

As desired, the densitometer apparatus 410 can also include several other features. For example, with the circuitry as previously described herein, the densitometer apparatus 410 allows a "default" format for paper, film and printer balance control strips to be set, so that a strip can be read without having to first manually select the strip format. Also, reference strips can be measured, with the option to enter correction factors and/or perform crossover features as desired through information input through the key switch assembly 492.

Figure 25:
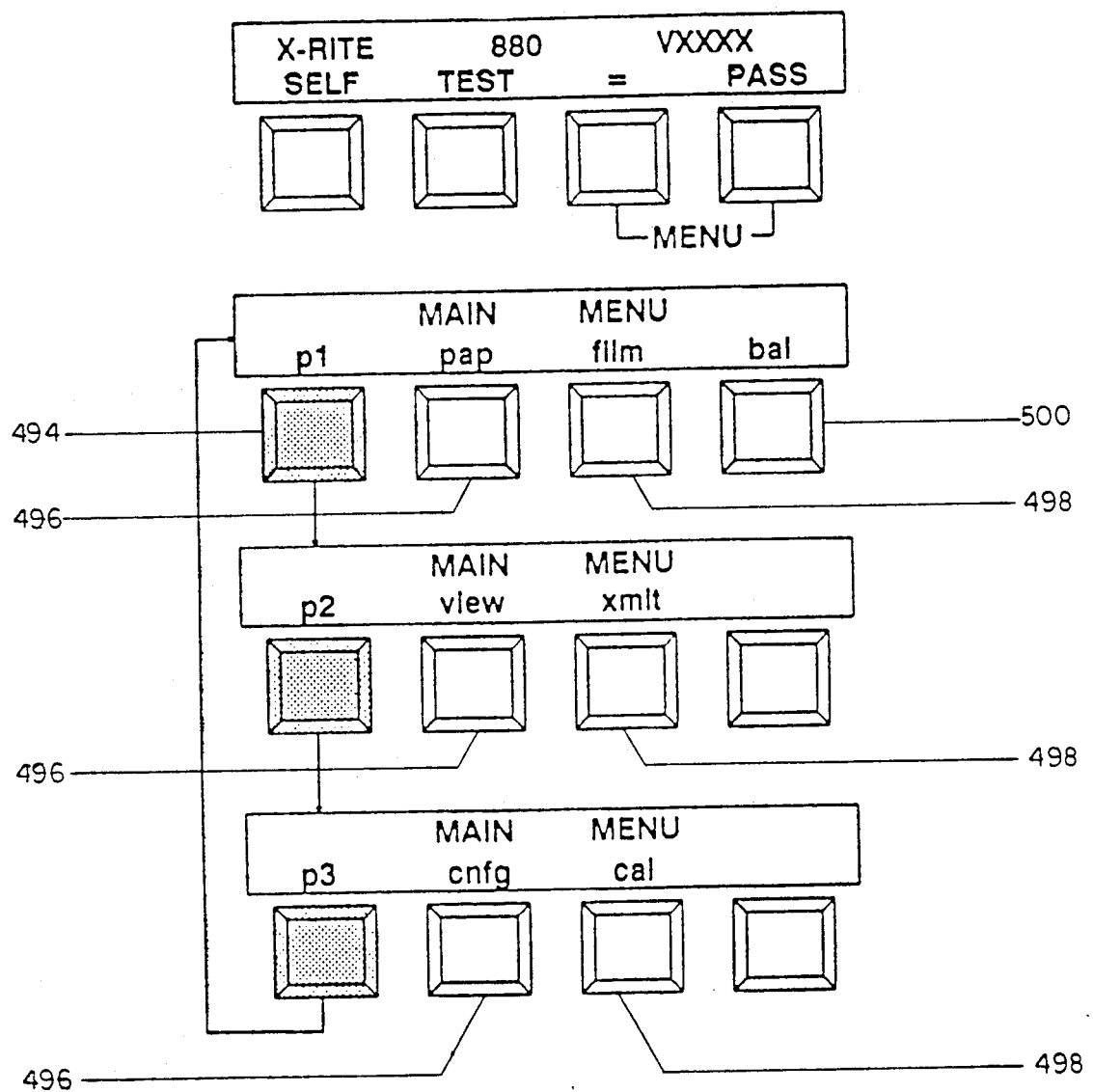
FIG. 25 illustrates the visual display and the key switch assembly for the densitometer apparatus.

As an exemplary description of the operation of the apparatus 410, when power is applied to the apparatus 410, a conventional diagnostic procedure can be performed to ensure that all elements of the apparatus 410 are operating properly. After completion of the diagnostic procedure, a "main menu" can be displayed through signals applied from the microprocessor 654 to the display 490. As illustrated in FIG. 25, the various options which can be selected by the operator may require more than four keys. Accordingly, the main menu options can be segmented into separate "pages." Accordingly, when the operator selects display of the main menu, page 1 can be indicated as being displayed by the symbol "P1" over the key switch 494. If the operator wishes to "advance" through the pages of the main menu, the key switch 494 can continue to be pressed. As an illustration as shown in FIG. 25, the main menu comprises three pages.

The densitometer apparatus 410 can be provided with several basic functions. For example, the "paper" function identified by the display of the symbol "PAP" over key switch 496 as illustrated in FIG. 25 can be utilized to set the apparatus 410 to the paper measuring function. That is, signals will be provided from the key switch assembly 492 to the microprocessor 654 indicating that a paper control strip is to be measured. Accordingly, the apparatus 410 will be appropriately configured by the microprocessor 654 to expect color measurements performed by the reflection optics assembly 576. Alternatively, the "film" function can be selected by depressing the key switch 498 as illustrated in FIG. 25 during the page 1 portion of the main menu. Depression of this key switch will cause the signals applied to the microprocessor 654 to "set" the apparatus 410 to measure transmission densities associated with film control strips. Correspondingly, by depressing key switch 500 as illustrated in FIG. 25, the operator can "set" the apparatus 410 to the printer balance measuring function. Each of the aforedescribed functions can remain set until such time that the operator selects a different function.

Referring to the page 2 main menu as shown in FIG. 25, depression of key switch 496 can transmit appropriate signals to the microprocessors 654 to cause the data associated with the last measured control strip to be applied as output signals to the display 490. Also with respect to page 2 of the main menu, depression of the key switch 498 can be utilized to transmit data from the last measured control strip from the memories 744 and 746 to the RS 232 interface 544.

Referring to the page 3 main menu functions as illustrated in FIG. 25, depression of the key switch 496 can be utilized to preset certain functions, and as identified as the "configuration" feature. The configuration mode can be utilized to allow the operator to set various parameters such as transmission band rate and the like. This feature can be used as a "miscellaneous" mode to allow the operator to set parameters primarily relating to data transmission and data format. Correspondingly, depression of key switch 498 can be utilized to cause the densitometer apparatus 410 to perform a calibration function as described in subsequent paragraphs herein.

As previously described, the densitometer apparatus 410 is adapted to accommodate different sized and differently configured control strips. For this accommodation, the apparatus 410 includes the adjustable guides 468 and 470 on each side of the control strip entrance. Positioning of the control strips 468, 470 is indicated by the numerical indicia 550 on the forward edge of the apparatus 410. When a control strip is to be read, the microprocessor 654 can obtain data from the memory 746 indicative of the width of the control strip and the appropriate guide settings for the guides 468 and 470.

Figure 26:
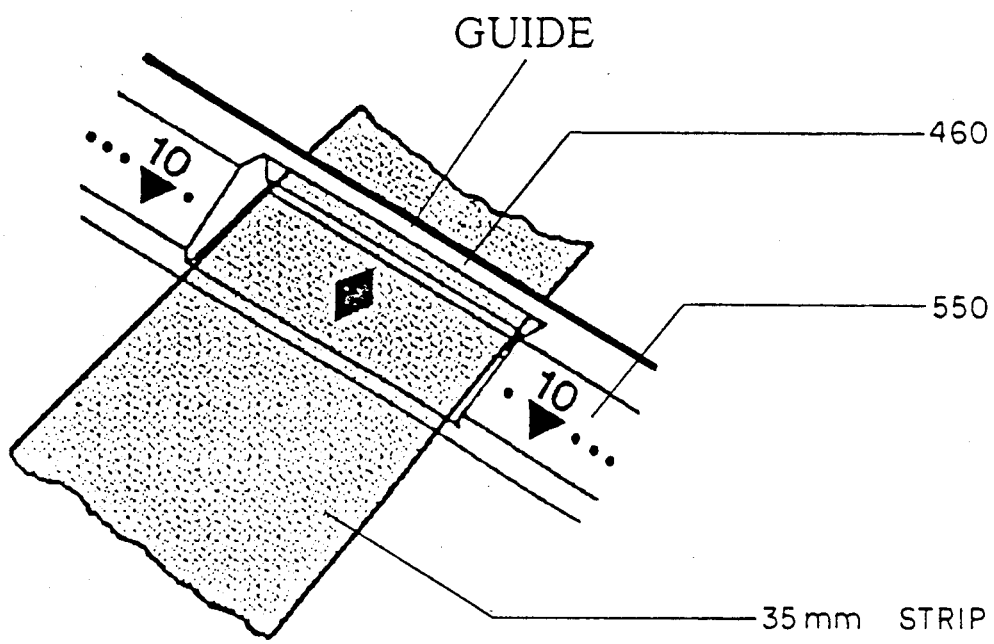
FIG. 26 illustrates the use of the densitometer apparatus with 35 millimeter control strips.

These guide settings can then be applied as signals to the display 490 to automatically display to the user the appropriate guide settings for the particular control strip selected. Further, as also previously described, the densitometer apparatus 410 includes a film guide bar 460 (illustrated in FIG. 8) located above the slot 454 for purposes of specifically accommodating 35 millimeter strips. In this regard, the slot 454 has the appropriate width for the 35 millimeter strips. Positioning of the 35 millimeter strips is illustrated in FIG. 26.

Figure 27:
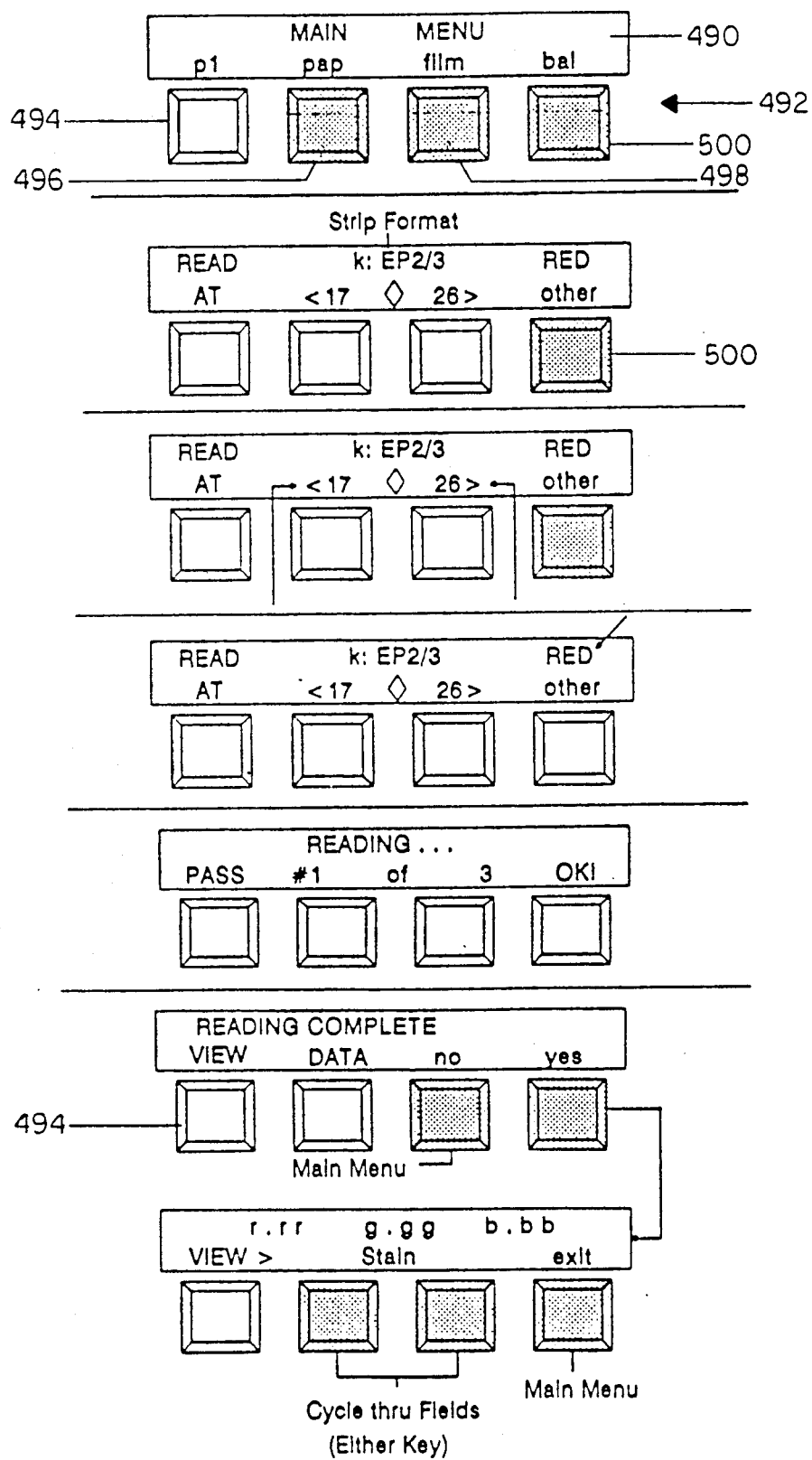
FIG. 27 is an illustration of the key switch assembly and display for use when reading a control strip.

For purposes of obtaining color density measurements for film, paper and printer balance strips, a substantially identical procedure is utilized for each type of control strip. FIG. 27 illustrates a sequence of operator selections and displays for the key switch assembly 492 and the display 490 for measuring various types of control strips. First, as illustrated in FIG. 27, with page 1 of the main menu generated from the microprocessor 654 to the display 490, the operator can select the control strip category by depressing one of the switches 496, 498 or 500, corresponding to paper, film and printer balance, respectively. When a particular strip category is selected, the microprocessor 654 is adapted to retrieve from the memories 744 and 746 appropriate data for the various types of control strips within the particularly selected strip category. The strip format for the first strip stored in the memory 744 and 746 is displayed by the microprocessor 654 through signals output to the display 490. As illustrated in FIG. 27, this first strip format may be identified as "K: EP2/3". If this is not the appropriate strip format desired by the operator, key switch 500 can be depressed, indicating that the microprocessor 654 is to retrieve the data for the second control strip stored for the particular category. In this manner, each of the control strip formats stored for the particular strip category can be sequenced through the display 490 until the desired strip format appears on the display 490.

When the desired strip format has been obtained, the display 490 will appropriately indicate the settings for the guides 468 and 470. For example, as illustrated in FIG. 27, the appropriate guide settings are 17 for the left paper guide 468 and 26 for the right paper guide 470.

When the paper guides have been appropriately set, the strip is inserted by the operator. However, if the control strip to be inserted will require a multiple pass through of the strip to read all of the color areas on the strip, the display 490 is adapted to display, at the upper right hand corner as shown in FIG. 27, the color to be measured. As further illustrated in FIG. 27, if the control strip has more than one column to be measured, the microprocessor 654 is adapted to apply signals to the display 490 to indicate the particular number of passes required for the control strip.

Following completion of the reading of the control strip, the display 490 will generate signals indicating that the reading of the control strip is complete. As illustrated in FIG. 27, the operator can then depress key switch 494, requesting a viewing of the data. As shown in the lowermost display of FIG. 27, the data will be displayed in the form of color densities for the red, green and blue colors.

Figure 28A:
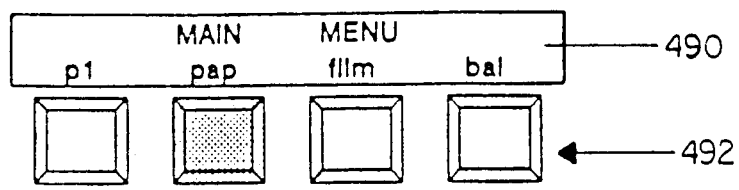
FIG. 28A is an illustration of the display, key switch assembly and a control strip during reading operations.
Figure 28A:
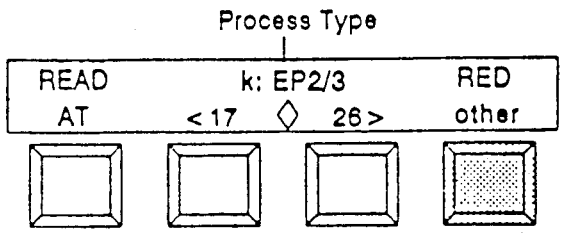
Figure 28A:
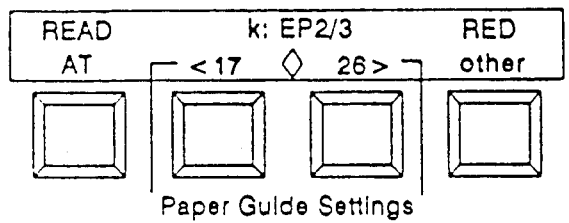
Figure 28A:
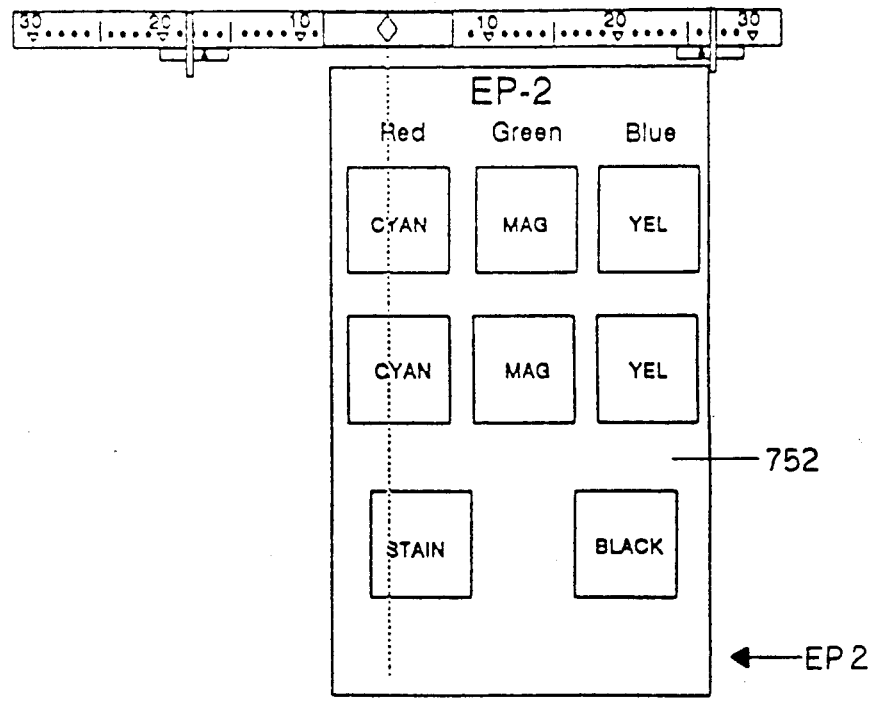
Figure 28:
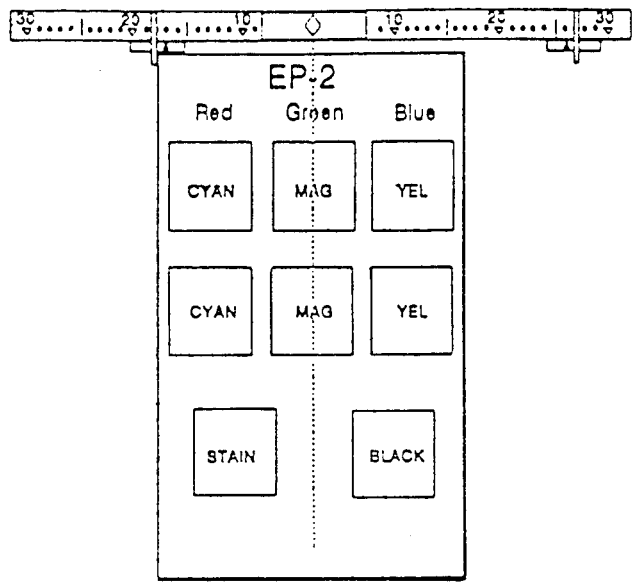
FIG. 28B is a continuation of the illustration of the control strip and the visual display and key switch assembly when reading a control strip.
Figure 28:
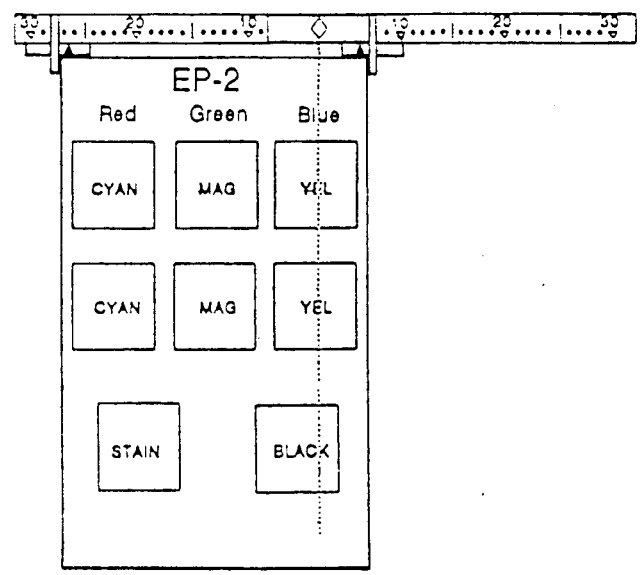
Figure 28:
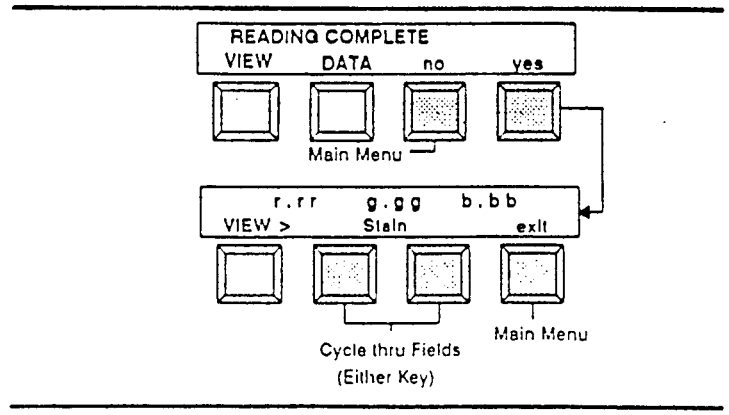

To further illustrate this reading of the data, FIGS. 28A and 28B illustrate a relatively well known old style EP2 control strip identified as control strip 752. Also illustrated in FIG. 28 is the display 490 and key switch assembly 492 as utilized for measuring of this control strip. As apparent from FIG. 28, the paper control strip 752 essentially comprises three columns of color patches. After the operator has selected the paper strip category, the operator will sequence the display 490 through the particular control strip formats until the appropriate EP2 format is displayed on the display 490. The paper guides 468, 470 are then set to the appropriate indicia as indicated by the display 490. As illustrated in FIG. 28A, the control strip is aligned against the right hand guide 470 for purposes of measuring the red and stain fields. In this regard, and as previously described, the numerical indicia 26 displayed for the right hand paper guide 470 would be in a blinking state to indicate that the strip 752 is to be inserted in an abutting position to the right hand paper guide 470.

The strip 752 is then inserted into the apparatus 410 and the red and stain fields are measured for appropriate color density. After measurement, the motor control 742 and motor assembly 426 will cause the control strip 752 to be retracted from the apparatus 410. The display 490 will then indicate that the strip is to be aligned against the left hand guide 468 (through blinking of the numerical indicia for the left guide 468) for purposes of measuring the green color areas. This measurement is shown in the upper illustration of FIG. 28B. After this pass of the control strip 752 is complete, the display 490 indicates to the operator that the strip 752 should be rotated and aligned with the right hand guide 470 for purposes of measuring the blue and black fields. Following this reading, the display 490 will indicate that the reading is complete and will allow the user to view the color density measurements as desired.

Figure 29:
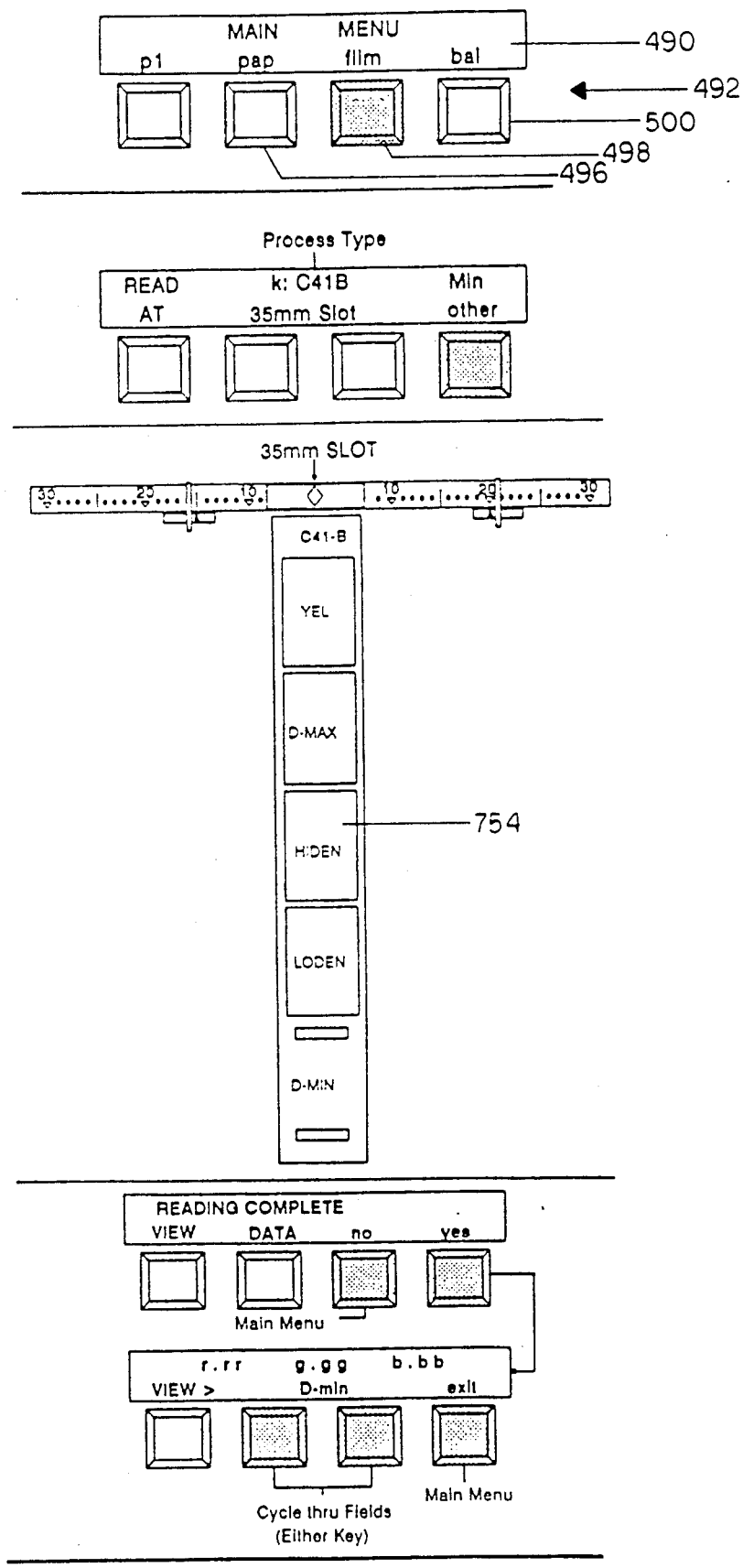
FIG. 29 is an illustration of the visual display and key switch assembly utilized when reading a single pass control strip.
Figure 30:
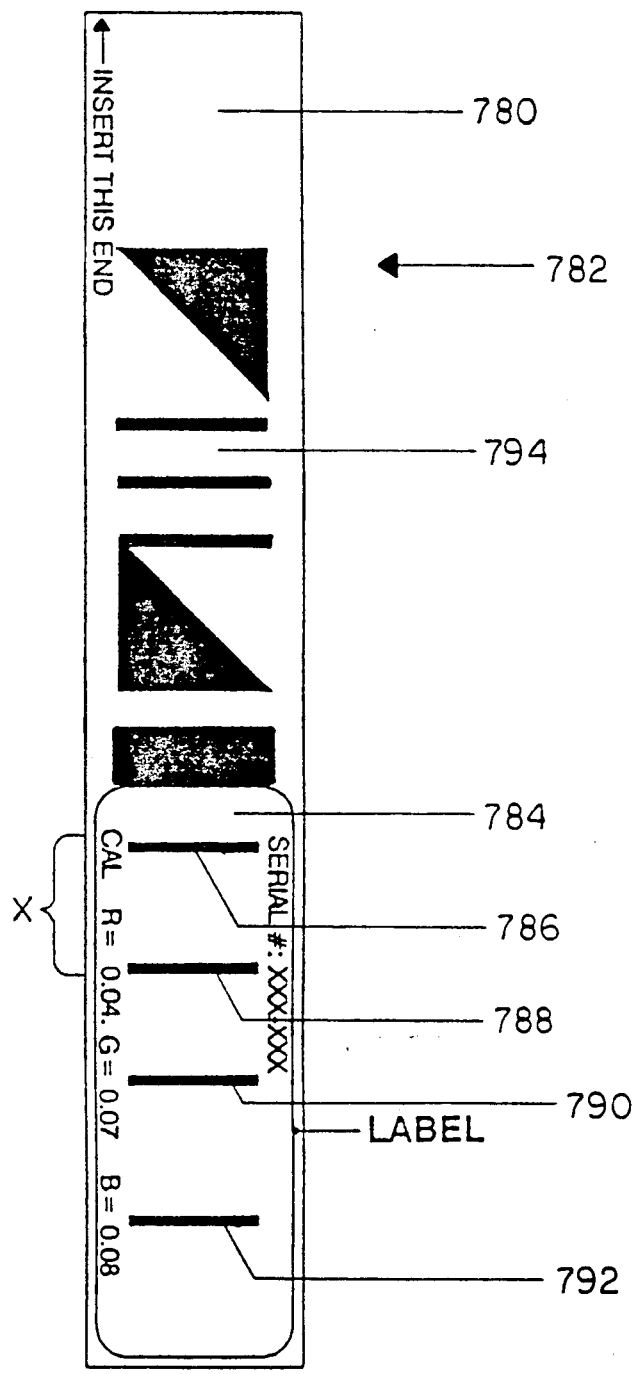
FIG. 30 illustrates the configuration of an auto calibration strip for use with the densitometer apparatus.

The foregoing describes a multipass color density measurement. FIG. 29 illustrates the measurement of a C41-B film strip, requiring only a single pass. As illustrated in FIG. 29, the operator will initiate the measurement by depressing key switch 498 indicating that the film strip category is to be selected. As previously described with respect to paper strips, the operator can sequence through the strip formats displayed on the display 490 until such time as the C41-B strip format is indicated. Thereafter, the user can insert the C41-B control strip (identified as strip 754) into the 35 millimeter slot until the read switch 458 is activated. The various color areas associated with the strip 754 will then be read by the apparatus 410. When reading of the control 754 is complete, an appropriate display will be generated on the display 490, and the operator will again be allowed to view the measured data as desired.

As previously described, the apparatus 410 is adapted to transmit color density measurement data to peripheral devices. To perform such a function, the operator can depress key switch 498 on page 2 of the main menu to provide the transmit function. The current data which has been obtained by the microprocessor 654 can then be applied to the RS 232 interface 544 and to the appropriate interconnected peripheral device.

As further illustrated in FIG. 25, page 3 of the main menu includes a function identified as the calibration function. The concept of calibration is well known to those skilled in the art of densitometer design. Briefly and simplisticly, it is necessary to calibrate densitometers for purposes of adjusting the slope between low density and high density measurements as previously described in the Background of the Invention section. In prior densitometers, reference strips were utilized where various color patches were measured for purposes of obtaining the end points (i.e. low density and high density) for the density measurements. By setting the densitometer to obtain the same density measurements, the calibration could be achieved. However, such calibration required the use of a number of reference strips, all of which could change color densities as the strips aged. Also, the color density measurements would have to be manually input by the operator into the densitometer.

In accordance with the invention, the densitometer apparatus 410 includes an automatic calibration feature. This calibration feature utilizes what is referred to as an automated calibration strip illustrated in FIG. 30. This calibration strip, identified as calibration strip 780, includes the indicia indicated on the upper part of the strip as indicia 782. At the lower portion of the strip, a label 784 has been adhesively attached to the control strip 780. The label includes a bar code arrangement comprising four bar codes. The bar codes are identified as the calibration base line 786, the red bar code 788, green bar code 790 and blue bar code 792. In addition, the calibration control strip is preferably of a 35 millimeter width and includes a color patch on the upper portion of the strip 780 identified as color patch 794.

The color patch 794 of the calibration strip 780 has been previously measured at the manufacturer's facilities. The label 784 comprises an encoding of the calibration measurements for the patch 794 of strip 780. Specifically, the displacement of the bar codes 788, 790 and 792 relative to the calibration base line 786 indicates the red, green and blue reflectance measurements for the strip 780. Any of numerous displacement algorithms can be employed. As an example, however, the displacement indicated as displacement X in FIG. 30 of the red bar code 788 relative to the calibration base line 786 indicates a numerical value for the red reflectance. As indicated by the printed indicia on the label 784, the red reflectance is identified as 0.04. If the displacement algorithm utilized with the label 784 employed a tenth of an inch for each one hundredth of reflectance, the red bar code would be four tenths of an inch displaced from the calibration base line 786.

Using the same algorithm, the green base line 790, indicated by the printed indicia as indicative of a green reflectance of 0.07, would be seven tenths of an inch away from the calibration base line 786. Correspondingly, the blue bar code 792, having printed indicia indicating a blue reflectance of 0.08, would be eight tenths of an inch away from the calibration base line 786.

However, for purposes of insuring that the bar codes 788, 790 and 792 are not required to overlap in any manner, a further adjustment to the displacement algorithm is utilized. That is, as an example, the calibration base line 786 can be considered to be at a "zero" value for the red bar code 788. However, for the green bar code 790, the calibration base line 786 can be characterized as being at a different value than zero, for example, −0.04. Correspondingly, the calibration base line 786 can be characterized as being at a position of −0.08 relative to the blue bar code 792.

In accordance with the foregoing, the use of the bar code displacement arrangement will allow the densitometer apparatus 410 to automatically detect the reflectance value for the calibration. Accordingly, it is not required for the operator to in any manner manually input the calibration values. The microprocessor 654 is provided with a control program for purposes of measuring the displacement between the calibration base line 786 and the various bar codes 788, 790 and 792. Such an algorithm would utilize a pattern recognition arrangement. Programming of pattern recognition functions is well known in the art of computer program design and circuit design.

To provide a complete calibration, using the automated calibration feature, the user can depress the appropriate keys of the key switch assembly 492 to activate the apparatus 410 to perform the calibration function. For purposes of calibrating the reflectance, and to obtain the low density value (i.e. high reflectance) the calibration strip 780 is inserted into the apparatus 410. The apparatus 410 then performs a measurement of the displacement of the bar codes 788, 790 and 792 relative to the calibration base line 786. This information is stored in the memory 746, and is utilized to adjust the circuitry of the apparatus 410 to provide a low density value and high reflectance in accordance with this measurements.

To obtain the low reflectance and high density value for the reflection density calibration, the densitometer apparatus 410 is adapted to disable the source light 578. By disabling the source light 578, the measurement of the density values by the reflection optics assembly 576 can be characterized as representative of the density values for a low reflectance. Accordingly, with the high density and low density values, the slope of the density measurement circuitry can be adjusted.

For purposes of calibration of the transmission density measurement path, and in accordance with the invention, the densitometer apparatus 410 provides a "standard free" calibration. That is, for purposes of determining the high transmittance and low density value, the transmission optics assembly 618 is adapted to measure densities with the source light 578 enabled, but without any control strip inserted between the transmission optics assembly 618 and the source light 578. That is, the transmission optics assembly 618 is essentially measuring "air", and is assumed to be measuring the densities associated with a substantially 100% transmittance. For purposes of measuring the low transmittance (i.e. high density), the source light 578 is again disabled. The transmission optics assembly 618 is adapted to measure the transmittance with the source light 578 disabled, and obtain a low transmittance and high density value. In accordance with the foregoing, the appropriate end points can be obtained for adjusting the slope of the circuitry associated with the transmission density measuring path.

Also, it should be mentioned that a manual calibration can be provided by performing an actual measurement of the color patch 794 of the auto calibration strip 780. Correspondingly, such a measurement can be utilized for purposes of calibrating the densitometer apparatus 410 to another densitometer apparatus.

In accordance with the foregoing, the densitometer apparatus 410 can be utilized as an automated strip reading densitometer to perform a number of different features as previously described herein. However, it should be emphasized that the principles of the invention are not limited to the specific densitometer apparatus 410 described herein. For example, other types of circuit components can be employed. Still further, the features of the apparatus 410 in accordance with the invention as described herein are not necessary limited to three-color functions or to the use of red, blue and green spectral filters. A different number of colors and different color shades could be employed without departing from the novel concepts of the invention. It will be further apparent to those skilled in the art that additional modifications and variations of the above-described illustrative embodiment of the invention may be effected without departing from the spirit and scope of the novel concepts of the invention.

The embodiments of the invention in which an exclusive property or privilege is claimed are defined as follows:

1. A densitometer system adapted for measuring color characteristics of object samples under test, said system comprising:

light source means for generating light rays and directing the same onto said object samples;

reflection filter means positioned at a predetermined angle relative to the direction of object illumination by said light source means, and responsive to light rays reflected from said object samples so as to discriminate a predetermined color shade set of spectral responses of said reflected light rays;

transmission filter means positioned relative to the direction of object illumination by said light source means, and responsive to light rays transmitted through said object samples so as to discriminate a predetermined color shade set of spectral responses of said transmitted light rays;

reflection detection means responsive to light rays transmitted through said reflection filter means for generating on separate reflection detection paths reflection signals representative of the intensity of said light rays transmitted through said reflection filter means;

transmission detection means responsive to light rays transmitted through said transmission filter means for generating on separate transmission detection paths transmission signals representative of the intensity of said light rays transmitted through said transmission filter means;

reflection multiplexing means connected to said reflection detection means for time multiplexing said reflection signals on said separate reflection detection paths;

transmission multiplexing means connected to said transmission detection means for time multiplexing said transmission signals on said separate transmission detection paths;

processing means connected to said reflection multiplexing means and to said transmission multiplexing means for processing said multiplexed signals;

input means connected to said processing means for providing operator input to said densitometer system;

display means connected to said processing means for providing visual signals to an operator indicative of functions performed by said densitometer system;

motor means connected to said processing means and adapted to automatically move said object samples through said densitometer system adjacent said light source means so as to provide an automated measurement of a plurality of color patches associated with said object samples; and guide means mounted to said densitometer system and adjustable by said operator so as to provide a guidance in at least one dimension of said object samples through said densitometer system.

2. A densitometer system adapted for measuring color characteristics of object samples under test, said system comprising:

light source means for generating light rays and directing said light rays onto said object samples;

filter means responsive to light rays reflected from said object samples so as to discriminate a predetermined color shade set of spectral responses of said reflected light rays;

detection means responsive to light rays transmitted through said filter means for generating signals representative of the intensity of said light rays transmitted through said filter means;

processing means connected to said detection means for processing said signals and for generating data representative of color characteristics of said object samples under test;

input means connected to said processing means for providing operator input to said densitometer system;

motive means connected to said processing means and adapted to automatically move said object samples under test through said densitometer system adjacent said light source means, so as to provide an automated measurement of a plurality of color patches associated with said object samples; and guide means mounted to said densitometer system and adjustable by an operator of said system, so as to provide a guidance in at least one dimension of said object samples through said densitometer system.

3. A densitometer system in accordance with claim 2 characterized in that said filter means comprises reflection filter means positioned at a predetermined angle relative to the direction of object illumination by said light source means, and said reflection filter means is responsive to light rays reflected from said object samples so as to discriminate a predetermined color shade set of spectral responses of said reflected light rays.

4. A densitometer system in accordance with claim 3 characterized in that said detection means comprises reflection detection means responsive to light rays transmitted through said reflection filter means for generating, on separate paths, reflection signals representative of the intensity of said light rays transmitted through said reflection filter means.

5. A densitometer system in accordance with claim 4 characterized in that said system further comprises reflection multiplexing means connected to said reflection detection means for time multiplexing said reflection signals on said separate paths.

6. A densitometer system in accordance with claim 2 characterized in that said filter means comprises transmission filter means positioned relative to the direction of object illumination by said light source means, with said transmission filter means being responsive to light rays transmitted through said object samples so as to discriminate a predetermined color shade set of spectral responses of said transmitted light rays.

7. A densitometer system in accordance with claim 6 characterized in that said detection means comprises transmission detection means responsive to light rays transmitted through said transmission filter means for generating, on separate paths, transmission signals representative of the intensity of said light rays transmitted through said transmission filter means.

8. A densitometer system in accordance with claim 7 characterized in that said system further comprises transmission multiplexing means connected to said transmission detection means for time multiplexing said transmission signals on said separate paths.

9. A densitometer system in accordance with claim 2 characterized in that said system further comprises multiplexing means connected to said detection means for time multiplexing said signals.

10. A densitometer system in accordance with claim 2 characterized in that said system further comprises display means connected to said processing means for providing visual displays to said operator, indicative of functions performed by said densitometer system.

11. A densitometer system in accordance with claim 2 characterized in that said motive means comprises an electric motor.

12. A densitometer system in accordance with claim 2 characterized in that said guide means comprises a film guide bar having an elongated configuration, and further having nubs or similar elements adapted to be secured into slots located adjacent a forward edge of a bottom housing of said densitometer system.

13. A densitometer system in accordance with claim 12 characterized in that said guide means further comprises a pair of film guides, including a left film guide and a right film guide for capturing said object samples for guidance in at least one dimension into said densitometer system.

14. A densitometer system in accordance with claim 13 characterized in that said guide means further comprises a recessed portion of a housing assembly of said densitometer system, with said recessed portion including indicia for purposes of indicating the center of the path for color density measurements of said object samples under test.

15. A densitometer system in accordance with claim 14 characterized in that said guide means further comprises numerical indicia located on a forward edge of a bottom housing of said densitometer system, with said numerical indicia centered with respect to said indicia positioned on said recessed portion, and extending lengthwise across said forward edge, each of said film guides being manually adjustable by an operator for guiding and controlling guidance of said object samples into said densitometer system.

16. A densitometer system in accordance with claim 2 characterized in that said color characteristics include color densities, and:

at least one of said object samples is adapted for use as a calibration reference sample, said calibration reference sample comprising at least one reference color patch and calibration indicating means for indicating previously measured color density values of said reference color patch; and said densitometer system further comprises calibration means for adjusting slope between low and high color density measurements, said calibration means being adapted to read said calibration indicating means when said calibration reference sample is moved through said densitometer system adjacent said light source means, and to adjust said slope based at least in part on said values of said reference color patch represented by said calibration indicating means.

17. A densitometer system in accordance with claim 16 characterized in that said calibration indicating means comprises a plurality of indicators, and the position of each of said indicators is representative of a particular color density measurement value of said reference color patch.

18. A densitometer system in accordance with claim 16 characterized in that said calibration indicating means comprises a plurality of color indicators and a reference indicator, and the displacement of each of said color indicators relative to said reference indicator is representative of particular color density measurement values of said reference color patch.

19. A densitometer system in accordance with claim 16 characterized in that said calibration indicating means comprising a plurality of color indicators and a reference indicator, wherein the displacement of at least one of said color indicators relative to said reference indicator is representative of a particular color density measurement value of said reference color patch, and the displacement of at least another one of said color indicators relative to said reference indicator is representative of another particular color density measurement value of said reference color patch, but offset by a predetermined value so as to substantially avoid overlap of said plurality of color indicators.

20. A densitometer system in accordance with claim 2 characterized in that said system further comprises means for providing information to said operator as to appropriate positioning of said guide means for guidance of individual ones of said object samples through said densitometer system.

21. A densitometer system adapted for measuring color characteristics of object samples under test, said system comprising:

light source means for generating light rays and directing said light rays onto said object samples;

filter means comprising transmission filter means positioned relative to the direction of object illumination by said light source means, with said transmission filter means being responsive to light rays transmitted through said object samples so as to discriminate a predetermined color shade set of spectral responses of said transmitted light rays;

detection means responsive to light rays transmitted through said filter means for generating signals representative of the intensity of said light rays transmitted through said filter means;

processing means connected to said detection means for processing said signals and for generating data representative of color characteristics of said object samples;

motive means connected to said processing means and adapted to automatically move said object samples through said densitometer system adjacent said light source means, so as to provide and automated measurement of a plurality of color patches associated with said object samples; and guide means mounted to said densitometer system and adjustable by an operator of said system, so as to provide a guidance in at least one dimension of said object samples through said densitometer system.

22. A densitometer system in accordance with claim 21 characterized in that said filter means further comprises reflection filter means positioned at a predetermined angle relative to the direction of object illumination by said light source means, and said reflection filter means is responsive to light rays reflected from said object samples so as to discriminate a predetermined color shade set of spectral responses of said reflected light rays.

23. A densitometer system in accordance with claim 22 characterized in that said detection means comprises reflection detection means responsive to light rays transmitted through said reflection filter means for generating, on separate paths, reflection signals representative of the intensities of said light rays transmitted through said reflection filter means.

24. A densitometer system in accordance with claim 23 characterized in that said system further comprises reflection multiplexing means connected to said reflection detection means for time multiplexing said reflection signals on said separate paths.

25. A densitometer system in accordance with claim 21 characterized in that said detection means comprises transmission detection means responsive to light rays transmitted through said transmission filter means for generating, on separate paths, transmission signals representative of the intensity of said light rays transmitted through said transmission filter means.

26. A densitometer system in accordance with claim 25 characterized in that said system further comprises transmission multiplexing means connected to said transmission detection means for time multiplexing said transmission signals on said separate paths.

27. A densitometer system in accordance with claim 21 characterized in that said system further comprises multiplexing means connected to said detection means for time multiplexing said signals.

28. A densitometer system in accordance with claim 21 characterized in that said system further comprises display means connected to said processing means for providing visual displays to said operator, indicative of functions performed by said densitometer system.

29. A densitometer system in accordance with claim 21 characterized in that said motive means comprises an electric motor.

30. A densitometer system in accordance with claim 21 characterized in that said guide means comprises a film guide bar having an elongated configuration, and further having nubs or similar elements adapted to be secured into slots located adjacent a forward edge of a bottom housing of said densitometer system.

31. A densitometer system in accordance with claim 30 characterized in that said guide means further comprises a pair of film guide, including a left film guide and a right film guide for capturing said object samples for guidance in at least one dimension into said densitometer system.

32. A densitometer system in accordance with claim 31 characterized in that said guide means further comprises a recessed portion of a housing assembly of said densitometer system, with said recessed portion including indicia for purposes of indicating the center of the path for color density measurements of said object samples under test.

33. A densitometer system in accordance with claim 32 characterized in that said guide means further comprise numerical indicia located on a forward edge of a bottom housing of said densitometer system, with said numerical indicia centered with respect to said indicia positioned on said recessed portion, and extending lengthwise across said forward edge, each of said film guides being manually adjustable by an operator for guiding and controlling guidance of said object samples into said densitometer system.

34. A densitometer system in accordance with claim 21 characterized in that said color characteristics include color densities, and:

at least one of said object samples is adapted for use as a calibration reference sample, said calibration reference sample comprising at least one reference color patch and calibration indicating means for indicating previously measured color density values of said reference color patch; and said densitometer system further comprise calibration means for adjusting slope between low and high color density measurements, said calibration means being adapted to read said calibration indicating means when said calibration reference sample is moved through said densitometer system adjacent said light source means, and to adjust said slope based at least in part on said values of said reference color patch represented by said calibration indicating means.

35. A densitometer system in accordance with claim 34 characterized in that said calibration indicating means comprises a plurality of indicators, and the position of each of said indicators is representative of a particular color density measurement value of said reference color patch.

36. A densitometer system in accordance with claim 34 characterized in that said calibration indicating means comprises a plurality of color indicators and a reference indicator, and the displacement of each of said color indicators relative to said reference indicator is representative of particular color density measurement values of said reference color patch.

37. A densitometer system in accordance with claim 34 characterized in that said calibration indicating means comprising a plurality of color indicators and a reference indicator, wherein the displacement of at least one of said color indicators relative to said reference indicator is representative of a particular color density measurement value of said reference color patch, and the displacement of at least another one of said color indicators relative to said reference indicator is representative of another particular color density measurement value of said reference color patch, but offset by a predetermined value so as to substantially avoid overlap of said plurality of color indicators.

38. A densitometer system in accordance with claim 21 characterized in that said system further comprises means for providing information to said operator as to appropriate positioning of said guide means for guidance of individual ones of said object samples through said densitometer system.

39. A densitometer system adapted for measuring color characteristics of objects samples under test, said system comprising:
light source means for generating light rays and directing said light rays onto said object samples;
filter means responsive to light rays reflected from said object samples so as to discriminate a predetermined color shade set of spectral responses of said reflected light rays;
detection means responsive to light rays transmitted through said filter means for generating signals representative of the intensity of said light rays transmitted through said filter means;
processing means connected to said detection means for processing said signals and for generating data representative of color characteristics of said object samples under test;
motive means connected to said processing means and adapted to automatically move said object samples under test through said densitometer system adjacent said light source means, so as to provide an automated measurement of a plurality of color patches associated with said object samples;
guide means mounted to said densitometer system and adjustable by an operator of said system, so as to provide a guidance in at least one dimension of said object samples through said densitometer system;
said guide means comprising a film guide bar having an elongated configuration, and further having nubs or similar elements adapted to be secured into slots located adjacent a forward edge of a bottom housing of said densitometer system; and
said guide means further comprising a pair of film guides, including a left film guide and a right film guide for capturing said object samples for guidance in at least one dimension into said densitometer system.

40. A densitometer system in accordance with claim 39 characterized in that said guide means further comprises a recessed portion of a housing assembly of said densitometer system, with said recessed portion including indicia for purposes of indicating the center of the path for color density measurements of said object samples under test.

41. A densitometer system in accordance with claim 40 characterized in that said guide means further comprises numerical indicia located on a forward edge of a bottom housing of said densitometer system, with said numerical indicia centered with respect to said indicia positioned on said recessed portion and extending lengthwise across said forward edge, each of said film guides being manually adjustable by an operator for guiding and controlling guidance of said object samples into said densitometer system.

42. A densitometer system adapted for measuring color characteristics of object samples under test, said system comprising:
light source means for generating light rays and directed said light rays onto said object samples;
filter means responsive to light rays reflected from said object samples so as to discriminate a predetermined color shade set of spectral responses of said reflected light rays;
detection means responsive to light rays transmitted through said filter means for generating signals representative of the intensity of said light rays transmitted through said filter means;
processing means connected to said detection means for processing said signals and for generating data representative of color characteristics of said object samples under test;
motive means connected to said processing means and adapted to automatically move said object samples under test through said densitometer system adjacent said light source means, so as to provide an automated measurement of a plurality of color patches associated with said object samples;
guide means mounted to said densitometer system and adjustable by an operator of said system, so as to provide a guidance in at least one dimension of said object sample through said densitometer system;
said color characteristics include color densities, and at least one of said object samples is adapted for use as a calibration reference sample, said calibration reference sample comprising at least one reference color patch and color indicating means for indicating previously measured color density values of said reference color patch; and said densitometer system further comprises calibration means for adjusting slope between low and high color density measurements, said calibration means being adapted to read such calibration indicating means when said calibration reference sample is moved through said densitometer system adjacent said light source means, and to adjust said slope based at least in part on said values of said reference color patch represented by said calibration indicating means.

43. A densitometer system in accordance with claim 40 characterized in that said calibration indicating means comprises a plurality of indicators, and the position of each of said indicators is representative of a particular color density measurement value of said reference color patch.

44. A densitometer system in accordance with claim 42 characterized in that said calibration indicating means comprises a plurality of color indicators and a reference indicator, and the displacement of each of said color indicators relative to said reference indicator is representative of particular color density measurement values of said reference color patch.

45. A densitometer system in accordance with claim 42 characterized in that said calibration indicating means comprises a plurality of color indicators and a reference indicator, wherein the displacement of at least one of said color indicators relative to said reference indicator is representative of a particular color density measurement value of said reference color patch, and the displacement of at least another one of said color indicators relative to said reference indicator is representative of another particular color density measurement value of said reference color patch, but offset by a predetermined value so as to substantially avoid overlap of said plurality of color indicators.

* * * * *